(12) United States Patent
Doyle et al.

(10) Patent No.: US 12,227,575 B2
(45) Date of Patent: Feb. 18, 2025

(54) COMBINATION OF TIM-4 ANTAGONIST AND PD-1 ANTAGONIST AND METHODS OF USE

(71) Applicant: BRISTOL-MYERS SQUIBB COMPANY, Princeton, NJ (US)

(72) Inventors: Sean E. Doyle, Seattle, WA (US); Mark J. Selby, San Francisco, CA (US); Eric Chadwick, Bellevue, WA (US)

(73) Assignee: Bristol-Myers Squibb Company, Princeton, NJ (US)

(*) Notice: Subject to any disclaimer, the term of this patent is extended or adjusted under 35 U.S.C. 154(b) by 169 days.

(21) Appl. No.: 17/693,975

(22) Filed: Mar. 14, 2022

(65) Prior Publication Data

US 2022/0275091 A1 Sep. 1, 2022

Related U.S. Application Data

(62) Division of application No. 16/314,732, filed as application No. PCT/US2017/040665 on Jul. 5, 2017, now Pat. No. 11,306,143.

(60) Provisional application No. 62/359,073, filed on Jul. 6, 2016.

(51) Int. Cl.
| | |
|---|---|
| *C07K 16/28* | (2006.01) |
| *A61K 9/00* | (2006.01) |
| *A61K 39/00* | (2006.01) |
| *A61P 35/00* | (2006.01) |

(52) U.S. Cl.
CPC ........ *C07K 16/2818* (2013.01); *A61K 9/0019* (2013.01); *A61P 35/00* (2018.01); *C07K 16/2803* (2013.01); *A61K 2039/507* (2013.01); *C07K 2317/76* (2013.01)

(58) Field of Classification Search
None
See application file for complete search history.

(56) References Cited

U.S. PATENT DOCUMENTS

| | | |
|---|---|---|
| 7,943,743 B2 | 5/2011 | Korman et al. |
| 8,383,796 B2 | 2/2013 | Korman et al. |
| 9,102,725 B2 | 8/2015 | Korman et al. |
| 9,580,505 B2 | 2/2017 | Korman et al. |
| 9,580,507 B2 | 2/2017 | Korman et al. |
| 11,306,143 B2 | 4/2022 | Doyle et al. |
| 2019/0389950 A1 | 12/2019 | Doyle et al. |
| 2020/0062848 A1 | 2/2020 | Korman et al. |

FOREIGN PATENT DOCUMENTS

| | | |
|---|---|---|
| CN | 101035561 A | 9/2007 |
| CN | 102861319 A | 1/2013 |
| JP | 2015-209376 A | 11/2015 |
| WO | 2006/121168 A1 | 11/2006 |
| WO | 2007/005874 A2 | 1/2007 |
| WO | 2015/048312 A1 | 4/2015 |

OTHER PUBLICATIONS

Agata, Y. et al., "Expression of the PD-1 antigen on the surface of stimulated mouse T and B lymphocytes," Int Immunol., vol. 8:765-72 (1996).
Albacker, L. et al., "TIM-4, a Receptor for Phosphatidylserine, Controls Adaptive Immunity by Regulating the Removal of Antigen-Specific T Cells," J. Immunol., vol. 185:6839-6849 (2010.
Baghdadi, M. et al., "Combined blockade of TIM-3 and TIM-4 augments cancer vaccine efficacy against established melanomas," Cancer Immunology Immunotherapy, vol. 62(4):629-637 (2013).
Bennett, F. et al., "Program death-1 engagement upon TCR activation has distinct effects on costimulation and cytokine-driven proliferation: attenuation of ICOS, IL-4, and IL-21, but not CD28, IL-7, and IL-15 responses," J. Immunol 170:711-8 (2003).
Blank, C. et al., "Interaction of PD-L1 on tumor cells with PD-1 on tumor-specific T cells as a mechanism of immune evasion: implications for tumor immunotherapy," Cancer Immunol. Immunother., 54:307-314 (2005).
Brown, J. et al., "Blockade of Programmed Death-1 Ligands on Dendritic Cells Enhances T Cell Activation and Cytokine Production" J. Immunol., vol. 170:1257-1266 (2003).
Carter, L. et al., "PD-1:PD-L inhibitory pathway affects both CD4(+) and CD8(+) T cells and is overcome by IL-2.," Eur J Immunol., vol. 32:634-643 (2002).
Cheng, L. et al., "Tim-3 and Tim-4 as the potential targets for antitumor therapy," Human Vaccines & Immunotherapeutics, vol. 11(10): 2458-2462 (2015).
Dong, H. et al., "B7-H1 pathway and its role in the evasion of tumor immunity," J. Mol. Med., vol. 81:281-287 (2003).
Dong, H. et al., "Tumor-associated B7-H1 promotes T-cell apoptosis: A potential mechanism of immune evasion," Nat. Med., vol. 8:787-789 (2002).
Freeman, G.J. et al., "Engagement of the PD-1 Immunoinhibitory Receptor by a Novel B7 Family Member Leads to Negative Regulation of Lymphocyte Activation," J Exp Med., vol. 192:1027-1034 (2000).
Henricks, L. et al., "The use of combinations of monoclonal antibodies in clinical oncology," Cancer Treat Rev., vol. 41(10):859-867 (2015).
International Preliminary Report on Patentability, PCT/US2017/040665, dated Jan. 8, 2019, 6 pages.
International Search Report and Written Opinion, PCT/US2017/040665, dated Oct. 9, 2017, 9 pages.
Ishida, Y. et al., "Induced Expression of PD-1, a Novel Member of the Immunoglobulin Gene Superfamily, Upon Programmed Cell Death," EMBO J., vol. 11(38): 87-95 (1992).
Iwai, Y. et al., "Involvement of PD-L1 on tumor cells in the escape from host immune system and tumor immunotherapy by PD-L1 blockade," Proc. Natl. Acad. Sci., vol. 99:12293-12297 (2002).

(Continued)

*Primary Examiner* — Brian Gangle
(74) *Attorney, Agent, or Firm* — Nelson Mullins Riley & Scarborough LLP; Jane E. Remillard, Esq.; Jeanne DiGiorgio, Esq.

(57) ABSTRACT

Provided are methods and compositions for treating cancer using an effective amount of a PD-1 antagonist (e.g., an antibody) in combination with a TIM-4 antagonist (e.g., an antibody).

15 Claims, 12 Drawing Sheets

Specification includes a Sequence Listing.

(56) References Cited

OTHER PUBLICATIONS

Kim, J. et al., "Combination Therapy with Anti-PD-1, Anti-TIM-3, and Focal Radiation Re-sults in Regression of Murine Gliomas," Clinical Cancer Research, vol. 23(1): 124-136 (2016).

Konishi, J. et al., "B7-H1 Expression on Non-Small Cell Lung Cancer Cells and Its Relationship with Tumor-Infiltrating Lymphocytes and Their PD-1 Expression," Clin. Cancer Res., vol. 10:5094-5100 (2004).

Koyama, S. et al., "Adaptive resistance to therapeutic PD-1 blockade is associated with upregulation of alternative immune checkpoints," Nature Communications, vol. 7: 10501(2016).

Latchman, Y. et al., "PD-L2 is a second ligand for PD-1 and inhibits T cell activation," Nat. Immunol 2:261-8 (2001).

Mizui, M. et al., "Bimodal regulation of T cell-mediated immune responses by TIM-4," Int. Immunol., vol. 20:695-708 (2008).

Nielsen, C. et al., "A Putative Regulatory Polymorphism in PD-1 Is Associated With Nephropathy in a Population-Based Cohort of Systemic Lupus Erythematosus Patients," Lupus, vol. 13:510-516 (2004).

Nishi, C. et al., "Tim4- and MerTK-Mediated Engulfment of Apoptotic Cells by Mouse Resident Peritoneal Macrophages," Mol Cell Biol., vol. 34(8):1512-1520 (2014).

Nishimura, H. et al., "Autoimmune Dilated Cardiomyopathy in PD-1 Receptor-Deficient Mice," Science, vol. 291:319-322 (2001).

Nishimura, H. et al., "Development of Lupus-like Autoimmune Diseases by Disruption of the PD-1 Gene Encoding an ITIM Motif-Carrying Immunoreceptor," Immunity, vol. 11:141-51 (1999).

Okazaki, T. et al., "New regulatory co-receptors: inducible co-stimulator and PD-1," Curr. Opin. Immunol., vol. 14 (39):1779-1782 (2002).

Okazaki, T. et al., "PD-1 Immunoreceptor Inhibits B Cell Receptor-Mediated Signaling by Recruiting Src Homology 2-domain-containing Tyrosine Phosphatase 2 to Phosphotyrosine," PNAS, vol. 98(13): 866-781 (2001).

Opdivo prescribing information (Bristol-Myers Squibb Company, Dec. 2014).

Page, N. et al., "Genetic Association Studies between the T Cell Immunoglobulin Mucin (TIM) Gene Locus and Childhood Atopic Dermatitis," Int Arch Allergy Immunol., vol. 141(4):331-336 (2006).

Prokunina, L. et al., "The Genetic Basis of Systemic Lupus Erythematosus—Knowledge of Today and Thoughts for Tomorrow," Hum Mol Genet., vol. 13:R143 (2004).

Rizvi, N. et al., "Activity and safety of nivolumab, an anti-PD-1 immune checkpoint inhibitor, for patients with advanced, refractory squamous non-small-cell lung cancer (CheckMate 063): a phase 2, single-arm trial," Lancet Oncol, vol. 16 (3):257-265 (2015).

Sakuishi, K. et al., "Targeting Tim-3 and PD-1 pathways to reverse T cell exhaustion and restore anti-tumor immunity," J. Exp. Med., vol. 207 (10): 2187-2194 (2010).

Salama, A. et al., "Critical Role of the Programmed death-1 (PD-1) Pathway in Regulation of Experimental Autoimmune Encephalomyelitis," J. Exp Med., vol. 198:71-78 (2003).

Thomas, M.L., "Of ITAMs and ITIMs: Turning on and off the B Cell Antigen Receptor," J Exp Med., vol. 181:1953-1956 (1995).

Toda, S.. et al. "Two-Step Engulfment of Apoptotic Cells," Mol Cell Biol., vol. 32(1):118-125 (2012).

Vivier, E and Daeron, M., "Immunoreceptor Tyrosine-Based Inhibition Motifs," Immunol. Today, vol. 18:286-91 (1997).

U.S. Appl. No. 16/314,732, filed Jan. 2, 2019, Sean E. Doyle, U.S. Pat. No. 11,306,143.

```
                            10         20         30         40         50
hum_TIM4_1_NP_612388      MSKEPLIILWLMIEFWWLYLTPVTSETVVTEVLGHRVTLPCLYSSWSHNSN    50
hum_TIM4_2_NP_001140198   MSKEPLIILWLMIEFWWLYLTPVTSETVVTEVLGHRVTLPCLYSSWSHNSN    50

60         70         80         90        100
hum_TIM4_1_NP_612388      SMCWGKDQCPYSGCKEALIRTDGMRVTSRKSAKYRLQGTIPRGDVSLTIL   100
hum_TIM4_2_NP_001140198   SMCWGKDQCPYSGCKEALIRTDGMRVTSRKSAKYRLQGTIPRGDVSLTIL   100

110        120        130        140        150
hum_TIM4_1_NP_612388      NPSESDSGVYCCRIEVPGWFNDVKINVRLNLQRASTTTHRTATTTTRRTT   150
hum_TIM4_2_NP_001140198   NPSESDSGVYCCRIEVPGWFNDVKINVRLNLQRASTTTHRTATTTTRRTT   150

160        170        180        190        200
hum_TIM4_1_NP_612388      TTSPTTTRQMTTTPAALPTTVVTTPDLTTGTPLQMTTIAVFTTANTCLSL   200
hum_TIM4_2_NP_001140198   TTSPTTTRQMTTTPAALPTTVVTTPDLTTGTPLQMTTIAVFTTANTCLSL   200

210        220        230        240        250
hum_TIM4_1_NP_612388      TPSTLPEEATGLLTPEPSKEGPILTAESETVLPSDSWSSVESTSADTVLL   250
hum_TIM4_2_NP_001140198   TPSTLPEEATGLLTPEPSKEGPILTAESETVLPSDSWSSVESTSADTVLL   250

260        270        280        290        300
hum_TIM4_1_NP_612388      TSKESKVWDLPSTSHVSMWKTSDSVSSPQPGASDTAVPEQNKTTKTGQMD   300
hum_TIM4_2_NP_001140198   TSK---------------------ASDTAVPEQNKTTKTGQMD         272

310        320        330        340        350
hum_TIM4_1_NP_612388      GIPMSMKNEMPISQLLMIIAPSLGFVLFALFVAFLLRGKLMETYCSQKHT   350
hum_TIM4_2_NP_001140198   GIPMSMKNEMPISQLLMIIAPSLGFVLFALFVAFLLRGKLMETYCSQKHT   322

360        370
hum_TIM4_1_NP_612388      RLDYIGDSKNVLNDVQHGREDEDGLFTL   378
hum_TIM4_2_NP_001140198   RLDYIGDSKNVLNDVQHGREDEDGLFTL   350
```

▬ IG-like domain   *S/T rich domain (mucin )*   Signal/Transmembrane domain

CYS (C-C) pairs are based on 4JJH and 4QYC structures

FIGURE 1

```
                                10         20         30         40         50         60         70
TIM4_cyno1_EHH54702      MSKEPLIIWLMVMEFWWLYLTPVTSETVVTEVLGHRVTLPCLYSSWSQNSNSMCWGKDKCPYSGCKEALIRTDGTR    75
TIM4_cyno2_XP_005558436  MSKEPLIIWLMVMEFWWLYLTPVTSETVVTEVLGHRVTLPCLYSSWSQNSNSMCWGKDKCPYSGCKEALIRTDGTR    75
hum_TIM4_1NP_612388      MSKEPLILWLMLMEFWWLYLTPVTSETVVTEVLGHRVTLPCLYSSWSHNSNSMCWGKDQCPYSGCKEALIRTDGMR    75
TIM4_mus_NP_848874       MSKGLLLWLVTELWMLYLTPAASEDTIIGFLGQPVTLPCHYLSWSQSRNSMCWGKGSCPNSKCNAELLRTDGTR     75

80         90        100        110        120        130        140       150
TIM4_cyno1_EHH54702      VTSRKSAKYRLPGTIQRGNVSLTILNPREGDSGVYCCRIEVPGWFNDVKINVRLNLQRETCLLLVTASTTTRRTR    150
TIM4_cyno2_XP_005558436  VTSRKSAKYRLPGTIQRGNVSLTILNPREGDSGVYCCRIEVPGWFNDVKINVRLNLQR------ASTTTRRTR    142
hum_TIM4_1NP_612388      VTSRKSAKYRLQGTIPRGDVSLTILNPSESDSGVYCCRIEVPGWFNDVKINVRLNLQRASTTTHRTATTTRRTT    150
TIM4_mus_NP_848874       IISRKSTKYTLLGKVQFGEVSLTISNTNRGDSGVYCCRIEVPGWFNDVKKNVRLELRR------ATTTKKPTT   142

160        170        180        190        200        210        220
TIM4_cyno1_EHH54702      TTSPPTTPHVTTTR-AALPTTVMTTPDLTTETPLQTTTTAVFTTAN-TCPSPTPSTLPEAATGLLTPEPSKEGPI   223
TIM4_cyno2_XP_005558436  TTSPPTTPHVTTTR-AALPTTVMTTPDLTTETPLQTTTTAVFTTAN-TCPSPTPSTLPEAATGLLTPEPSKEGPI   215
hum_TIM4_1NP_612388      TTSPPTTRQMTTTR-AALPTTVMTTPDLTTGTPLQMTTIAVFTTAN-TCPSPTPSTLPEAATGLLTPEPSKEGPI   223
TIM4_mus_NP_848874       TTRPTTTPYVTTTTPELLPTTVMTTSVLPTTTPQTLATTAFSTAVTTCPSTTPGSFSQETT------KGSA     208

230        240        250        260        270        280        290        300
TIM4_cyno1_EHH54702      LTAESEPVLPS-DSWSSTESP-ADTVLLTSRESKVWDLPPTSHVSMWKTSDSVSSPQPGASDTAVPEQNKTTKTG   296
TIM4_cyno2_XP_005558436  LTAESEPVLPS-DSWNSTESP-ADTVLLTSRESKVWDLPPTSHVSMWTTSDSVSSPQPGASDTAVPEQNKTTKTG   288
hum_TIM4_1NP_612388      LTAESETVLPS-DSWSSVESTSADTVLLTSKESKVWDLPSTSHVSMWKTSDSVSSPQPGASDTAVPEQNKTTKTG   297
TIM4_mus_NP_848874       FTTESETLPASNGSQRSMMTISTDIAVLRPTGSNPGILPSTSQLTTQKTTLTTSES------LQKTTKSH      272

310        320        330        340        350        360        370
TIM4_cyno1_EHH54702      QMDGMPMPMKNEMPISQLLMLIAPSLGFVLLA-LLMAFLLRGKLMETNCLQKHTRLDCIGDSKNVLNDMRHGRED   370
TIM4_cyno2_XP_005558436  QMDGMPMPMKNEMPISQLLMLIAPSLGFVLLA-LLMAFLLRGKLMETNCLQKHTRLDCIGDSKNVLNDMRHGRED   362
hum_TIM4_1NP_612388      QMDGIPMSMKNEMPISQLLMLIAPSLGFVLFA-LFVAFLLRGKLMETYCSQKHTRLDYIGDSKNVLNDVQHGRED   371
TIM4_mus_NP_848874       SRQTILIIACCVGFVLMVLLFLLAFLLRGKVTGANCLQRHKRPDNTEDSDSVLNDMSHGRDD               336

380
TIM4_cyno1_EHH54702      EDGLFTL  377
TIM4_cyno2_XP_005558436  EDGLFTL  369
hum_TIM4_1NP_612388      EDGLFTL  378
TIM4_mus_NP_848874       EDGLFTL  343
```

FIGURE 2

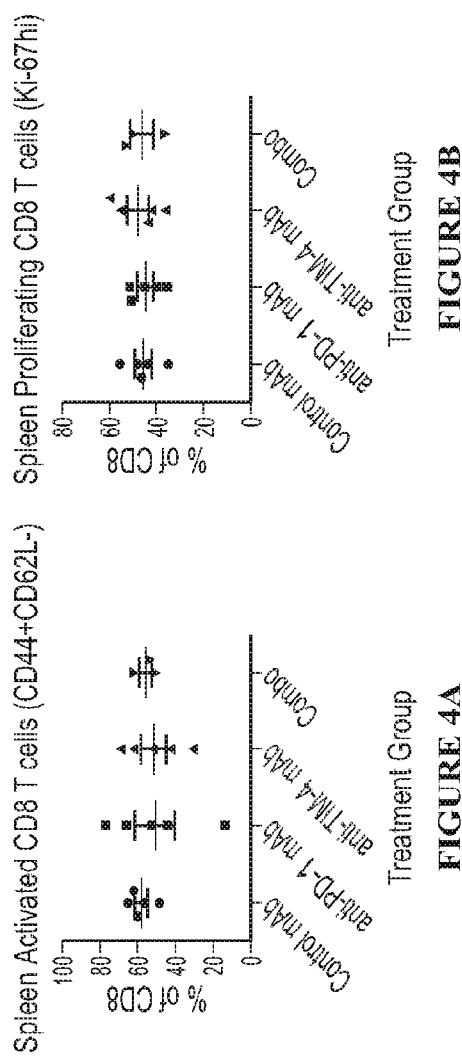
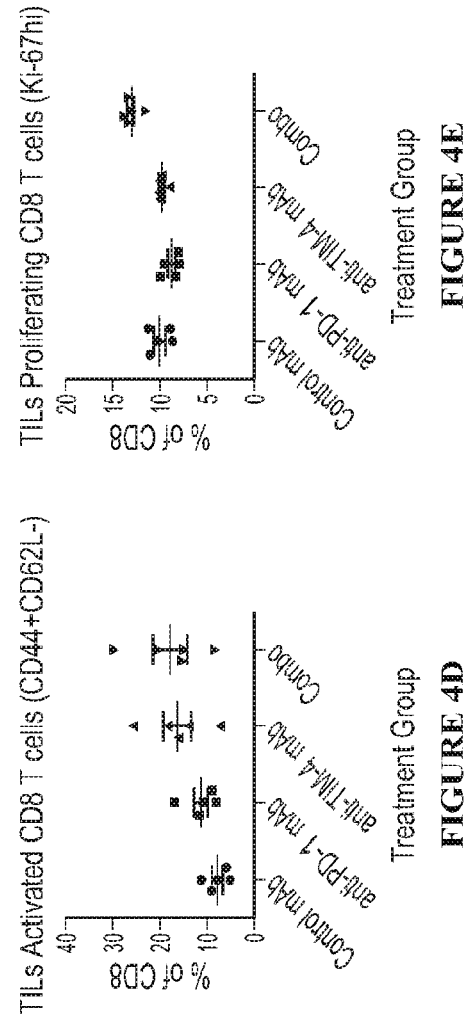

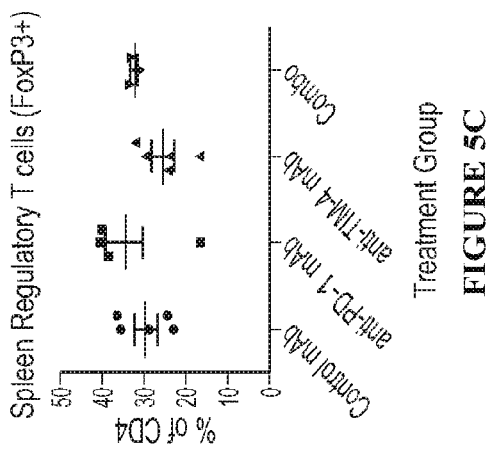
FIGURE 5C
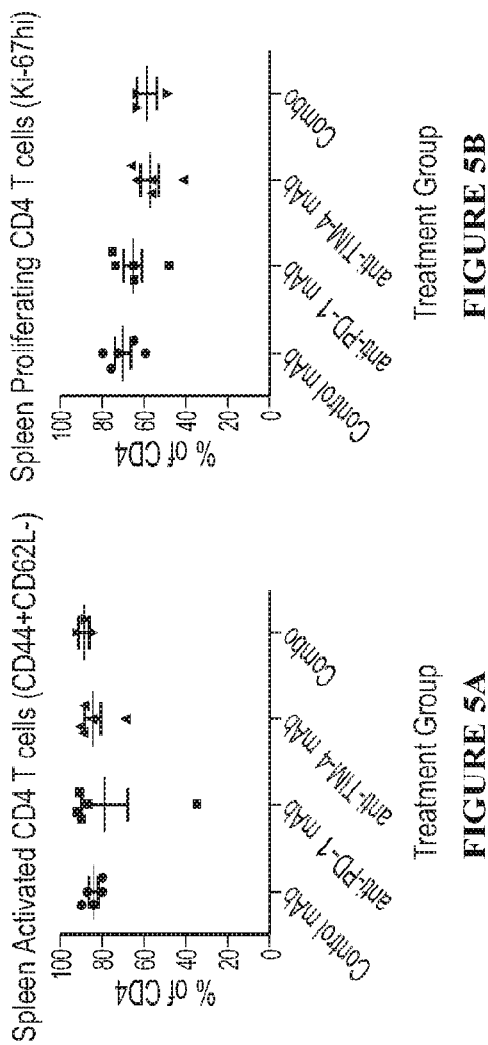
FIGURE 5A
FIGURE 5B
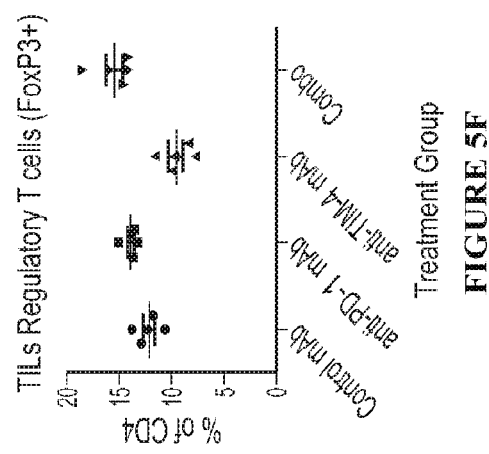
FIGURE 5F
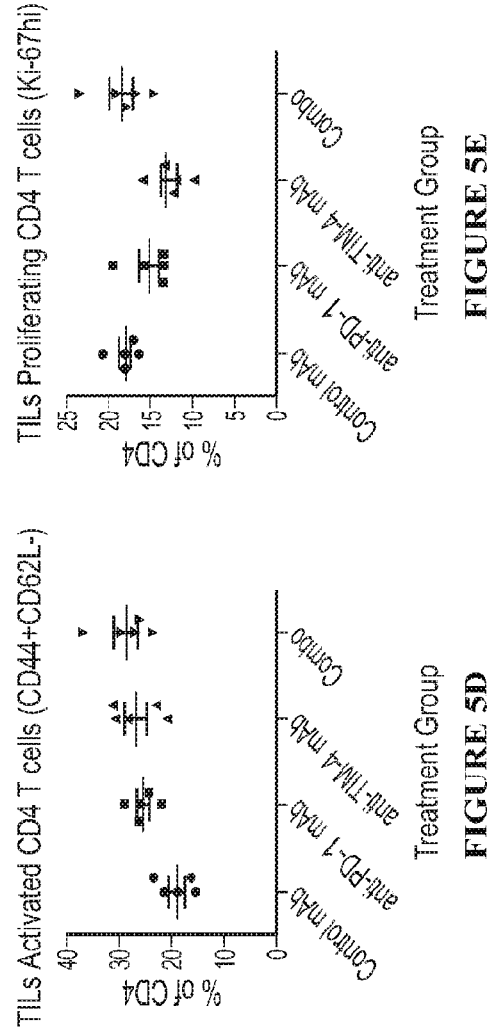
FIGURE 5D
FIGURE 5E

SEQUENCE LISTING

<160> NUMBER OF SEQ ID NOS: 32

<210> SEQ ID NO 1
<211> LENGTH: 123
<212> TYPE: PRT
<213> ORGANISM: Artificial Sequence
<220> FEATURE:
<223> OTHER INFORMATION: Synthetic: Heavy Chain Variable Region (VH)
      Amino Acid Sequence Anti-PD-L1 mAb (12A4; 12A4 in WO 2007/005874
      and US Patent No. 7,943,743)

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120

<210> SEQ ID NO 2
<211> LENGTH: 366
<212> TYPE: DNA
<213> ORGANISM: Artificial Sequence
<220> FEATURE:
<223> OTHER INFORMATION: Synthetic: Heavy Chain Variable Region (VH)
      Nucleotide Sequence Anti-PD-L1 mAb (12A4; 12A4 in WO 2007/005874
      and US Patent No. 7,943,743)

<400> SEQUENCE: 2
caggtccagc tggtgcagtc tggggctgag gtgaagaagc ctgggtcctc ggtgaaggtc     60
tcctgcaaga cttctggaga caccttcagc acctatgcta tcagctgggt gcgacaggcc    120
cctggacaag gcttgagtg gatgggaggg atcatcccta tatttggtaa agcacactac    180
gcacagaagt tccagggcag agtcacgatt accgcggacg aatccacgag cacagcctac    240
atggagctga gcagcctgag atctgaggac acggccgtgt attttgtgc gagaaagttt    300 cactttgttt cggggagccc cttcggtatg gacgtctggg gccaagggac cacggtcacc    360
gtctcc                                                                          366

<210> SEQ ID NO 3
<211> LENGTH: 106
<212> TYPE: PRT
<213> ORGANISM: Artificial Sequence
<220> FEATURE:
<223> OTHER INFORMATION: Synthetic: Light Chain Variable Region (VL)
      Amino Acid Sequence Anti-PD-L1 mAb (12A4; 12A4 in WO 2007/005874
      and US Patent No. 7,943,743)

<400> SEQUENCE: 3

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 4
<211> LENGTH: 318
<212> TYPE: DNA
<213> ORGANISM: Artificial Sequence
<220> FEATURE:
<223> OTHER INFORMATION: Synthetic: Light Chain Variable Region (VL)
      Nucleotide Sequence Anti-PD-L1 mAb (12A4; 12A4 in WO 2007/005874
      and US Patent No. 7,943,743)

<400> SEQUENCE: 4
gaaattgtgt tgacacagtc tccagccacc ctgtctttgt ctccagggga aagagccacc       60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggccgacgtt cggccaaggg     300
accaaggtgg aaatcaaa                                                    318

<210> SEQ ID NO 5
<211> LENGTH: 5
<212> TYPE: PRT
<213> ORGANISM: Artificial Sequence
<220> FEATURE:
<223> OTHER INFORMATION: Synthetic: Heavy Chain CDR1 Amino Acid Sequence
      Anti-PD-L1 mAb (12A4; 12A4 in WO 2007/005874 and US Patent No.
      7,943,743)

<400> SEQUENCE: 5

Thr Tyr Ala Ile Ser
1               5

<210> SEQ ID NO 6
<211> LENGTH: 16
<212> TYPE: PRT

```
<213> ORGANISM: Artificial Sequence
<220> FEATURE:
<223> OTHER INFORMATION: Synthetic: Heavy Chain CDR2 Amino Acid Sequence
      Anti-PD-L1 mAb (12A4; 12A4 in WO 2007/005874 and US Patent No.
      7,943,743)

<400> SEQUENCE: 6

Gly Ile Ile Pro Ile Phe Gly Lys Ala His Tyr Ala Gln Lys Phe Gln
1               5                   10                  15

<210> SEQ ID NO 7
<211> LENGTH: 14
<212> TYPE: PRT
<213> ORGANISM: Artificial Sequence
<220> FEATURE:
<223> OTHER INFORMATION: Synthetic: Heavy Chain CDR3 Amino Acid Sequence
      Anti-PD-L1 mAb (12A4; 12A4 in WO 2007/005874 and US Patent No.
      7,943,743)

<400> SEQUENCE: 7

Lys Phe His Phe Val Ser Gly Ser Pro Phe Gly Met Asp Val
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic: Light Chain CDR1 Amino Acid Sequence
      Anti-PD-L1 mAb (12A4; 12A4 in WO 2007/005874 and US Patent No.
      7,943,743)

<400> SEQUENCE: 8

Arg Ala Ser Gln Ser Val Ser Ser Tyr Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic: Light Chain CDR2 Amino Acid Sequence
      Anti-PD-L1 mAb (12A4; 12A4 in WO 2007/005874 and US Patent No.
      7,943,743)

<400> SEQUENCE: 9

Asp Ala Ser Asn Arg Ala Thr
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic: Light Chain CDR3 Amino Acid Sequence
      Anti-PD-L1 mAb (12A4; 12A4 in WO 2007/005874 and US Patent No.
      7,943,743)

<400> SEQUENCE: 10

Gln Gln Arg Ser Asn Trp Pro Thr
1               5

<210> SEQ ID NO 11
<211> LENGTH: 440
<212> TYPE: PRT
<213> ORGANISM: Artificial Sequence
<220> FEATURE:
<223> OTHER INFORMATION: Synthetic: Heavy Chain Amino Acid Sequence
      Anti-PD-1 mAb (5C4 in WO 2006/121168) (variable region underlined;
``` constant region bold)

<400> SEQUENCE: 11

```
Gln Val Gln Leu Val Glu Ser Gly Gly Gly Val Val Gln Pro Gly Arg
  1               5                  10                  15

Ser Leu Arg Leu Asp Cys Lys Ala Ser Gly Ile Thr Phe Ser Asn Ser
             20                  25                  30

Gly Met His Trp Val Arg Gln Ala Pro Gly Lys Gly Leu Glu Trp Val
         35                  40                  45

Ala Val Ile Trp Tyr Asp Gly Ser Lys Arg Tyr Tyr Ala Asp Ser Val
     50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400
```

```
Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 12
<211> LENGTH: 214
<212> TYPE: PRT
<213> ORGANISM: Artificial Sequence
<220> FEATURE:
<223> OTHER INFORMATION: Synthetic: Light Chain Amino Acid Sequence
      Anti-PD-1 mAb (5C4 in WO 2006/121168) (variable region underlined;
      constant region bold)

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 113
<212> TYPE: PRT
<213> ORGANISM: Artificial Sequence
<220> FEATURE:
<223> OTHER INFORMATION: Synthetic: Heavy Chain Variable Region (VH)
      Amino Acid Sequence Anti-PD-1 mAb (5C4 in WO 2006/121168) (SEQ ID
      NO:4 from WO 2006/121168)

<400> SEQUENCE: 13

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
```

```
                        20                  25                  30
Gly Met His Trp Val Arg Gln Ala Pro Gly Lys Gly Leu Glu Trp Val
                35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
                100                 105                 110

Ser

<210> SEQ ID NO 14
<211> LENGTH: 339
<212> TYPE: DNA
<213> ORGANISM: Artificial Sequence
<220> FEATURE:
<223> OTHER INFORMATION: Synthetic: Heavy Chain Variable Region (VH)
      Nucleotide Sequence Anti-PD-1 mAb (5C4 in WO 2006/121168) (SEQ ID
      NO:60 from WO 2006/121168)

<400> SEQUENCE: 14
caggtgcagc tggtggagtc tgggggaggc gtggtccagc ctgggaggtc cctgagactc        60
gactgtaaag cgtctggaat caccttcagt aactctggca tgcactgggt ccgccaggct       120
ccaggcaagg gctggagtg gtggcagtt atttggtatg atggaagtaa aagatactat        180
gcagactccg tgaagggccg attcaccatc tccagagaca attccaagaa cacgctgttt       240
ctgcaaatga acagcctgag agccgaggac acggctgtgt attactgtgc gacaaacgac       300
gactactggg gccagggaac cctggtcacc gtctcctca                              339

<210> SEQ ID NO 15
<211> LENGTH: 107
<212> TYPE: PRT
<213> ORGANISM: Artificial Sequence
<220> FEATURE:
<223> OTHER INFORMATION: Synthetic: Light Chain Variable Region (VL)
      Amino Acid Sequence Anti-PD-1 mAb (5C4 in WO 2006/121168) (SEQ ID
      NO:11 from WO 2006/121168)

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
                35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
                100                 105

<210> SEQ ID NO 16
<211> LENGTH: 321
```

```
<212> TYPE: DNA
<213> ORGANISM: Artificial Sequence
<220> FEATURE:
<223> OTHER INFORMATION: Synthetic: Light Chain Variable Region (VL)
      Nucleotide Sequence Anti-PD-1 mAb (5C4 in WO 2006/121168) (SEQ ID
      NO:67 from WO 2006/121168)

<400> SEQUENCE: 16
gaaattgtgt tgacacagtc tccagccacc ctgtctttgt ctccagggga aagagccacc      60
ctctcctgca gggccagtca gagtgttagt agttacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag agtagcaact ggcctcggac gttcggccaa    300
gggaccaagg tggaaatcaa a                                              321

<210> SEQ ID NO 17
<211> LENGTH: 5
<212> TYPE: PRT
<213> ORGANISM: Artificial Sequence
<220> FEATURE:
<223> OTHER INFORMATION: Synthetic: Heavy Chain CDR1 Amino Acid Sequence
      Anti-PD-1 mAb (5C4 in WO 2006/121168) (SEQ ID NO:18 from WO
      2006/121168)

<400> SEQUENCE: 17

Asn Ser Gly Met His
1               5

<210> SEQ ID NO 18
<211> LENGTH: 17
<212> TYPE: PRT
<213> ORGANISM: Artificial Sequence
<220> FEATURE:
<223> OTHER INFORMATION: Synthetic: Heavy Chain CDR2 Amino Acid Sequence
      Anti-PD-1 mAb (5C4 in WO 2006/121168) (SEQ ID NO:25 from WO
      2006/121168)

<400> SEQUENCE: 18

Val Ile Trp Tyr Asp Gly Ser Lys Arg Tyr Tyr Ala Asp Ser Val Lys
1               5                   10                  15
Gly

<210> SEQ ID NO 19
<211> LENGTH: 4
<212> TYPE: PRT
<213> ORGANISM: Artificial Sequence
<220> FEATURE:
<223> OTHER INFORMATION: Synthetic: Heavy Chain CDR3 Amino Acid Sequence
      Anti-PD-1 mAb (5C4 in WO 2006/121168) (SEQ ID NO:32 from WO
      2006/121168)

<400> SEQUENCE: 19

Asn Asp Asp Tyr
1

<210> SEQ ID NO 20
<211> LENGTH: 11
<212> TYPE: PRT
<213> ORGANISM: Artificial Sequence
<220> FEATURE:
<223> OTHER INFORMATION: Synthetic: Light Chain CDR1 Amino Acid Sequence
      Anti-PD-1 mAb (5C4 in WO 2006/121168) (SEQ ID NO:39 from WO
      2006/121168)

<400> SEQUENCE: 20
```

Arg Ala Ser Gln Ser Val Ser Ser Tyr Leu Ala
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic: Light Chain CDR2 Amino Acid Sequence
      Anti-PD-1 mAb (5C4 in WO 2006/121168) (SEQ ID NO:46 from WO
      2006/121168)

<400> SEQUENCE: 21

Asp Ala Ser Asn Arg Ala Thr
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic: Light Chain CDR3 Amino Acid Sequence
      Anti-PD-1 mAb (5C4 in WO 2006/121168) (SEQ ID NO:53 from WO
      2006/121168)

<400> SEQUENCE: 22

Gln Gln Ser Ser Asn Trp Pro Arg Thr
1               5

<210> SEQ ID NO 23
<211> LENGTH: 2106
<212> TYPE: DNA
<213> ORGANISM: Homo sapiens
<220> FEATURE:
<221> NAME/KEY: misc_feature
<222> LOCATION: (1)..(2106)
<223> OTHER INFORMATION: Complete PD-1 sequence

<400> SEQUENCE: 23
agtttccctt ccgctcacct ccgcctgagc agtggagaag gcggcactct ggtgggctg      60 ctccaggcat gcagatccca caggcgccct ggccagtcgt ctgggcggtg ctacaactgg    120
gctggcggcc aggatggttc ttagactccc cagacaggcc ctggaacccc ccaccttct    180 tcccagccct gctcgtggtg accgaagggg acaacgccac cttcacctgc agcttctcca    240
acacatcgga gagcttcgtg ctaaactggt accgcatgag cccagcaac cagacggaca    300 agctggccgc cttccccgag gaccgcagcc agcccggcca ggactgccgc ttccgtgtca    360
cacaactgcc caacgggcgt gacttccaca tgagcgtggt cagggcccgg cgcaatgaca    420
gcggcaccta cctctgtggg gccatctccc tggccccca ggcgcagatc aaagagagcc    480
tgcgggcaga gctcagggtg acagagagaa gggcagaagt gcccacagcc accccagcc    540 cctcacccag gccagccggc cagttccaaa ccctggtggt tggtgtcgtg gcggcctgc    600 tgggcagcct ggtgctgcta gtctgggtcc tggccgtcat ctgctcccgg gccgcacgag    660
ggacaatagg agccaggcgc accggccagc ccctgaagga ggacccctca gccgtgcctg    720
tgttctctgt ggactatggg gagctggatt ccagtggcg agagaagacc ccggagcccc    780
ccgtgccctg tgtccctgag cagacggagt atgccaccat tgtctttcct agcggaatgg    840
gcacctcatc cccgcccgc aggggctcag ccgacggccc tcggagtgcc agccactga    900 ggcctgagga tggacactgc tcttggcccc tctgaccggc ttccttggcc accagtgttc    960
tgcagaccct ccaccatgag cccgggtcag cgcatttcct caggagaagc aggcagggtg   1020

```
caggccattg caggccgtcc aggggctgag ctgcctgggg gcgaccgggg ctccagcctg    1080
cacctgcacc aggcacagcc ccaccacagg actcatgtct caatgcccac agtgagccca    1140
ggcagcaggt gtcaccgtcc cctacaggga gggccagatg cagtcactgc ttcaggtcct    1200
gccagcacag agctgcctgc gtccagctcc ctgaatctct gctgctgctg ctgctgctgc    1260
tgctgctgcc tgcggcccgg ggctgaaggc gccgtggccc tgcctgacgc cccggagcct    1320
cctgcctgaa cttgggggct ggttggagat ggccttggag cagccaaggt gcccctggca    1380
gtggcatccc gaaacgccct ggacgcaggg cccaagactg gcacaggag tgggaggtac    1440 atggggctgg ggactcccca ggagttatct gctccctgca ggcctagaga agtttcaggg    1500
aaggtcagaa gagctcctgg ctgtggtggg cagggcagga aacccctccc acctttacac    1560
atgcccaggc agcacctcag gccctttgtg gggcagggaa gctgaggcag taagcgggca    1620
ggcagagctg gaggcctttc aggccagcca gcactctggc ctcctgccgc cgcattccac    1680
cccagcccct cacaccactc gggagaggga catcctacgg tcccaaggtc aggagggcag    1740
ggctggggtt gactcaggcc cctcccagct gtggccacct gggtgttggg agggcagaag    1800
tgcaggcacc tagggccccc catgtgccca ccctgggagc tctccttgga acccattcct    1860
gaaattattt aaaggggttg gccgggctcc caccagggcc tgggtgggaa ggtacaggcg    1920
ttccccgggg gcctagtacc cccgcgtggc ctatccactc ctcacatcca cacactgcac    1980
ccccactcct ggggcagggc caccagcatc caggcggcca gcaggcacct gagtggctgg    2040
gacaagggat ccccctttccc tgtggttcta ttatattata attataatta aatatgagag    2100
catgct                                                               2106
```

<210> SEQ ID NO 24
<211> LENGTH: 290
<212> TYPE: PRT
<213> ORGANISM: Homo sapiens
<220> FEATURE:
<221> NAME/KEY: misc_feature
<222> LOCATION: (1)..(290)
<223> OTHER INFORMATION: Human PD-L1 amino acid sequence - isoform a
      precursor

<400> SEQUENCE: 24

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

```
Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
                195                 200                 205

Cys Thr Phe Arg Arg Leu Asp Pro Glu Glu Asn His Thr Ala Glu Leu
            210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
            275                 280                 285

Glu Thr
    290

<210> SEQ ID NO 25
<211> LENGTH: 176
<212> TYPE: PRT
<213> ORGANISM: Homo sapiens
<220> FEATURE:
<221> NAME/KEY: misc_feature
<222> LOCATION: (1)..(176)
<223> OTHER INFORMATION: Human PD-L1 amino acid sequence - isoform b
      precursor

<400> SEQUENCE: 25

Met Arg Ile Phe Ala Val Phe Ile Phe Met Thr Tyr Trp His Leu Leu
1               5                   10                  15

Asn Ala Pro Tyr Asn Lys Ile Asn Gln Arg Ile Leu Val Val Asp Pro
                20                  25                  30

Val Thr Ser Glu His Glu Leu Thr Cys Gln Ala Glu Gly Tyr Pro Lys
            35                  40                  45

Ala Glu Val Ile Trp Thr Ser Ser Asp His Gln Val Leu Ser Gly Lys
        50                  55                  60

Thr Thr Thr Thr Asn Ser Lys Arg Glu Glu Lys Leu Phe Asn Val Thr
65                  70                  75                  80

Ser Thr Leu Arg Ile Asn Thr Thr Thr Asn Glu Ile Phe Tyr Cys Thr
                85                  90                  95

Phe Arg Arg Leu Asp Pro Glu Glu Asn His Thr Ala Glu Leu Val Ile
                100                 105                 110

Pro Glu Leu Pro Leu Ala His Pro Pro Asn Glu Arg Thr His Leu Val
            115                 120                 125

Ile Leu Gly Ala Ile Leu Leu Cys Leu Gly Val Ala Leu Thr Phe Ile
        130                 135                 140

Phe Arg Leu Arg Lys Gly Arg Met Met Asp Val Lys Lys Cys Gly Ile
145                 150                 155                 160

Gln Asp Thr Asn Ser Lys Lys Gln Ser Asp Thr His Leu Glu Glu Thr
                165                 170                 175

<210> SEQ ID NO 26
<211> LENGTH: 378
```

```
<212> TYPE: PRT
<213> ORGANISM: Homo sapiens
<220> FEATURE:
<221> NAME/KEY: misc_feature
<222> LOCATION: (1)..(378)
<223> OTHER INFORMATION: Human TIM-4 amino acid sequence - isoform 1

<400> SEQUENCE: 26
```

Met Ser Lys Glu Pro Leu Ile Leu Trp Leu Met Ile Glu Phe Trp Trp
1               5                   10                  15

Leu Tyr Leu Thr Pro Val Thr Ser Glu Thr Val Val Thr Glu Val Leu
            20                  25                  30

Gly His Arg Val Thr Leu Pro Cys Leu Tyr Ser Ser Trp Ser His Asn
        35                  40                  45

Ser Asn Ser Met Cys Trp Gly Lys Asp Gln Cys Pro Tyr Ser Gly Cys
50                  55                  60

Lys Glu Ala Leu Ile Arg Thr Asp Gly Met Arg Val Thr Ser Arg Lys
65                  70                  75                  80

Ser Ala Lys Tyr Arg Leu Gln Gly Thr Ile Pro Arg Gly Asp Val Ser
                85                  90                  95

Leu Thr Ile Leu Asn Pro Ser Glu Ser Asp Ser Gly Val Tyr Cys Cys
            100                 105                 110

Arg Ile Glu Val Pro Gly Trp Phe Asn Asp Val Lys Ile Asn Val Arg
        115                 120                 125

Leu Asn Leu Gln Arg Ala Ser Thr Thr Thr His Arg Thr Ala Thr Thr
130                 135                 140

Thr Thr Arg Arg Thr Thr Thr Thr Ser Pro Thr Thr Thr Arg Gln Met
145                 150                 155                 160

Thr Thr Thr Pro Ala Ala Leu Pro Thr Thr Val Val Thr Thr Pro Asp
                165                 170                 175

Leu Thr Thr Gly Thr Pro Leu Gln Met Thr Thr Ile Ala Val Phe Thr
            180                 185                 190

Thr Ala Asn Thr Cys Leu Ser Leu Thr Pro Ser Thr Leu Pro Glu Glu
        195                 200                 205

Ala Thr Gly Leu Leu Thr Pro Glu Pro Ser Lys Glu Gly Pro Ile Leu
210                 215                 220

Thr Ala Glu Ser Glu Thr Val Leu Pro Ser Asp Ser Trp Ser Ser Val
225                 230                 235                 240

Glu Ser Thr Ser Ala Asp Thr Val Leu Leu Thr Ser Lys Glu Ser Lys
                245                 250                 255

Val Trp Asp Leu Pro Ser Thr Ser His Val Ser Met Trp Lys Thr Ser
            260                 265                 270

Asp Ser Val Ser Ser Pro Gln Pro Gly Ala Ser Asp Thr Ala Val Pro
        275                 280                 285

Glu Gln Asn Lys Thr Thr Lys Thr Gly Gln Met Asp Gly Ile Pro Met
290                 295                 300

Ser Met Lys Asn Glu Met Pro Ile Ser Gln Leu Leu Met Ile Ile Ala
305                 310                 315                 320

Pro Ser Leu Gly Phe Val Leu Phe Ala Leu Phe Val Ala Phe Leu Leu
                325                 330                 335

Arg Gly Lys Leu Met Glu Thr Tyr Cys Ser Gln Lys His Thr Arg Leu
            340                 345                 350

Asp Tyr Ile Gly Asp Ser Lys Asn Val Leu Asn Asp Val Gln His Gly
        355                 360                 365

Arg Glu Asp Glu Asp Gly Leu Phe Thr Leu

<210> SEQ ID NO 27
<211> LENGTH: 1374
<212> TYPE: DNA
<213> ORGANISM: Homo sapiens
<220> FEATURE:
<221> NAME/KEY: misc_feature
<222> LOCATION: (1)..(1374)
<223> OTHER INFORMATION: Homo sapiens T-cell (TIMD4), transcript variant 1, mRNA

<400> SEQUENCE: 27

```
ataagaggtt gggctttgga tagatagaca gactcctggg tccggtcaac cgtcaaaatg      60
tccaaagaac ctctcattct ctggctgatg attgagtttt ggtggcttta cctgacacca     120
gtcacttcag agactgttgt gacggaggtt ttgggtcacc gggtgacttt gccctgtctg     180
tactcatcct ggtctcacaa cagcaacagc atgtgctggg ggaagaccca gtgcccctac     240
tccggttgca aggaggcgct catccgcact gatggaatga gggtgacctc aagaaagtca     300
gcaaaatata gacttcaggg gactatcccg agaggtgatg tctccttgac catcttaaac     360
cccagtgaaa gtgacagcgg tgtgtactgc tgccgcatag aagtgcctgg ctggttcaac     420
gatgtaaaga taaacgtgcg cctgaatcta cagagagcct caacaaccac gcacagaaca     480
gcaaccacca ccacacgcag aacaacaaca acaagcccca ccaccaccg acaaatgaca     540
acaaccccag ctgcacttcc aacaacagtc gtgaccacac ccgatctcac aaccggaaca     600
ccactccaga tgacaaccat tgccgtcttc acaacagcaa acgtgcct ttcactaacc      660
ccaagcaccc ttccggagga agccacaggt cttctgactc ccgagccttc taaggaaggg     720
cccatcctca ctgcagaatc agaaactgtc ctccccagtg attcctggag tagtgttgag     780
tctacttctg ctgacactgt cctgctgaca tccaaagagt ccaagtttg ggatctccca      840
tcaacatccc acgtgtcaat gtggaaaacg agtgattctg tgtcttctcc tcagcctgga     900
gcatctgata cagcagttcc tgagcagaac aaaacaacaa aaacaggaca gatggatgga     960
atacccatgt caatgaagaa tgaaatgccc atctcccaac tactgatgat catcgccccc    1020
tccttgggat ttgtgctctt cgcattgttt gtggcgtttc cctgagagg gaaactcatg    1080
gaaacctatt gttcgcagaa acacacaagg ctagactaca ttggagatag taaaaatgtc    1140
ctcaatgacg tgcagcatgg aagggaagac gaagacggcc tttttaccct ctaacaacgc    1200
agtagcatgt tagattgagg atgggggcat gacactccag tgtcaaaata agtcttagta    1260
gatttccttg tttcataaaa aagactcact tattccatgg atgtcattga tccaggcttg    1320
ctttagtttc atgaatgaag ggtactttag agaccacaac ttctctgtca aaaa          1374
```

<210> SEQ ID NO 28
<211> LENGTH: 350
<212> TYPE: PRT
<213> ORGANISM: Homo sapiens
<220> FEATURE:
<221> NAME/KEY: misc_feature
<222> LOCATION: (1)..(350)
<223> OTHER INFORMATION: Human TIM-4 amino acid sequence isoform 2

<400> SEQUENCE: 28

Met Ser Lys Glu Pro Leu Ile Leu Trp Leu Met Ile Glu Phe Trp Trp
1               5                   10                  15

Leu Tyr Leu Thr Pro Val Thr Ser Glu Thr Val Val Thr Glu Val Leu
            20                  25                  30

Gly His Arg Val Thr Leu Pro Cys Leu Tyr Ser Ser Trp Ser His Asn
             35                  40                  45

Ser Asn Ser Met Cys Trp Gly Lys Asp Gln Cys Pro Tyr Ser Gly Cys
 50                  55                  60

Lys Glu Ala Leu Ile Arg Thr Asp Gly Met Arg Val Thr Ser Arg Lys
 65                  70                  75                  80

Ser Ala Lys Tyr Arg Leu Gln Gly Thr Ile Pro Arg Gly Asp Val Ser
                 85                  90                  95

Leu Thr Ile Leu Asn Pro Ser Glu Ser Asp Ser Gly Val Tyr Cys Cys
            100                 105                 110

Arg Ile Glu Val Pro Gly Trp Phe Asn Asp Val Lys Ile Asn Val Arg
            115                 120                 125

Leu Asn Leu Gln Arg Ala Ser Thr Thr Thr His Arg Thr Ala Thr Thr
130                 135                 140

Thr Thr Arg Arg Thr Thr Thr Ser Pro Thr Thr Arg Gln Met
145                 150                 155                 160

Thr Thr Thr Pro Ala Ala Leu Pro Thr Thr Val Val Thr Pro Asp
                165                 170                 175

Leu Thr Thr Gly Thr Pro Leu Gln Met Thr Thr Ile Ala Val Phe Thr
            180                 185                 190

Thr Ala Asn Thr Cys Leu Ser Leu Thr Pro Ser Thr Leu Pro Glu Glu
            195                 200                 205

Ala Thr Gly Leu Leu Thr Pro Glu Pro Ser Lys Glu Gly Pro Ile Leu
210                 215                 220

Thr Ala Glu Ser Glu Thr Val Leu Pro Ser Asp Ser Trp Ser Ser Val
225                 230                 235                 240

Glu Ser Thr Ser Ala Asp Thr Val Leu Leu Thr Ser Lys Ala Ser Asp
                245                 250                 255

Thr Ala Val Pro Glu Gln Asn Lys Thr Thr Lys Thr Gly Gln Met Asp
            260                 265                 270

Gly Ile Pro Met Ser Met Lys Asn Glu Met Pro Ile Ser Gln Leu Leu
            275                 280                 285

Met Ile Ile Ala Pro Ser Leu Gly Phe Val Leu Phe Ala Leu Phe Val
290                 295                 300

Ala Phe Leu Leu Arg Gly Lys Leu Met Glu Thr Tyr Cys Ser Gln Lys
305                 310                 315                 320

His Thr Arg Leu Asp Tyr Ile Gly Asp Ser Lys Asn Val Leu Asn Asp
                325                 330                 335

Val Gln His Gly Arg Glu Asp Glu Asp Gly Leu Phe Thr Leu
            340                 345                 350

<210> SEQ ID NO 29
<211> LENGTH: 1290
<212> TYPE: DNA
<213> ORGANISM: Homo sapiens
<220> FEATURE:
<221> NAME/KEY: misc_feature
<222> LOCATION: (1)..(1290)
<223> OTHER INFORMATION: Homo sapiens T-cell (TIMD4), transcript variant
      2, mRNA

<400> SEQUENCE: 29
ataagaggtt gggctttgga tagatagaca gactcctggg tccggtcaac cgtcaaaatg    60
tccaaagaac ctctcattct ctggctgatg attgagtttt ggtggcttta cctgacacca   120
gtcacttcag agactgttgt gacggaggtt ttgggtcacc gggtgacttt gccctgtctg   180

```
tactcatcct ggtctcacaa cagcaacagc atgtgctggg ggaaagacca gtgcccctac      240
tccggttgca aggaggcgct catccgcact gatggaatga gggtgacctc aagaaagtca      300
gcaaaatata gacttcaggg gactatcccg agaggtgatg tctccttgac catcttaaac      360
cccagtgaaa gtgacagcgg tgtgtactgc tgccgcatag aagtgcctgg ctggttcaac      420
gatgtaaaga taaacgtgcg cctgaatcta cagagagcct caacaaccac gcacagaaca      480
gcaaccacca ccacacgcag aacaacaaca caagccccca ccaccaccg acaaatgaca        540 acaaccccag ctgcacttcc aacaacagtc gtgaccacac ccgatctcac aaccggaaca      600
ccactccaga tgacaaccat tgccgtcttc acaacagcaa acacgtgcct ttcactaacc      660
ccaagcaccc ttccggagga agccacaggt cttctgactc ccgagccttc taaggaaggg      720
cccatcctca ctgcagaatc agaaactgtc ctccccagtg attcctggag tagtgttgag      780
tctacttctg ctgacactgt cctgctgaca tccaaagcat ctgatacagc agttcctgag      840
cagaacaaaa caacaaaaac aggacagatg gatggaatac ccatgtcaat gaagaatgaa      900
atgcccatct cccaactact gatgatcatc gcccctcct tgggatttgt gctcttcgca       960
ttgtttgtgg cgtttctcct gagagggaaa ctcatggaaa cctattgttc gcagaaacac     1020
acaaggctag actacattgg agatagtaaa aatgtcctca atgacgtgca gcatggaagg     1080
gaagacgaag acggcctttt taccctctaa caacgcagta gcatgttaga ttgaggatgg     1140
gggcatgaca ctccagtgtc aaaataagtc ttagtagatt tccttgtttc ataaaaaaga     1200
ctcacttatt ccatggatgt cattgatcca ggcttgcttt agtttcatga atgaagggta     1260
ctttagagac acaacttct ctgtcaaaaa                                        1290
```

<210> SEQ ID NO 30  
<211> LENGTH: 377  
<212> TYPE: PRT  
<213> ORGANISM: Macaca fascicularis  
<220> FEATURE:  
<221> NAME/KEY: misc_feature  
<222> LOCATION: (1)..(377)  
<223> OTHER INFORMATION: TIM-4 ortholog

<400> SEQUENCE: 30

```
Met Ser Lys Glu Pro Leu Ile Leu Trp Leu Val Met Glu Phe Trp Trp
1               5                   10                  15

Leu Tyr Leu Thr Pro Val Thr Ser Glu Thr Val Thr Glu Val Leu
            20                  25                  30

Gly His Arg Val Thr Leu Pro Cys Leu Tyr Ser Ser Trp Ser Gln Asn
        35                  40                  45

Ser Asn Ser Met Cys Trp Gly Lys Asp Lys Cys Pro Tyr Ser Gly Cys
    50                  55                  60

Lys Glu Ala Leu Ile Arg Thr Asp Gly Thr Val Thr Ser Arg Lys
65                  70                  75                  80

Ser Ala Lys Tyr Arg Leu Pro Gly Thr Ile Gln Arg Gly Asn Val Ser
                85                  90                  95

Leu Thr Ile Leu Asn Pro Arg Glu Gly Asp Ser Gly Val Tyr Cys Cys
            100                 105                 110

Arg Ile Glu Val Pro Gly Trp Phe Asn Asp Val Lys Ile Asn Val Arg
        115                 120                 125

Leu Asn Leu Gln Arg Glu Thr Cys Leu Leu Leu Val Thr Ala Ser Thr
    130                 135                 140

Thr Thr Arg Arg Thr Arg Thr Thr Ser Pro Pro Thr Thr Pro His Val
145                 150                 155                 160
```

```
Thr Thr Thr Arg Ala Ala Leu Pro Thr Thr Val Met Thr Thr Pro Asp
            165                 170                 175

Leu Thr Thr Glu Thr Pro Leu Gln Thr Thr Thr Ala Val Phe Thr
        180                 185                 190

Thr Ala Asn Thr Cys Pro Ser Pro Thr Pro Ser Thr Leu Pro Glu Ala
            195                 200                 205

Ala Thr Gly Leu Leu Thr Pro Glu Pro Ser Lys Glu Gly Pro Ile Leu
        210                 215                 220

Thr Ala Glu Ser Glu Pro Val Leu Pro Ser Asp Ser Trp Ser Ser Thr
225                 230                 235                 240

Glu Ser Pro Ala Asp Thr Val Leu Leu Thr Ser Arg Glu Ser Lys Val
            245                 250                 255

Trp Asp Leu Pro Pro Thr Ser His Val Ser Met Trp Lys Thr Ser Asp
            260                 265                 270

Ser Val Ser Ser Pro Gln Pro Gly Ala Ser Asp Thr Ala Val Pro Glu
        275                 280                 285

Gln Asn Lys Thr Thr Lys Thr Gly Gln Met Asp Gly Met Pro Met Pro
        290                 295                 300

Met Lys Asn Glu Met Pro Ile Ser Gln Leu Leu Met Ile Leu Ala Pro
305                 310                 315                 320

Ser Leu Gly Phe Val Leu Leu Ala Leu Leu Met Ala Phe Leu Leu Arg
            325                 330                 335

Gly Lys Leu Met Glu Thr Asn Cys Leu Gln Lys His Thr Arg Leu Asp
            340                 345                 350

Cys Ile Gly Asp Ser Lys Asn Val Leu Asn Asp Met Arg His Gly Arg
            355                 360                 365

Glu Asp Glu Asp Gly Leu Phe Thr Leu
        370                 375

<210> SEQ ID NO 31
<211> LENGTH: 369
<212> TYPE: PRT
<213> ORGANISM: Macaca fascicularis
<220> FEATURE:
<221> NAME/KEY: misc_feature
<222> LOCATION: (1)..(369)
<223> OTHER INFORMATION: TIM-4 ortholog

<400> SEQUENCE: 31

Met Ser Lys Glu Pro Leu Ile Leu Trp Leu Val Met Glu Phe Trp Trp
1               5                   10                  15

Leu Tyr Leu Thr Pro Val Thr Ser Glu Thr Val Val Thr Glu Val Leu
            20                  25                  30

Gly His Arg Val Thr Leu Pro Cys Leu Tyr Ser Ser Trp Ser Gln Asn
        35                  40                  45

Ser Asn Ser Met Cys Trp Gly Lys Asp Lys Cys Pro Tyr Ser Gly Cys
50                  55                  60

Lys Glu Ala Leu Ile Arg Thr Asp Gly Thr Arg Val Thr Ser Arg Lys
65                  70                  75                  80

Ser Ala Lys Tyr Arg Leu Pro Gly Thr Ile Gln Arg Gly Asn Val Ser
            85                  90                  95

Leu Thr Ile Leu Asn Pro Arg Glu Gly Asp Ser Gly Val Tyr Cys Cys
        100                 105                 110

Arg Ile Glu Val Pro Gly Trp Phe Asn Asp Val Lys Ile Asn Val Arg
        115                 120                 125
```

```
Leu Asn Leu Gln Arg Ala Ser Thr Thr Thr Arg Arg Thr Arg Thr Thr
130                 135                 140

Ser Pro Pro Thr Thr Pro His Val Thr Thr Arg Ala Ala Leu Pro
145                 150                 155                 160

Thr Thr Val Met Thr Thr Pro Asp Leu Thr Thr Glu Thr Pro Leu Gln
                165                 170                 175

Thr Thr Thr Thr Ala Val Phe Thr Thr Ala Asn Thr Cys Pro Ser Pro
            180                 185                 190

Thr Pro Ser Thr Leu Pro Glu Ala Ala Thr Gly Leu Leu Thr Pro Glu
        195                 200                 205

Pro Ser Lys Glu Gly Pro Ile Leu Thr Ala Glu Ser Glu Pro Val Leu
210                 215                 220

Pro Ser Asp Ser Trp Asn Ser Thr Glu Ser Pro Ala Asp Thr Val Leu
225                 230                 235                 240

Leu Thr Ser Arg Glu Ser Lys Val Trp Asp Leu Pro Pro Thr Ser His
                245                 250                 255

Val Ser Met Trp Thr Thr Ser Asp Ser Val Ser Ser Pro Gln Pro Gly
                260                 265                 270

Ala Ser Asp Thr Ala Val Pro Glu Gln Asn Lys Thr Thr Lys Thr Gly
            275                 280                 285

Gln Met Asp Gly Met Pro Met Pro Met Lys Asn Glu Met Pro Ile Ser
290                 295                 300

Gln Leu Leu Met Ile Leu Ala Pro Ser Leu Gly Phe Val Leu Leu Ala
305                 310                 315                 320

Leu Leu Met Ala Phe Leu Leu Arg Gly Lys Leu Met Glu Thr Asn Cys
                325                 330                 335

Leu Gln Lys His Thr Arg Leu Asp Cys Ile Gly Asp Ser Lys Asn Val
                340                 345                 350

Leu Asn Asp Met Arg His Gly Arg Glu Asp Glu Asp Gly Leu Phe Thr
                355                 360                 365

Leu

<210> SEQ ID NO 32
<211> LENGTH: 343
<212> TYPE: PRT
<213> ORGANISM: Mus musculus
<220> FEATURE:
<221> NAME/KEY: misc_feature
<222> LOCATION: (1)..(343)
<223> OTHER INFORMATION: TIM-4 ortholog

<400> SEQUENCE: 32

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
                100                 105                 110
```

```
Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr
        130                 135             140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
        210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ile Ala Cys Cys Val Gly
            275                 280                 285

Phe Val Leu Met Val Leu Leu Phe Leu Ala Phe Leu Leu Arg Gly Lys
        290                 295                 300

Val Thr Gly Ala Asn Cys Leu Gln Arg His Lys Arg Pro Asp Asn Thr
305                 310                 315                 320

Glu Asp Ser Asp Ser Val Leu Asn Asp Met Ser His Gly Arg Asp Asp
                325                 330                 335

Glu Asp Gly Ile Phe Thr Leu
            340
```

COMBINATION OF TIM-4 ANTAGONIST AND PD-1 ANTAGONIST AND METHODS OF USE

CROSS-REFERENCE TO RELATED APPLICATIONS

This application is a divisional of U.S. patent application Ser. No. 16/314,732, filed Jan. 2, 2019, which is a 35 U.S.C. 371 national stage filing of International Application No. PCT/US2017/040665, filed Jul. 5, 2017, which claims priority to U.S. Provisional Application No. 62/359,073, filed Jul. 6, 2016. The contents of the aforementioned applications are hereby incorporated by reference.

SEQUENCE LISTING

The instant application contains a Sequence Listing which has been submitted via EFS-Web and is hereby incorporated by reference in its entirety. Said ASCII copy, created on Mar. 14, 2022, is named Sequence_Listing_MXI_550USDV.txt and is 45,407 bytes in size.

BACKGROUND

The National Cancer Institute has estimated that in the United States alone, 1 in 3 people will be struck with cancer during their lifetime. Moreover, approximately 50% to 60% of people contracting cancer will eventually succumb to the disease. Once tumor cells escape from the primary site they passage through the lymphatic and/or circulatory system and ultimately a few establish at distant sites to give metastases, and 95% of deaths from solid tumors in the developed world are due to metastasis.

The widespread occurrence of cancer tumors underscores the need for improved anticancer regimens. However, despite advances in multimodal therapy, increases in overall survival in cancer patients have been limited. Accordingly, it is an object of the present invention to provide improved methods for treating subjects with such tumors.

SUMMARY OF THE INVENTION

The present inventors have discovered for the first time that co-administration of a TIM-4 antagonist (e.g., an antibody) and an anti-PD-1 antagonist (e.g., an antibody) effectively inhibits tumor growth in vivo, even synergistically. Accordingly, it is an object of the present invention to provide improved methods for treating subjects with cancer. Specifically, it is an object of the invention to provide efficacious combination treatment regimens wherein a TIM-4 antagonist is combined with an anti-PD-1 antagonist for the treatment of cancer.

In one aspect, the present invention provides a method for the treatment of cancer in a subject by co-administering an effective amount of a PD-1 antagonist and a TIM-4 antagonist.

Suitable TIM-4 antagonists for use in the methods of the invention, include, without limitation, ligands, antibodies (e.g., monoclonal antibodies and bispecific antibodies) and multivalent agents. The TIM-4 antagonist can be a non-activating ligand or ligand binding partner (e.g., a small molecule, engineered PS emulator or soluble TIM-1, or other binding protein). In one embodiment, the TIM-4 antagonist is an anti-TIM4 antibody. In one embodiment, the TIM-4 antagonist is an antibody which binds to an epitope within the IgV domain of TIM-4. In another embodiment, the TIM-4 antagonist is an antibody such as 9F4, RMT4-53, RMT4-54, F31-563 or 21T112.

An exemplary anti-TIM-4 antibody contains heavy and light chains comprising the heavy and light chain CDRs of 9F4, RMT4-53, RMT4-54, F31-563 or 21T112, and optionally comprises a framework region with at least about 90% amino acid sequence identity with the framework region of the corresponding antibody. Anti-TIM-4 antibodies may also comprise heavy and light chain variable domains that are at least about 90%, 95% or 99% identical with that of antibody 9F4, RMT4-53, RMT4-54, F31-563 or 21T112. In certain embodiments, the anti-TIM-4 antagonist antibody competes for binding with, and/or binds to the same epitope on TIM-4 as, 9F4, RMT4-53, RMT4-54, F31-563 or 21T112.

Suitable PD-1 antagonists for use in the methods of the invention, include, without limitation, ligands, antibodies (e.g., monoclonal antibodies and bispecific antibodies), and multivalent agents. In one embodiment, the PD-1 antagonist is an anti-PD-1 or anti-PD-L1 antibody. In another embodiment, the PD-1 antagonist is an antibody, such as MK-3475 or CT-011. In one embodiment, the PD-1 antagonist is a fusion protein, e.g., an Fc fusion protein, such as AMP-244.

An exemplary anti-PD-1 antibody is 5C4 (referred to as 5C4 in WO 2006/121168; also known as MDX-1106, ONO-4538, and nivolumab) comprising heavy and light chains having the sequences shown in SEQ ID NOs: 11 and 12, respectively, or antigen binding fragments and variants thereof. In other embodiments, the antibody comprises the heavy and light chain CDRs or variable regions (VRs) of 5C4. Accordingly, in one embodiment, the antibody comprises the CDR1, CDR2, and CDR3 domains of the VH region of 5C4 having the sequence shown in SEQ ID NO: 13, and the CDR1, CDR2 and CDR3 domains of the VL region of 5C4 having the sequence shown in SEQ ID NO:15. In another embodiment, the antibody comprises the heavy chain CDR1, CDR2 and CDR3 domains having the sequences set forth in SEQ ID NOs: 17, 18, and 19, respectively, and the light chain CDR1, CDR2 and CDR3 domains having the sequences set forth in SEQ ID NOs: 20, 21, and 22, respectively.

In another embodiment, the antibody comprises VH and/or VL regions having the amino acid sequences set forth in SEQ ID NO: 13 and/or SEQ ID NO: 15, respectively. In another embodiment, the antibody comprises the heavy chain variable (VH) and/or light chain variable (VL) regions encoded by the nucleic acid sequences set forth in SEQ ID NO: 14 and/or SEQ ID NO: 16, respectively. In another embodiment, the antibody competes for binding with, and/or binds to the same epitope on PD-1 as, the above-mentioned antibodies. In another embodiment, the antibody has at least about 90% variable region amino acid sequence identity with the above-mentioned antibodies (e.g., at least about 90%, 95% or 99% variable region identity with SEQ ID NO: 13 or SEQ ID NO: 15).

In one embodiment, the PD-1 antagonist is an anti-PD-L1 antibody, such as MEDI4736 (also known as Anti-B7-H1) or MPDL3280A (also known as RG7446). An exemplary anti-PD-L1 antibody is 12A4 (referred to as 12A4 in WO 2007/005874 and U.S. Pat. No. 7,943,743). In one embodiment, the antibody comprises the heavy and light chain CDRs or VRs of 12A4. Accordingly, in one embodiment, the antibody comprises the CDR1, CDR2, and CDR3 domains of the VH region of 12A4 having the sequence shown in SEQ ID NO: 1, and the CDR1, CDR2 and CDR3 domains of the VL region of 12A4 having the sequence shown in SEQ ID NO: 3. In another embodiment, the antibody comprises the heavy chain CDR1, CDR2 and CDR3 domains having the sequences set forth in SEQ ID NOs: 5, 6, and 7, respectively, and the light chain CDR1, CDR2 and CDR3 domains having the sequences set forth in SEQ ID NOs: 8, 9, and 10, respectively. In another embodiment, the antibody comprises VH and/or VL regions having the amino acid sequences set forth in SEQ ID NO: 1 and/or SEQ ID NO: 3, respectively. In another embodiment, the antibody comprises the heavy chain variable (VH) and/or light chain variable (VL) regions encoded by the nucleic acid sequences set forth in SEQ ID NO: 2 and/or SEQ ID NO: 4, respectively. In another embodiment, the antibody competes for binding with, and/or binds to the same epitope on PD-L1 as, the above-mentioned antibodies. In another embodiment, the antibody has at least about 90% variable region amino acid sequence identity with the above-mentioned antibodies (e.g., at least about 90%, 95% or 99% variable region identity with SEQ ID NO: 1 or SEQ ID NO: 3).

In one embodiment, the invention provides a method of treating cancer in a subject, the method comprising administering to the subject an effective amount of a PD-1 antagonist and a TIM-4 antagonist, wherein
(a) the PD-1 antagonist is an anti-PD-1 antibody comprising the CDR1, CDR2 and CDR3 domains in a heavy chain variable region having the sequence set forth in SEQ ID NO: 13, and the CDR1, CDR2 and CDR3 domains in a light chain variable region having the sequence set forth in SEQ ID NO: 15; and
(b) the TIM-4 antagonist is an antibody.

In another embodiment, the invention provides a method of treating cancer in a subject, the method comprising administering to the subject an effective amount of a PD-1 antagonist and a TIM-4 antagonist, wherein
(a) the PD-1 antagonist is an anti-PD-L1 antibody comprising the CDR1, CDR2 and CDR3 domains in a heavy chain variable region having the sequence set forth in SEQ ID NO: 1, and the CDR1, CDR2 and CDR3 domains in a light chain variable region having the sequence set forth in SEQ ID NO: 3; and
(b) the TIM-4 antagonist is an antibody.

The efficacy of the treatment methods provided herein can be assessed using any suitable means. In one embodiment, the treatment produces at least one therapeutic effect selected from the group consisting of reduction in size of a tumor, reduction in number of metastasic lesions over time, complete response, partial response, and stable disease. In another embodiment, administration of a PD-1 antagonist and a TIM-4 antagonist results in at least a 1, 1.25, 1.50, 1.75, 2, 2.25, 2.50, 2.75, 3, 3.25, 3.5, 3.75, or 4-fold reduction in tumor volume, e.g., relative to treatment with the PD-1 antagonist or TIM-4 antagonist alone, or relative to tumor volume before initiation of treatment. In another embodiment, administration of the PD-1 antagonist and TIM-4 antagonist results in at least a 1-fold, 2-fold, or more preferably a 3-fold reduction in tumor volume, e.g., relative to treatment with the PD-1 antagonist or TIM-4 antagonist alone, or relative to tumor volume before initiation of treatment. In a further embodiment, administration of a PD-1 antagonist and a TIM-4 antagonist results in tumor growth inhibition of at least 50%, 60%, 70% or 80%, e.g., relative to treatment with the PD-1 antagonist or TIM-4 antagonist alone, or relative to tumor volume before initiation of treatment. In certain embodiments, tumor volume is reduced by 50%, 60%, 70%, 80%, 90% or more, e.g., relative to tumor size before initiation of the treatment.

The PD-1 antagonist and TIM-4 antagonist can be administered accordingly to a suitable dosage, route (e.g., intravenous, intraperitoneal, intramuscular, intrathecal or subcutaneous). The antagonist and agonist can also be administered according to any suitable schedule. For example, the antagonist and agonist can be simultaneously administered in a single formulation. Alternatively, the antagonist and agonist can be formulated for separate administration, wherein they are administered concurrently or sequentially. In one embodiment, the PD-1 antagonist is administered prior to administration of the TIM-4 antagonist. In another embodiment, the TIM-4 antagonist is administered prior to administration of the PD-1 antagonist. In a further embodiment, the TIM-4 antagonist and the PD-1 antagonist are administered simultaneously.

In one embodiment, the cancer is a cancer selected from the group consisting of carcinoma, sarcoma, blastoma, lymphoma and leukemia. In one embodiment, the cancer is selected from the group consisting of small-cell lung cancer, non-small cell lung cancer, gastrointestinal cancer, colorectal cancer, stomach cancer, colon carcinoma, and glioblastoma. In another embodiment, the cancer is selected from the group consisting of chronic myeloid leukemia, acute lymphoblastic leukemia, Philadelphia chromosome positive acute lymphoblastic leukemia (Ph+ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, acute myelogenous leukemia (AML), and chronic lymphocytic leukemia (CML).

Additional agents and therapies can be administered in combination with the agonists and antagonists described herein. In one embodiment, the methods comprise administration of an additional therapeutic agent (e.g., a cyotoxin or chemotherapeutic agent.

Also provided herein are compositions comprising a PD-1 antagonist and a TIM-4 antagonist. In one embodiment, the antagonist is a ligand, antibody (e.g., monoclonal antibody or bispecific antibody) or multivalent agent. In another embodiment, the PD-1 antagonist is an anti-PD-1 antibody comprising the heavy and light chain CDRs or VRs of 5C4. In another embodiment, the PD-1 antagonist is an anti-PD-L1 antibody comprising the heavy and light chain CDRs or VRs of 12A4.

Further provided are kits for treating a cancer in a subject, the kit comprising:
(a) a dose of a PD-1 antagonist;
(b) a dose of a TIM-4 antagonist; and
(c) instructions for using the PD-1 antagonist and TIM-4 antagonist in the methods described herein. In one embodiment, the TIM-4 antagonist is an antibody. In another embodiment, the PD-1 antagonist is an antibody. In a particular embodiment, the PD-1 antagonist is an anti-PD-1 antibody comprising the CDR1, CDR2 and CDR3 domains in a heavy chain variable region having the sequence set forth in SEQ ID NO: 13, and the CDR1, CDR2 and CDR3 domains in a light chain variable region having the sequence set forth in SEQ ID NO: 15. In another particular embodiment, the PD-1 antagonist is an anti-PD-L1 antibody comprising antibody comprises the CDR1, CDR2 and CDR3 domains in a heavy chain variable region having the sequence set forth in SEQ ID NO: 1, and the CDR1, CDR2 and CDR3 domains in a light chain variable region having the sequence set forth in SEQ ID NO: 3.

Other features and advantages of the instant disclosure will be apparent from the following detailed description and examples, which should not be construed as limiting.

BRIEF DESCRIPTION OF THE DRAWINGS

FIG. 1 depicts an alignment of the amino acid sequences of human TIM-4 isoforms 1 (SEQ ID NO: 26) and 2 (SEQ ID NO: 28).

FIG. 2 depicts the alignment of the amino acid sequences of cynomologous monkey (SEQ ID NOS; 30-31), mouse (SEQ ID NO: 32) and human (SEQ ID NO: 26) TIM-4 orthologs.

FIG. 4A-F are graphs depicting the CD8+ cell populations in spleen and tumors from mice after administration of a control, an TIM-4 antagonist antibody, an anti-PD-1 antibody, or a combination of an anti-PD-1 antibody and an anti-TIM-4 antibody.

FIG. 5A-F are graphs depicting the CD4+ populations in spleen and tumors from mice after administration of a control, an TIM-4 antagonist antibody, an anti-PD-1 antibody, or a combination of an anti-PD-1 antibody and an anti-TIM-4 antibody.

DETAILED DESCRIPTION OF THE INVENTION

Figure 3A:
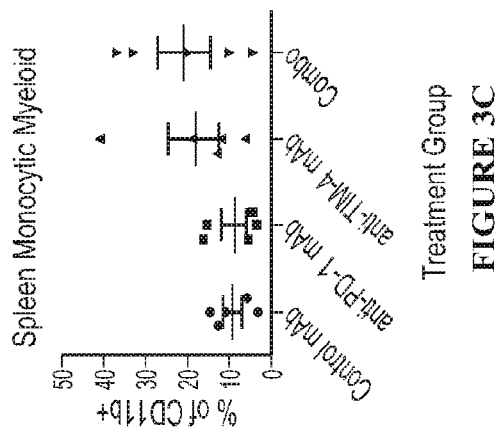
FIG. 3A-F are graphs depicting the myeloid cell populations in spleen and tumors from mice after administration of a control, a TIM-4 antagonist antibody, a PD-1 antagonist antibody, or a combination of an anti-PD-1 antibody and an anti-TIM-4 antibody.
Figure 3B:
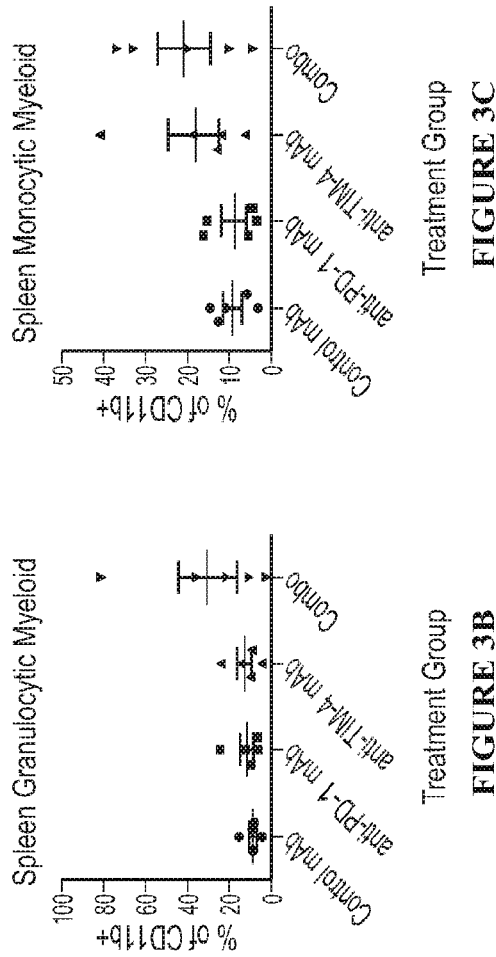
Figure 3C:
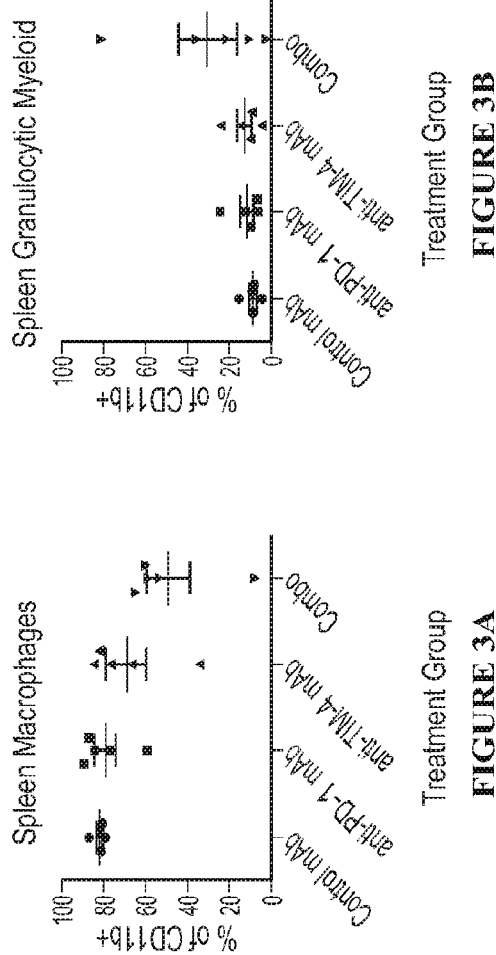
Figure 3D:
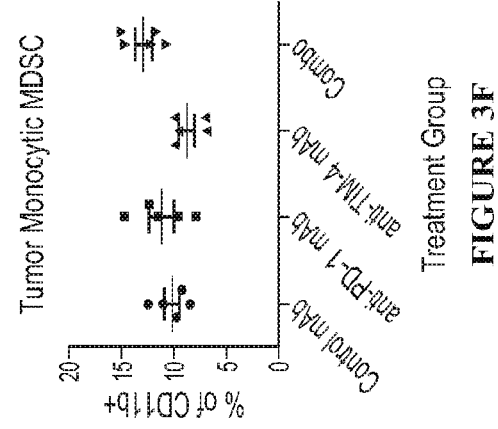
Figure 3E:
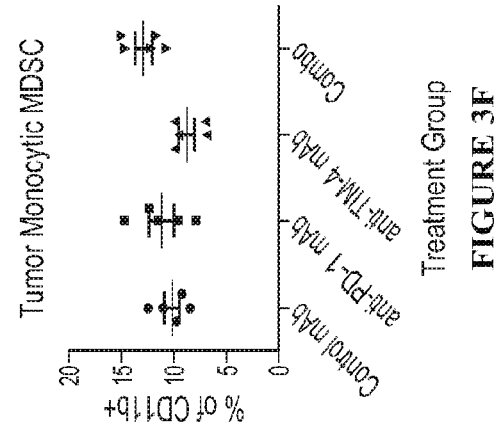
Figure 3F:
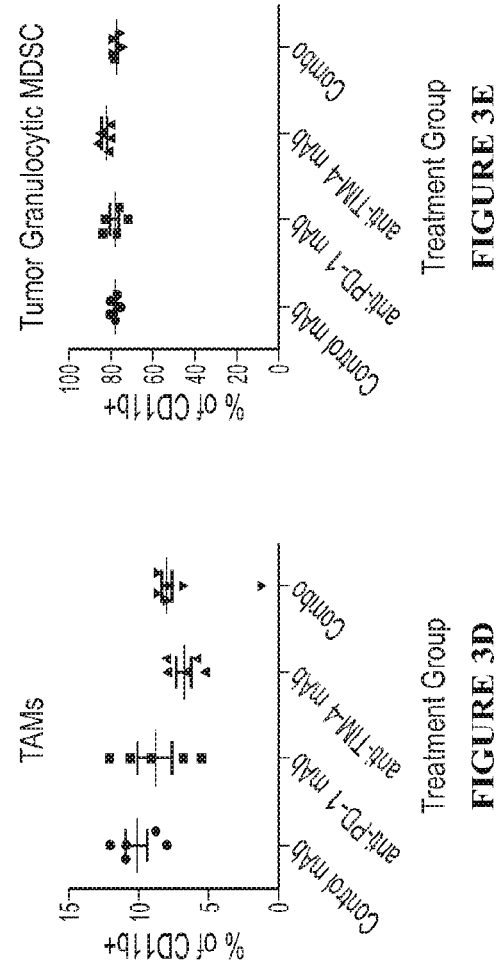
Figure 6B:
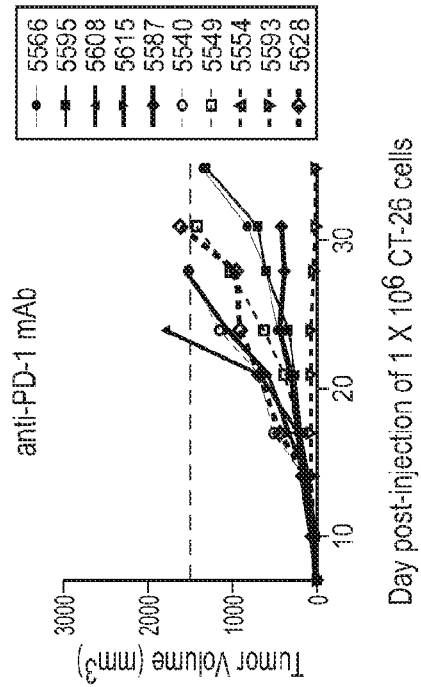
FIG. 6A-D are graphs depicting tumor volume ($mm^3$) in individual mice after administration of a control, an TIM-4 antagonist antibody, an anti-PD-1 antibody, or a combination of an anti-PD-1 antibody and an anti-TIM-4 antibody.
Figure 6D:
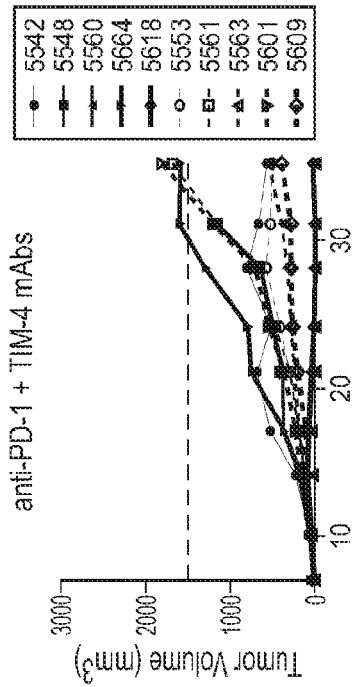
Figure 6A:
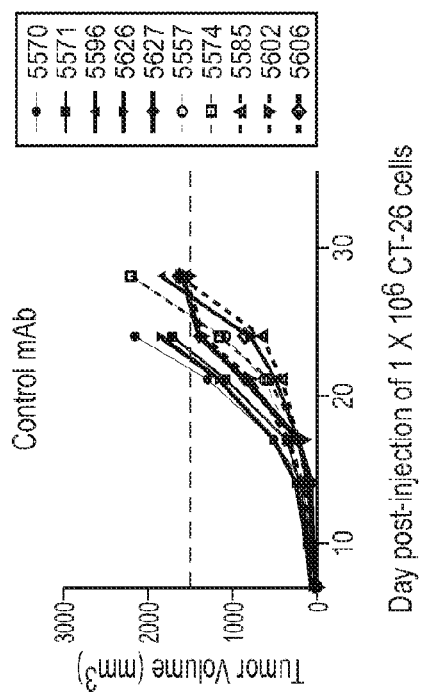
Figure 6C:
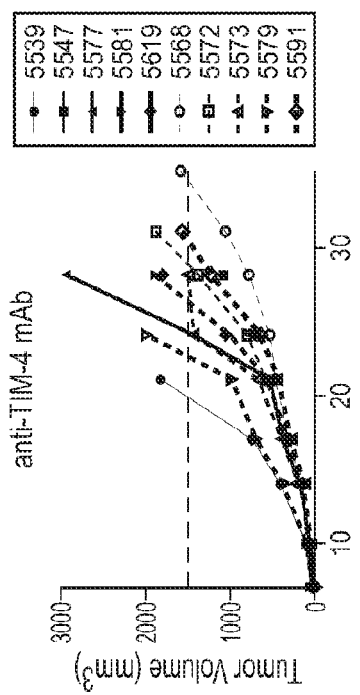

As described herein, the invention is based on the discovery that co-administration of a TIM-4 antagonist (e.g., an antibody) and a PD-1 antagonist (e.g., an antibody) effectively inhibits tumor growth in vivo, even synergistically.

Accordingly, the present invention provides a method for the treatment of cancer in a subject which comprises administering to a subject (e.g., human) an effective amount of a PD-1 antagonist and a TIM-4 antagonist.

I. Definitions

In order that the present description may be more readily understood, certain terms are first defined. Additional definitions are set forth throughout the detailed description. Unless defined otherwise, all technical and scientific terms used herein have the same meaning as commonly understood by one of ordinary skill in the art, and conventional methods of immunology, protein chemistry, biochemistry, recombinant DNA techniques and pharmacology are employed.

As used herein, the singular forms "a", "an" and "the" include plural referents unless the context clearly dictates otherwise. The use of "or" or "and" means "and/or" unless stated otherwise. Furthermore, use of the term "including" as well as other forms, such as "include", "includes", and "included", is not limiting.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods. Unless otherwise indicated, all numbers expressing quantities of ingredients, properties such as molecular weight, reaction conditions, etc., used herein are to be understood as being modified by the term "about".

As used herein, the term "subject" or "patient" are used interchangeably herein and refer to a mammal such as a human, mouse, rat, hamster, guinea pig, rabbit, cat, dog, monkey, cow, horse, pig and the like (e.g., a patient having cancer).

A "solid tumor" includes, for example, sarcoma, melanoma, carcinoma, prostate carcinoma, lung carcinoma, colon carcinoma, or other solid tumor cancer.

The terms "cancer", "cancerous", or "malignant" refer to or describe the physiological condition in mammals that is typically characterized by unregulated cell growth. As used herein, the term includes pre-malignant as well as malignant cancers. Examples of cancer include, for example, leukemia, lymphoma, blastoma, carcinoma and sarcoma. More particular examples of such cancers include chronic myeloid leukemia, acute lymphoblastic leukemia, Philadelphia chromosome positive acute lymphoblastic leukemia (Ph+ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, acute myelogenous leukemia (AML), and chronic lymphocytic leukemia (CML).

The term "carcinoma" as used herein refers to a type of cancer that develops from epithelial cells. Specifically, a carcinoma is a cancer that begins in a tissue that lines the inner or outer surfaces of the body, and that generally arises from cells originating in the endodermal or ectodermal germ layer during embryogenesis. Various subtypes of carcinomas include, adenocarcinoma (featuring microscopic glandular-related tissue cytology, tissue architecture, and/or glandrelated molecular products, e.g., mucin), squamous cell carcinoma (observable features and characteristics indicative of squamous differentiation, e.g., intercellular bridges, keratinization, squamous pearls), adenosquamous carcinoma (a mixed tumor containing both adenocarcinoma and squamous cell carcinoma, wherein each of these cell types comprise at least 10% of the tumor volume), anaplastic or undifferentiated carcinoma (a heterogeneous group of high-grade carcinomas that feature cells lacking distinct histological or cytological evidence of any of the more specifically differentiated neoplasnms), large cell carcinoma (composed of large, monotonous rounded or overtly polygonal-shaped cells with abundant cytoplasm), small cell carcinoma (cells are usually round and are less than approximately 3 times the diameter of a resting lymphocyte and little evident cytoplasm).

As used herein, the term "immune cell" refers to cells that play a role in the immune response, including lymphocytes, such as B cells and T cells; natural killer cells; myeloid cells, such as monocytes, macrophages, eosinophils, mast cells, basophils, and granulocytes.

The term "immune response" as used herein refers to a cellular immune response, including T cell mediated and/or B cell mediated immune responses such as stimulation of T lymphocytes, macrophages, and/or natural killer cells.

The terms "myeloid-derived suppressor cell" or "MDSC" are used interchangeably herein to refer to a heterogenous group of immune cells from the myeloid lineage (a family of cells that originate from bone marrow stem cells), to which dendritic cells, macrophages and neutrophils also belong. MDSCs strongly expand in pathological situations such as chronic infections and cancer, as a result of an altered hematopoiesis. MDSCs are further classified into two subtypes, monocytic MDSCs and granulocytic MDSCs. MDSC suppressor function lies in their ability to inhibit T cell proliferation and activation. For example, under chronic inflammatory conditions (viral and bacterial infections) or cancer, myeloid differentiation is skewed towards the expansion of MDSCs. These MDSCs infiltrate inflammation sites and tumors, where they inhibit immune responses by inhibiting T cells (e.g., CD8+ T cells) and NK cells, for example. MDSCs also accelerate angiogenesis, tumor progression and metastasis through the expression of cytokines and factors such as TGF-beta.

The terms "damage-associated molecular patterns" or "DAMPs" are used interchangeably herein to refer to intracellular molecules released by injured tissues. DAMPs are molecules that have a physiological role inside the cell, but acquire additional functions when exposed to the extracellular environment. For example, DAMPs alert the body about danger, stimulate an inflammatory response, and finally promote the regeneration process. Beside their passive release by dead cells, some DAMPs can be secreted or exposed by living cells undergoing a life-threatening stress. DAMPs have been linked to inflammation and related disorders. DAMPs include, but are not limited to, histones, genomic DNA, HMGB1, IL1a, IL33, ATP, F-actin, cyclophilin A, HSPs, uric acid crystals, S100s, mitochondrial DNA, mitochondrial transcription factor A, alreticulin.

The term "efferocytosis" refers to the process by which dying/dead cells (e.g., apoptotic or necrotic) are removed by phagocytic cells (e.g., neurtrophils, monocytes, macrophages, mast cells and dendritic cells). During efferocytosis, phagocytes accumulate to the sites of apoptotic cells and the cell membrane of phagocytic cells engulfs the apoptotic cell, forming a large fluid-filled vesicle, the "effersome" containing the dead cell. The effect of efferocytosis is that dead cells are removed before their membrane integrity is breached and their contents leak into the surrounding tissue. Efferocytosis triggers specific downstream intracellular signal transduction pathways, for example resulting in anti-inflammatory, anti-protease and growth-promoting effects. Conversely, impaired efferocytosis has been linked to autoimmune disease and tissue damage.

"Autophagy" or "autophagocytosis" is the natural, destructive mechanism that disassembles, through a regulated process, unnecessary or dysfunctional cellular components. Autophagy allows the orderly degradation and recycling of cellular components. During this process, targeted cytoplasmic constituents are isolated from the rest of the cell within a double-membraned vesicle known as an autophagosome. The autophagosome then fuses with a lysosome and the contents are degraded and recycled. There are three different forms of autophagy that are commonly described, namely macroautophagy, microautophagy and chaperone-mediated autophagy. In the context of disease, autophagy has been seen as an adaptive response to stress which promotes survival, whereas in other cases it appears to promote cell death and morbidity.

The terms "treat," "treating," and "treatment," as used herein, refer to any type of intervention or process performed on, or administering an active agent or combination of active agents to the subject with the objective of reversing, alleviating, ameliorating, inhibiting, or slowing down or preventing the progression, development, severity or recurrence of a symptom, complication, condition or biochemical indicia associated with a disease.

As used herein, "effective treatment" or "positive therapeutic response" refer to a treatment producing a beneficial effect, e.g., amelioration of at least one symptom of a disease or disorder, e.g., cancer. A beneficial effect can take the form of an improvement over baseline, i.e., an improvement over a measurement or observation made prior to initiation of therapy according to the method. For example, a beneficial effect can take the form of slowing, stabilizing, stopping or reversing the progression of a cancer in a subject at any clinical stage, as evidenced by a decrease or elimination of a clinical or diagnostic symptom of the disease, or of a marker of cancer. Effective treatment may, for example, decrease in tumor size, decrease the presence of circulating tumor cells, reduce or prevent metastases of a tumor, slow or arrest tumor growth and/or prevent or delay tumor recurrence or relapse.

The term "effective amount" or "therapeutically effective amount" refer to an amount of an agent or combination of agents that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In reference to solid tumors, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay tumor development. In some embodiments, an effective amount is an amount sufficient to prevent or delay tumor recurrence. An effective amount can be administered in one or more administrations. The effective amount of the drug or composition may: (i) reduce the number of cancer cells; (ii) reduce tumor size; (iii) inhibit, retard, slow to some extent and may stop cancer cell infiltration into peripheral organs; (iv) inhibit (i.e., slow to some extent and may stop tumor metastasis; (v)

inhibit tumor growth; (vi) prevent or delay occurrence and/or recurrence of tumor; and/or (vii) relieve to some extent one or more of the symptoms associated with the cancer. In one example, an "effective amount" is the amount of a PD-1 antagonist (e.g., an antibody) and TIM-4 antagonist antibody (e.g., an antibody), in combination, to effect a significant decrease in cancer or slowing of progression of cancer, such as an advanced solid tumor. An effective amount of the combination therapy is administered according to the methods described herein in an "effective regimen" which refers to a combination of the PD-1 antagonist and the TIM-4 antagonist, wherein the order of administration and dosage frequency is adequate to effect treatment.

"Optimal biologic dose (OBD)" is defined as the minimum dose of an agent or combination of agents that gives the most optimal and lasting in vivo response without clinically unacceptable toxicity. Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50.

As used herein, the terms "synergy", "therapeutic synergy", and "synergistic effect" refer to a phenomenon where treatment of patients with a combination of therapeutic agents (e.g., PD-1 antagonist in combination with TIM-4 antagonist) manifests a therapeutically superior outcome to the outcome achieved by each individual constituent of the combination used when used alone (see, e.g., T. H. Corbett et al., 1982, *Cancer Treatment Reports*, 66, 1187). In this context a therapeutically superior outcome includes one or more of the following (a) an increase in therapeutic response that is greater than the sum of the separate effects of each agent alone at the same dose as in the combination; (b) a decrease in the dose of one or more agents in the combination without a decrease in therapeutic efficacy; (c) a decrease in the incidence of adverse events while receiving a therapeutic benefit that is equal to or greater than the monotherapy of each agent at the same dose as in the combination, (d) a reduction in dose-limiting toxicities while receiving a therapeutic benefit that is greater than the monotherapy of each agent; (e) a delay or minimization of the induction of drug resistance. In xenograft models, a combination, used at its maximum tolerated dose, in which each of the constituents will be present at a dose generally not exceeding its individual maximum tolerated dose, manifests therapeutic synergy when decrease in tumor growth achieved by administration of the combination is greater than the value of the decrease in tumor growth of the best constituent when the constituent is administered alone. Synergism of a drug combination may be determined, for example, according to the combination index (CI) theorem of Chou-Talalay (Chou et al., Adv. Enzyme Regul. 1984; 22:27-55; Chou, Cancer Res. 2010; 70(2):440-446).

"Free of cancer" or "disease free" or NED (No Evidence of Disease) means that the patient has demonstrated a clinical response induced by treatment with the current standard of care therapies. By "clinical response," it is meant that the clinical signs, radiological signs, and symptoms of cancer have been significantly diminished or have disappeared entirely based on clinical diagnostics, although cancerous cells can still exist in the body. Thus, it is contemplated that clinical response encompasses partial and complete response. The presence of residual cancer cells can be enumerated by assays such as CTC (Circulating Tumor Cells) and can be predictive of recurrence.

"Relapse" or "recurrence" or "resurgence" are used interchangeably herein, and refer to the radiographic diagnosis of return, or signs and symptoms of return of cancer after a period of improvement or response.

As used herein, the term "antagonist" refers to a molecule which blocks (e.g., reduces or prevents) a biological activity. The term "inhibit" or "inhibition" means to reduce by a measurable amount.

As used herein, the term "ligand" refers to a molecule that forms a complex with a biomolecule (e.g., a receptor) to serve a biological purpose. In a narrower sense, is a signal triggering molecule, binding to a site on a target protein. The binding occurs by intermolecular forces, such as ionic bonds, hydrogen bonds and van der Waals forces. The docking (association) is usually reversible (dissociation). Actual irreversible covalent binding between a ligand and its target molecule is rare in biological systems. Ligand binding to a receptor (receptor protein) alters its chemical conformation (three dimensional shape). The conformational state of a receptor protein determines its functional state.

The "level" of a protein refers to the amount of protein in a sample as determined using any method known in the art for measuring protein levels, including electrophoresis, capillary electrophoresis, high performance liquid chromatography (HPLC), thin layer chromatography (TLC), hyperdiffusion chromatography, fluid or gel precipitation reactions, absorption spectroscopy, colorimetric assays, spectrophotmetric assays, flow cytometry, immmunodiffusion, solution phase assay, immunoelectrophoresis, Western blotting, radioimmunoassay (RIA), enzyme-linked immunosorbent assays (ELISAs), immunofluorescent assays and electrochemiluminescence immunoassays.

The term "sample" refers to a collection of fluids, cells or tissues isolated from a subject. Biological fluids are typically liquids at physiological temperatures and may include naturally occurring fluids present in, withdrawn from, expressed or otherwise extracted from a subject or biological source. Examples of biological fluids include blood, serum, serosal fluids, plasma, lymph, urine, cerebrospinal fluid, saliva, ocular fluids, cystic fluid, tear drops, feces, sputum, mucosal secretions, vaginal secretions, gynecological fluids, ascites fluids such as those associated with non-solid tumors, fluids of the pleural, pericardial, peritoneal, abdominal and other body cavities, fluids collected by bronchial lavage and the like.

The term "control sample", as used herein, refers to any clinically relevant control sample, including, for example, a sample from a healthy subject or a sample made at an earlier time point from the subject to be assessed. For example, the control sample can be a sample taken from the subject prior to onset of cancer, at an earlier stage of disease, or before the administration of treatment or of a portion of treatment.

As used herein, the term "antibody" includes whole antibodies and any antigen binding fragment (i.e., "antigen-binding fragments" (also known as "antigen-binding portions")). Whole antibodies are glycoproteins comprising at least two heavy (H) chains and two light (L) chains interconnected by disulfide bonds. Each heavy chain is comprised of a heavy chain variable region (abbreviated herein as VH) and a heavy chain constant region. The heavy chain constant region is comprised of three domains, $C_H1$, $C_H2$ and $C_H3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. The term "antibody" also encompasses chimeric antibodies, humanized antibodies, fully human antibodies, as well as multimeric forms of antibodies, such as minibodies, bis-scFv, diabodies, triabodies, tetrabodies and chemically conjugated Fab' multimers.

The term "antibody fragment" (also referred to as "antigen-binding fragment" or "antigen-binding portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, $C_L$ and $C_H1$ domains; (ii) a F(ab')2 fragment, a bivalent fragment is essentially a Fab with part of the hinge region (see, FUNDAMENTAL IMMUNOLOGY (Paul ed., 3.sup.rd ed. 1993); (iv) a Fd fragment consisting of the $V_H$ and $C_H1$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody (also known as a single-domain antibody (sdAb)), which is a heavy chain variable region containing a single variable domain and two constant domains. Single domain antibodies include $V_HH$ fragments (single-domain antibodies engineered from heavy-chain antibodies found in camelids, as well as VNAR fragments (single-domain antibodies obtained from heavy-chain antibodies (IgNAR, 'immunoglobulin new antigen receptor') of cartilaginous fishes).

"Antigen binding scaffolds" are proteins that bind specifically to a target (or antigen) or epitope, such as proteins comprising an Ig fold or an Ig-like fold. Antibodies or antigen binding fragments thereof are also antigen binding scaffolds. Antigen binding scaffolds can be monovalent, multivalent, e.g., bivalent, trivalent, tetravalent, or bind 5, 6 or more epitopes. Multivalent antigen binding scaffolds can be monospecific or multispecific, i.e., binding to multiple (at least 2, 3, 4 or 5) epitopes that are different from one another. For example, a multivalent monospecific antigen binding scaffold is a protein that binds to at least 2, 3, 4 or 5 identical epitopes, and may be a protein comprising at least 2, 3, 4 or 5 identical antigen binding portions. For example, TIM-4 binding scaffolds may comprise 2-10, e.g., 2-6, 2-5, 2-4 or 2-3 TIM-4 binding portions, which may be the same or different from one another.

A multivalent antibody includes antibodies comprising at least 2, 3, 4, 5, 6, 7, 8, 9, 10 or more antigen binding portions of antibodies, which antigen binding portions may comprise a portion of a heavy chain and a portion of a light chain. An antigen binding portion may be on a single polypeptide or comprise more than one polypeptide. For example, a multivalent antibody may comprise from 2-10 antigen binding portions, which may be the same or different from each other. A multivalent antibody may be monospecific or multispecific. A multispecific antibody may be bispecific, trispecific, tetraspecific or bind to 5 or more different epitopes.

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Nat. Acad. Sci. USA* 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies.

As used herein, an antigen binding scaffold that "specifically binds" to an antigen or epitope thereof is an antigen binding scaffold that binds to the antigen or epitope thereof with a $K_D$ of $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M or less. For example, an antigen binding scaffold that specifically binds to TIM-4 is an antigen binding scaffold that binds to TIM-4 with a $K_D$ of $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M or less. For example, an antibody that "specifically binds to human PD-1" or "specifically binds to human PD-L1" is intended to refer to an antibody that binds to human PD-1 or PD-L1, respectively, with a $K_D$ of $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M or less. An antigen binding scaffold that comprises 2 or more regions binding to an antigen or epitope may bind specifically to the antigen or epitope even it has a lower affinity of binding to the antigen or epitope than the ranges provided above, as it will bind to the antigen or epitope with increased avidity.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "monoclonal antibody" as used herein, refers to refers to an antibody from a population of substantially homogeneous antibodies that display a single binding specificity and affinity for a particular epitope, except for possible variants that may arise during production of the monoclonal antibody, such variants generally being present in minor amounts. Accordingly, the term "human monoclonal antibody" or "monoclonal antibody composition" refers to an antibody which has variable and optional constant regions derived from human germline immunoglobulin sequences. The modifier "monoclonal" indicates the character of the antibody as being obtained from a substantially homogeneous population of antibodies, and is not to be construed as requiring production of the antibody by any particular method. For example, the monoclonal antibodies described herein may be made by a variety of techniques. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art and those described herein, for example, x-ray crystallography, HDX-MS and 2-dimensional nuclear magnetic resonance (see, e.g., *Epitope Mapping Protocols in Methods in Molecular Biology*, Vol. 66, G. E. Morris, Ed. (1996)).

The term "epitope mapping" refers to the process of identification of the molecular determinants for antibody-antigen recognition.

The term "binds to the same epitope," with reference to two or more antibodies, means that the antibodies compete for binding to an antigen and bind to the same, overlapping, or encompassing continuous or discontinuous segments of amino acids. Those of skill in the art understand that the phrase "binds to the same epitope" does not necessarily mean that the antibodies bind to exactly the same amino acids. The precise amino acids to which the antibodies bind can differ. For example, a first antibody can bind to a segment of amino acids that is completely encompassed by the segment of amino acids bound by a second antibody. In another example, a first antibody binds one or more segments of amino acids that significantly overlap the one or more segments bound by the second antibody. For the purposes herein, such antibodies are considered to "bind to the same epitope." Two antibodies "bind to the same epitope" as determined by a given method, e.g., HDX-MS, crystallography or target mutational analysis, requires that the same amino acids are identified for both antibodies by one or more given methods.

Accordingly, also, encompassed by the present invention are antibodies that bind to an epitope which comprises all or a portion of an epitope recognized by the particular antibodies described herein (e.g., the same or an overlapping region or a region between or spanning the region) or that bind to the same epitope as determined by a given method, e.g., HDX-MS, crystallography or target mutational analysis.

Also encompassed by the present invention are antibodies that compete for binding with the antibodies described herein, and optionally bind the same epitope. Antibodies that compete for binding can be identified using routine techniques. Such techniques include, for example, an immunoassay, which shows the ability of one antibody to block the binding of another antibody to a target antigen, i.e., a competitive binding assay. Competitive binding is determined in an assay in which the immunoglobulin under test inhibits specific binding of a reference antibody to a common antigen. Numerous types of competitive binding assays are known, for example: Biacore, flow cytometry, solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

Epitope mapping methods also include x-ray analyses of crystals of antigen:antibody complexes which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display or yeast display peptide libraries. The peptides are then regarded as leads for the definition of the epitope corresponding to the antibody used to screen the peptide library. For epitope mapping, computational algorithms have also been developed which have been shown to map conformational discontinuous epitopes.

Chimeric molecules (or fusion molecules) comprising an antigen binding domain, or equivalent, fused to another polypeptide or molecule are also encompassed by the present invention. For example, the polypeptides may be fused or conjugated to an antibody Fc region, or portion thereof (e.g., an Fc fusion protein). The antibody portion fused to a polypeptide may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603, 5,622,929, 5,359,046, 5,349,053, 5,447,851, and 5,112,946; EP 307,434; EP 367,166; PCT Publication Nos. WO 96/04388 and WO 91/06570; Ashkenazi et al., Proc. Natl. Acad. Sci. USA, 88:10535-10539 (1991); Zheng et al., J. Immunol., 154:5590-5600 (1995); and Vil et al., Proc. Natl. Acad. Sci. USA, 89:11337-11341 (1992).

As used herein, the term "immunoconjugate" refers to an antibody linked to a therapeutic moiety, such as a cytotoxin, a drug or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Antibodies use in the present invention can be conjugated to a radioisotope, e.g., radioactive iodine, to generate cytotoxic radiopharmaceuticals for treating cancer.

Immunoconjugates can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *Pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

As used herein, the term "multivalent" refers to a recombinant molecule that incorporates more than two biologically active segments. The protein fragments forming the multivalent molecule optionally may be linked through a polypeptide linker which attaches the constituent parts and permits each to function independently.

As used herein, "functional equivalents" refer to peptides or polypeptides (e.g., antibodies or antigen binding portion thereof) which maintain a substantial amount of their original immunological activity. For example, certain amino acids may be substituted for other amino acids in a protein structure without appreciable loss of interactive binding capacity with structures such as, for example, antigenbinding regions of antibodies or binding sites on substrate molecules. It is thus contemplated that various changes may be made in the amino acid sequences of the disclosed compositions without appreciable loss of their biological utility or activity. Amino acid substitutions may be based on the relative similarity of the amino acid side-chain substituents, for example, their hydrophobicity, hydrophilicity, charge, size, and the like. Exemplary substitutions which take various of the foregoing characteristics into consideration are well known to those of skill in the art, and such immunologically functional equivalents are also encompassed within the present invention.

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by a sequence alignment program, such as BLAST, BLAST-2, ALIGN, ALIGN-2 or Megalign (DNASTAR), in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

II. PD-1 Antagonists

As used herein, the terms "Protein PD-1," "PD-1," "PD1," "PDCD1" are used interchangeably with "Programmed Death 1," "Programmed Cell Death 1." The complete human PD-1 sequence can be found under GenBank Accession No. U64863 (SEQ ID NO:23).

As used herein, the terms "PD-L1", "PDL1", "PDCD1L1", "PDCD1LG1", "CD274", "B7 homolog 1", "B7-H1", "B7-H", and "B7H1" are used interchangeably with "Programmed Cell Death 1 Ligand 1." The complete human PD-L1 amino acid sequence—isoform a precursor—can be found under GenBank Accession No. NP_054862.1 (SEQ ID NO:24). The complete human PD-L1 amino acid sequence—isoform b precursor—can be found under GenBank Accession No. NP_001254635.1 (SEQ ID NO:25).

The protein Programmed Death 1 (PD-1) is an inhibitory member of the CD28 family of receptors, that also includes CD28, CTLA-4, ICOS and BTLA. PD-1 is expressed on activated B cells, T cells, and myeloid cells (Agata et al., supra; Okazaki et al. (2002) *Curr. Opin. Immunol.* 14: 391779-82; Bennett et al. (2003) *J Immunol* 170:711-8). The initial members of the family, CD28 and ICOS, were discovered by functional effects on augmenting T cell proliferation following the addition of monoclonal antibodies (Hutloff et al. (1999) *Nature* 397:263-266; Hansen et al. (1980) *Immunogenics* 1:247-260). PD-1 was discovered through screening for differential expression in apoptotic cells (Ishida et al. (1992) *EMBO J* 11:3887-95). The other members of the family, CTLA-4 and BTLA, were discovered through screening for differential expression in cytotoxic T lymphocytes and TH1 cells, respectively. CD28, ICOS and CTLA-4 all have an unpaired cysteine residue allowing for homodimerization. In contrast, PD-1 is suggested to exist as a monomer, lacking the unpaired cysteine residue characteristic in other CD28 family members.

The PD-1 protein is a 55 kDa type I transmembrane protein that is part of the Ig gene superfamily (Agata et al. (1996) *Int Immunol* 8:765-72). PD-1 contains a membrane proximal immunoreceptor tyrosine inhibitory motif (ITIM) and a membrane distal tyrosine-based switch motif (ITSM) (Thomas, M. L. (1995) *J Exp Med* 181:1953-6; Vivier, E and Daeron, M (1997) *Immunol Today* 18:286-91). Although structurally similar to CTLA-4, PD-1 lacks the MYPPPY motif (SEQ ID NO: 27) that is critical for B7-1 and B7-2 binding.

Consistent with PD-1 being an inhibitory member of the CD28 family, PD-1 deficient animals develop various autoimmune phenotypes, including autoimmune cardiomyopathy and a lupus-like syndrome with arthritis and nephritis (Nishimura et al. (1999) *Immunity* 11:141-51; Nishimura et al. (2001) *Science* 291:319-22). Additionally, PD-1 has been found to play a role in autoimmune encephalomyelitis, systemic lupus erythematosus, graft-versus-host disease (GVHD), type I diabetes, and rheumatoid arthritis (Salama et al. (2003) *J Exp Med* 198:71-78; Prokunina and Alarcon-Riquelme (2004) *Hum Mol Genet* 13:R143; Nielsen et al. (2004) *Lupus* 13:510). In a murine B cell tumor line, the ITSM of PD-1 was shown to be essential to block BCR-mediated $Ca^{2+}$-flux and tyrosine phosphorylation of downstream effector molecules (Okazaki et al. (2001) *PNAS* 98:13866-71).

Two ligands for PD-1 have been identified, PD-L1 and PD-L2, that have been shown to downregulate T cell activation upon binding to PD-1 (Freeman et al. (2000) *J Exp Med* 192:1027-34; Latchman et al. (2001) *Nat Immunol* 2:261-8; Carter et al. (2002) *Eur J Immunol* 32:634-43). Both PD-L1 and PD-L2 are B7 homologs that bind to PD-1, but do not bind to other CD28 family members. PD-L1 is abundant in a variety of human cancers (Dong et al. (2002) *Nat. Med.* 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) *J. Mol. Med.* 81:281-7; Blank et al. (2005) *Cancer Immunol. Immunother.* 54:307-314; Konishi et al. (2004) *Clin. Cancer Res.* 10:5094-100). Immune suppression can be reversed by inhibiting the local interaction of PD-1 with PD-L1, and the effect is additive when the interaction of PD-1 with PD-L2 is blocked as well (Iwai et al. (2002) *Proc. Nat'l. Acad. Sci. USA* 99:12293-7; Brown et al. (2003) *J. Immunol.* 170:1257-66).

The methods of the present invention involve the use of a PD-1 antagonist (e.g., an antibody) in combination with a TIM-4 antagonist (e.g., an antibody), for treating cancer. Accordingly, PD-1 antagonists of the invention bind to ligands of PD-1 and interfere with, reduce, or inhibit the binding of one or more ligands to the PD-1 receptor, or bind directly to the PD-1 receptor, without engaging in signal transduction through the PD-1 receptor. In one embodiment, the PD-1 antagonist binds directly to PD-1 and blocks PD-1 inhibitory signal transduction. In another embodiment the PD-1 antagonist binds to one or more ligands of PD-1 (e.g., PD-L1 and PD-L2) and reduces or inhibits the ligand(s) from triggering inhibitory signal transduction through the PD-1. In one embodiment, the PD-1 antagonist binds directly to PD-L1, inhibiting or preventing PD-L1 from binding to PD-1, thereby blocking PD-1 inhibitory signal transduction.

PD-1 antagonists used in the methods and compositions of the present invention include PD-1 binding scaffold proteins and include, but are not limited to, PD-1 ligands, antibodies and multivalent agents. In a particular embodiment, the antagonist is a fusion protein, such as AMP-224. In another embodiment, the antagonist is an anti-PD-1 antibody ("PD-1 antibody"). Anti-human-PD-1 antibodies (or VH and/or VL domains derived therefrom) suitable for use in the invention can be generated using methods well known in the art. Alternatively, art recognized anti-PD-1 antibodies can be used. For example, antibodies nivolumab (OPDIVO™), MK-3475 (pembrolizumab (KEYTRUDA™), PDR001 or CT-011 can be used. Additionally, monoclonal antibodies 5C4, 17D8, 2D3, 4H1, 4A11, 7D3, and 5F4, described in WO 2006/121168, the teachings of which are hereby incorporated by reference, can be used. Antibodies that compete with any of these art-recognized antibodies for binding to PD-1 also can be used.

An exemplary anti-PD-1 antibody is 5C4 comprising heavy and light chains having the sequences shown in SEQ ID NOs: 11 and 12, respectively, or antigen binding fragments and variants thereof. In other embodiments, the antibody comprises the heavy and light chain CDRs or variable regions of 5C4. Accordingly, in one embodiment, the antibody comprises the CDR1, CDR2, and CDR3 domains of the VH of 5C4 having the sequence set forth in SEQ ID NO: 13, and the CDR1, CDR2 and CDR3 domains of the VL of 5C4 having the sequences set forth in SEQ ID NO: 15. In another embodiment, the antibody comprises CDR1, CDR2 and CDR3 domains having the sequences set forth in SEQ ID NOs: 17, 18, and 19, respectively, and CDR1, CDR2 and CDR3 domains having the sequences set forth in SEQ ID NOs: 20, 21, and 22, respectively. In another embodiment, the antibody comprises VH and/or VL regions having the amino acid sequences set forth in SEQ ID NO: 13 and/or SEQ ID NO: 15, respectively. In another embodiment, the antibody comprises the heavy chain variable (VH) and/or light chain variable (VL) regions encoded by the nucleic acid sequences set forth in SEQ ID NO: 14 and/or SEQ ID NO: 16, respectively. In another embodiment, the antibody competes for binding with and/or binds to the same epitope on PD-1 as the above-mentioned antibodies. In another embodiment, the antibody has at least about 90% variable region amino acid sequence identity with the above-mentioned antibodies (e.g., at least about 90%, 95% or 99% variable region identity with SEQ ID NO: 13 or SEQ ID NO: 15).

In certain embodiments, the PD1 antibodies exhibit one or more desirable functional properties, such as high affinity binding to PD-1, e.g., binding to human PD-1 with a $K_D$ of $10^{-7}$ M or less; lack of significant cross-reactivity to other CD28 family members, e.g., CD28, CTLA-4 and ICOS; the ability to stimulate T cell proliferation in a mixed lymphocyte reaction (MLR) assay; the ability to increase IFN-7 and/or IL-2 secretion in an MLR; the ability to inhibit binding of one or more PD-1 ligands (e.g., PD-L1 and/or PD-L2) to PD-1; the ability to stimulate antigen-specific memory responses; the ability to stimulate antibody responses and/or the ability to inhibit growth of tumor cells in vivo.

In another embodiment, the PD-1 antagonist is an anti-PD-L1 antibody. Anti-human-PD-L1 antibodies (or VH and/or VL domains derived therefrom) suitable for use in the invention can be generated using methods well known in the art. Alternatively, art recognized anti-PD-L1 antibodies can be used. For example, MEDI4736 (also known as Anti-B7-H1; durvalumab (IMFINZI™)), MPDL3280A (atezolizumab (TECENTRIQ™) also known as RG7446), and avelumab (BAVENCIO™) and can be used. Additionally, monoclonal antibodies 12A4, 3G10, 10A5, 5F8, 10H10, 1B12, 7H1, 11E6, 12B7, and 13G4 described in WO 2007/005874 and U.S. Pat. No. 7,943,743, the teachings of which are hereby incorporated by reference, can be used. Antibodies that compete with any of these art-recognized antibodies for binding to PD-L1 also can be used.

An exemplary anti-PD-L1 antibody is 12A4 (WO 2007/005874 and U.S. Pat. No. 7,943,743). In one embodiment, the antibody comprises the heavy and light chain CDRs or VRs of 12A4. Accordingly, in one embodiment, the antibody comprises the CDR1, CDR2, and CDR3 domains of the VH region of 12A4 having the sequence shown in SEQ ID NO: 1 and the CDR1, CDR2 and CDR3 domains of the VL region of 12A4 having the sequence shown in SEQ ID NO: 3. In another embodiment, the antibody comprises the heavy chain CDR1, CDR2 and CDR3 domains having the sequences set forth in SEQ ID NOs: 5, 6, and 7, respectively, and the light chain CDR1, CDR2 and CDR3 domains having the sequences set forth in SEQ ID NOs: 8, 9, and 10, respectively. In another embodiment, the antibody comprises VH and/or VL regions having the amino acid sequences set forth in SEQ ID NO: 1 and/or SEQ ID NO: 3, respectively. In another embodiment, the antibody comprises the heavy chain variable (VH) and/or light chain variable (VL) regions encoded by the nucleic acid sequences set forth in SEQ ID NO: 2 and/or SEQ ID NO: 4, respectively. In another embodiment, the antibody competes for binding with, and/or binds to the same epitope on PD-L1 as, the above-mentioned antibodies. In another embodiment, the antibody has at least about 90% variable region amino acid sequence identity with the above-mentioned antibodies (e.g., at least about 90%, 95% or 99% variable region identity with SEQ ID NO: 1 or SEQ ID NO: 3).

Anti-PD-1 or anti-PD-L1 antibodies may bind to PD-1 or PD-L1, respectively, with a $K_D$ of $10^{-7}$ M, $5\times10^{-8}$ M, $10^{-8}$ M, $5\times10^{-9}$ M, $10^{-9}$ M, $5\times10^{-10}$ M, $10^{-10}$ M or less.

In certain embodiments, an anti-PD-1 or anti-PD-L1 antibody is an IgG antibody, such as an IgG1, IgG2 or IgG4 antibody. In specific embodiments, an anti-PD-1 or PD-li antibody has an effectorless constant region. Anti-PD-1 or PD-L1 antibodies may be IgG4 antibodies, e.g., IgG4 antibodies having an S228P mutation.

III. TIM-4 Antagonists

As used herein, the terms "TIM-4" and "TIMD-4", also known as "T-cell immunoglobulin and mucin domain-containing protein 4", "T-cell immunoglobulin mucin receptor 4," "T-cell membrane protein 4" and "SMUCKLER" are used interchangeably. The complete amino acid and nucleotide sequences of isoform-1 of human TIM-4 can be found under GenBank Accession Nos. NP_612388.2 and NM_138379.2, respectively (SEQ ID NOs: 26-27). The complete amino acid and nucleotide sequences of isoform-2 of human TIM-4 can be found under GenBank Accession Nos. NP_001140198.1 and NM_001146726.1, respectively (SEQ ID NOs: 28-29) (Jones et al., *Int Arch Allergy Immunol.* 2006; 141(4):331-6). An alignment of the two human isoforms is depicted in FIG. 1.

The amino acid sequences of TIM-4 isoforms from cynomologus monkey can be found under GenBank Accession Nos. XP_005558436 and EHH54702, and the amino acid sequences for murine TIM-4 isoforms can be found under GenBank Accession Nos. NP_848874 and NP_599009. An alignment of the amino acid sequences of mouse, cynomolgus monkey and human TIM-4 polypeptides is provided in FIG. 2, and the percent identity of the full-length and IgV regions of human, cynomolgus and murine orthologs are set forth in Table 1.

TABLE 1

TIM-4 Orthologs

| | hTIM4-FL | hTIM4_IgV |
|---|---|---|
| Cyno | 87% | 93% |
| Mouse | 49% | 64% |

The protein "TIM-4" is type I membrane protein that is a member of T-cell immunoglobulin and mucin domain-containing (TIM) family. The human TIM family contains three members (TIM-1, TIM-3 and TIM-4) on human chromosome 5q33.2, located in a chromosomal region that has been linked with asthma, allergy and autoimmunity. TIM proteins are type I cell-surface glycoproteins with common structural features including an N-terminal immunoglobulin (IgV)-like domain with highly conserved cysteine residues, a threonine-rich mucin domain with O-linked and N-linked glycosylations, a single transmembrane domain, and a cytoplasmic region. While the cytoplasmic domain of human TIM-1 and TIM-3 contain tyrosine phosphorylation motif(s), TIM-4 lacks a phosphotyrosine motif.

TIM-4 is expressed on myeloid cells, including dendritic cells (DCs) and macrophages from spleen, lymph nodes, or peritoneal cavity. TIM-4 has been demonstrated to bind to TIM-1, MerTK, Integrin αvβ3 and phosphatidyl serine via the IgV domain. MerTK and Integrin αvβ3 may play a role in certain TIM4 mediated biological activities (Nishi et al. (2014) Mol Cell Biol. 34(8):1512-20 and Toda et al. (2012) *Mol Cell Biol.* 32(1):118-25). TIM-4 differentially regulates T cell homeostasis by inhibiting naïve T cells during the induction phase of an immune response and enhancing T cell responses at the effector phase (Rodriguez-Manzanet et al., supra). For example, TIM-4 binds to TIM-1, which is present on activated T cells, and co-stimulates T cell proliferation.

TIM-4 binds to the phosphatidylserine (PS) through the FG-CC' binding cleft in the N-terminal immunoglobulin variable (IgV) domain. TIM-4 is upregulated following the release of DAMPs, and enhances efferocytosis of apoptotic cells by macrophages (Kobayashi, 2007; Albacker, et al., J. Immunol. 2010; 185:6839-6849; Mizui et al. Int. Immunol. 2008; 20:695-708). In contrast, TIM-4 knockout mice have defects in lysosomal degradation, antigen presentation and cross-priming (Miyanishi 2012, Rodrigues-Manzaneta, 2010).

TIM-4 has been demonstrated to be expressed on macrophages and DCs in the tumor microenvironment (TME), and may modulate the interaction between myeloid cells and antigen-specific cytotoxic T cells within tumors. Bahgdadi et al. (supra) reported that apoptotic tumor cells were ingested by TIM-4+ bone-marrow derived macrophages (BMDMs), suggesting that TIM-4 contributes to immune tolerance by promoting excessive lysosomal degradation of ingested tumor cells, leading to impaired tumor antigen presentation by TIM-4+ tumor-associated macrophages (TAMs). Inhibition of this function appears to promote antitumor activity following monotherapy with an anti-TIM-4 blocking antibody and demonstrates synergistic antitumor activity when combined with an anti-TIM-3 blocking antibody in the context of the vaccine therapy model (Baghadadi 2013).

The term "antagonist" as used with reference to TIM-4 refers to any molecule that partially or fully inhibits one or more biological activities of TIM-4, in vitro, in situ, or in vivo. Examples of such biological activities include binding of TIM-4 to PS, efferocytosis of tumor cells, and suppression of tumor antigen presentation, as well as those further reported in the literature. TIM-4 antagonists may function in a direct or indirect manner. For example, the TIM-4 antagonist may function to partially or fully inhibit one or more biological activities of TIM-4, in vitro, in situ, or in vivo as a result of blocking direct binding to TIM-4 to PS and/or blocking the interaction of TIM-4 to other PS receptors and reducing cellular ability to engage in efferocytosis of tumor cells. The antagonist may also function by interfering with TIM-4 interaction with TIM-1 thereby preventing direct T cell regulatory activity. The TIM-4 antagonist may also function indirectly to partially or fully inhibit one or more biological activities of TIM-4, in vitro, in situ, or in vivo as a result of, e.g., inhibiting another molecule which then blocks TIM-4 activation or expression. It is contemplated that an antagonist may act as a molecule which functions indirectly to block, inhibit or decrease TIM-4 expression or activity.

A TIM-4 antagonist may be any molecule that directly or indirectly inhibits or decreases the activity of TIM-4 and reduces tumor growth, whether on its own or in combination with another treatment, such as a PD-1 antagonist. Exemplary TIM-4 antagonists include TIM-4 binding scaffolds, such as anti-TIM-4 antibodies ("TIM-4 antibodies"), e.g., chimeric, humanized or fully human antibodies, an antigen binding portion thereof, or molecules that are based on or derived from any of these. TIM-4 antagonists may also be non-antibody proteins. For example, TIM-4 antagonist also include modified TIM-4 ligands or binding proteins, e.g., TIM-1 and molecules that are derived from or based on PS. In addition, TIM-4-regulated biology may be interfered with by fusion proteins such as TIM-4: Ig.

A TIM-4 antagonist may be monovalent or multivalent. In certain embodiments, a TIM-4 antagonist is bivalent, trivalent, tetravalent, or binds to 5, 6, 7, 8, 9, 10 or more TIM-4 epitopes, which may be the same or different TIM-4 epitopes. In certain embodiments, a TIM-4 antagonist is a multivalent monospecific TIM-4 binding scaffold, e.g., a protein comprising a TIM-4 binding scaffold that comprises at least 2, 3, 4, 5, 6, 7, 8, 9, 10 or more regions that specifically bind to the same TIM-4 epitope, which binding regions may be composed of the same or a different amino acid sequence. For example, a TIM-4 antagonist may be a TIM-4 binding scaffold comprising 2, 3, 4, 5, 6, 7, 8, 9, 10 or more repeats of the same TIM-4 binding region, e.g., the N-terminal IgV region or portion thereof containing the FG-CC' binding cleft of the IgV region.

In certain embodiments, a TIM-4 antagonist binds specifically to TIM-4, but does not bind significantly or specifically to other members of the TIM family, such as TIM-1 or TIM-3. In other embodiments, a TIM-4 antagonist binds specifically to TIM-4 and TIM-1.

In another embodiment, the TIM-4 antagonist is an antibody, e.g., an antibody that binds to human TIM-4 with a $K_D$ of $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M or less, wherein the antibody inhibits tumor growth, and/or increases tumor antigen specific CTLs. Antibodies binding to human TIM-4 are known in the art. Any of these antibodies may be used in combination with a PD-1 antagonist, provided that their combination results in inhibition of tumor growth or reduction in tumor size, e.g., in a subject having cancer. Exemplary antibodies include those which bind specifically to the N-terminal IgV domain of TIM-4 (e.g., the FG-CC" binding cleft). Anti-TIM-4 antibodies include those which bind human TIM-4, e.g., 9F4 (BioLegend). Anti-mouse anti-TIM4 antibodies include RMT4-53 (BioXCell, GeneTex), RMT4-54 (BioLegend) F31-5G3 and 21H12 (BioLegend, BD Biosciences, respectively). Variants of these antibodies, such as antibodies comprising the CDRs of these antibodies, or antibodies that compete for binding to human or murine TIM-4 with one of these antibodies or antibodies that bind to the same or similar epitope on TIM-4 as one of these antibodies may be used in combinations with a PD-1 antagonist.

In certain embodiments, an anti-TIM4 antibody for use in the methods described herein binds to a region on human TIM-4 that is not the IgV domain, and can be, e.g., the stem domain or any other region in the extracellular domain of TIM-4, provided that the antibody antagonizes the biological activity of TIM-4, and has at least an additive effect with a PD-1 antagonist when used for treating cancer (relative to either agent alone).

In another embodiment, the TIM-4 antagonist is a multivalent agent, such as a multimer (e.g., a polypeptide construct with trimerizing domain and a polypeptide that binds TIM-4).

Agents, which compete for binding to TIM-4 with any of the exemplary agents listed herein, and which inhibit tumor growth or reduces tumor size may also be used. Antibodies having VH and VL chains comprising an amino acid sequence that is at least 90%, 95%, 98% or 99% identical to those of any of the anti-TIM-4 antibodies listed herein may be used.

Administration of a TIM-4 antagonist may be monitored by imaging with a phosphatidylserine (PS)-binding agent (e.g. annexin V peptides, TIM-4 binding fragments), where the PS binding agent may be labeled for imaging, e.g. PET, SPECT, fluorescence, etc. The binding agent is brought into contact with the target tumor cells, and the presence of bound agent is indicative of PS being present and able to interact with TIM-4.

For example, Annexin V is a ubiquitous intracellular protein in humans that has a nanomolar affinity for the membrane-bound constitutive anionic phospholipid phosphatidylserine (PS), which is selectively expressed on the surface of apoptotic or physiologically stressed cells. As such, radiolabeled forms of annexin V have been used in both animal models and human Phase I and Phase II trials for utilizing the tracer as an early surrogate marker of therapeutic efficacy (e.g., Blankenberg et al. Proc. Am. J. Thoracic. Soc. 2009; 6:469-476). For example, the in vivo monitoring of PS within the tumor microenvironment may be performed with anti-annexin V linked to a label radiotracer (for PET or SPECT), or with a TIM-4 fusion protein linked to a label or radiotracer. Labels could include q-dots for near IR imaging, or other more conventional labels. pK/Kd studies may be performed with radiolabeled antibodies.

IV. Compositions

In one aspect, the present invention provides composition comprising a PD-1 antagonist and a TIM-4 antagonist (e.g., formulated together in a single composition or separately formulated). In one embodiment, the PD-1 antagonist is nivolumab, pembrolizumab, durvalumab, atezolizumab, avelumab or PDR001. In one embodiment, the composition comprises a PD-1 antagonist and a TIM-4 antagonist, wherein (a) the PD-1 antagonist is an anti-PD-1 antibody comprising the CDR1, CDR2 and CDR3 domains in a heavy chain variable region having the sequence set forth in SEQ ID NO: 13, and the CDR1, CDR2 and CDR3 domains in a light chain variable region having the sequence set forth in SEQ ID NO: 15; and (b) the TIM-4 antagonist is an antibody. In another embodiment, the composition comprises a PD-1 antagonist and a TIM-4 antagonist, wherein (a) the PD-1 antagonist is an anti-PD-L1 antibody comprising the CDR1, CDR2 and CDR3 domains in a heavy chain variable region having the sequence set forth in SEQ ID NO: 1, and the CDR1, CDR2 and CDR3 domains in a light chain variable region having the sequence set forth in SEQ ID NO: 3 and (b) the TIM-4 antagonist is an antibody.

Pharmaceutical compositions suitable for administration to human patients are typically formulated for parenteral administration, e.g., in a liquid carrier, or suitable for reconstitution into liquid solution or suspension for intravenous administration.

In general, such compositions typically comprise a pharmaceutically acceptable carrier. As used herein, the term "pharmaceutically acceptable" means approved by a government regulatory agency or listed in the U.S. Pharmacopeia or another generally recognized pharmacopeia for use in animals, particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil, glycerol polyethylene glycol ricinoleate, and the like. Water or aqueous solution saline and aqueous dextrose and glycerol solutions may be employed as carriers, particularly for injectable solutions. Liquid compositions for parenteral administration can be formulated for administration by injection or continuous infusion. Routes of administration by injection or infusion include intravenous, intraperitoneal, intramuscular, intrathecal and subcutaneous.

For oral use, the pharmaceutical compositions of the present invention, may be administered, for example, in the form of tablets or capsules, powders, dispersible granules, or cachets, or as aqueous solutions or suspensions. In the case of tablets for oral use, carriers which are commonly used include lactose, corn starch, magnesium carbonate, talc, and sugar, and lubricating agents such as magnesium stearate are commonly added. For oral administration in capsule form, useful carriers include lactose, corn starch, magnesium carbonate, talc, and sugar. When aqueous suspensions are used for oral administration, emulsifying and/or suspending agents are commonly added.

In addition, sweetening and/or flavoring agents may be added to the oral compositions. For intramuscular, intraperitoneal, subcutaneous and intravenous use, sterile solutions of the active ingredient(s) are usually employed, and the pH of the solutions should be suitably adjusted and buffered. For intravenous use, the total concentration of the solute(s) should be controlled in order to render the preparation isotonic.

For preparing suppositories according to the invention, a low melting wax such as a mixture of fatty acid glycerides or cocoa butter is first melted, and the active ingredient is dispersed homogeneously in the wax, for example by stirring. The molten homogeneous mixture is then poured into conveniently sized molds and allowed to cool and thereby solidify.

Liquid preparations include solutions, suspensions and emulsions. Such preparations are exemplified by water or water/propylene glycol solutions for parenteral injection. Liquid preparations may also include solutions for intranasal administration.

Aerosol preparations suitable for inhalation may include solutions and solids in powder form, which may be in combination with a pharmaceutically acceptable carrier, such as an inert compressed gas.

Also included are solid preparations which are intended for conversion, shortly before use, to liquid preparations for either oral or parenteral administration. Such liquid forms include solutions, suspensions and emulsions.

V. Patient Populations

Provided herein are effective methods for treating cancer in a patient, e.g., using a combination of a TIM-4 antagonist and PD-1 antagonist. In one embodiment, the patient suffers from a cancer selected from the group consisting of carcinoma, sarcoma, blastoma, leukemia and lymphoma. In another embodiment, the patient suffers from a cancer selected from the group consisting of non-small cell lung cancer, small cell lung cancer, gastrointestinal cancer, colorectal cancer, stomach cancer, colon carcinoma and glioblastoma. In another embodiment, the patient suffers from a cancer selected from the group consisting of chronic myeloid leukemia, acute lymphoblastic leukemia, Philadelphia chromosome positive acute lymphoblastic leukemia (Ph+ALL), squamous cell carcinoma, small-cell lung cancer, non-small cell lung cancer, glioma, gastrointestinal cancer, renal cancer, ovarian cancer, liver cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, acute myelogenous leukemia (AML), and chronic lymphocytic leukemia (CML).

VI. Additional Agents/Therapies

The combinations of the present invention (e.g., PD-1 antagonist in combination with TIM-4 antagonist) may also be used in conjunction with other well known therapies that are selected for their particular usefulness against the cancer that is being treated. Combinations of the instant invention may alternatively be used sequentially with known pharmaceutically acceptable agent(s) when inappropriate.

For example, the PD-1 antagonists and TIM-4 antagonist described herein can further be used in combination (e.g., simultaneously or separately) with an additional treatment, such as irradiation, chemotherapy (e.g., using camptothecin (CPT-11), 5-fluorouracil (5-FU), cisplatin, doxorubicin, irinotecan, paclitaxel, gemcitabine, cisplatin, paclitaxel, doxorubicin, 5-fu, or camptothecin+apo2l/TRAIL (a 6× combo)), one or more proteasome inhibitors (e.g., bortezomib or MG132), one or more Bcl-2 inhibitors (e.g., BH3I-2' (bcl-xl inhibitor), AT-101 (R-(−)-gossypol derivative), ABT-263 (small molecule), GX-15-070 (obatoclax), or MCL-1 (myeloid leukemia cell differentiation protein-1) antagonists), iAP (inhibitor of apoptosis protein) antagonists (e.g., smac7, smac4, small molecule smac mimetic, synthetic smac peptides (see Fulda et al., *Nat Med* 2002; 8:808-15), ISIS23722 (LY2181308), or AEG-35156 (GEM-640)), HDAC (histone deacetylase) inhibitors, anti-CD20 antibodies (e.g., rituximab), angiogenesis inhibitors (e.g., bevacizumab), antiangiogenic agents targeting VEGF and VEGFR, synthetic triterpenoids (see Hyer et al., *Cancer Research* 2005; 65:4799-808), c-FLIP (cellular FLICE-inhibitory protein) modulators (e.g., natural and synthetic ligands of PPARγ (peroxisome proliferator-activated receptor γ), 5809354 or 5569100), kinase inhibitors (e.g., Sorafenib), and/or genotoxic drugs.

The PD-1 antagonists and TIM-4 antagonists described herein can further be used in combination with one or more anti-proliferative cytotoxic agents. Classes of compounds that may be used as anti-proliferative cytotoxic agents include, but are not limited to, the following:

Alkylating agents (including, without limitation, nitrogen mustards, ethylenimine derivatives, alkyl sulfonates, nitrosoureas and triazenes): Uracil mustard, Chlormethine, Cyclophosphamide (CYTOXAN™) fosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Suitable anti-proliferative agents for use in the methods of the invention, include, without limitation, taxanes, paclitaxel (paclitaxel is commercially available as TAXOL®), docetaxel, discodermolide (DDM), dictyostatin (DCT), Peloruside A, epothilones, epothilone A, epothilone B, epothilone C, epothilone D, epothilone E, epothilone F, furanoepothilone D, desoxyepothilone B1, [17]-dehydrodesoxyepothilone B, [18]dehydrodesoxyepothilones B, C12,13-cyclopropyl-epothilone A, C6-C8 bridged epothilone A, trans-9,10-dehydroepothilone D, cis-9,10-dehydroepothilone D, 16-desmethylepothilone B, epothilone B10, discodermolide, patupilone (EPO-906), KOS-862, KOS-1584, ZK-EPO, ABJ-789, XAA296A (Discodermolide), TZT-1027 (soblidotin), ILX-651 (tasidotin hydrochloride), Halichondrin B, Eribulin mesylate (E-7389), Hemiasterlin (HTI-286), E-7974, Cyrptophycins, LY-355703, Maytansinoid immunoconjugates (DM-1), MKC-1, ABT-751, T1-38067, T-900607, SB-715992 (ispinesib), SB-743921, MK-0731, STA-5312, eleutherobin, 17beta-acetoxy-2-ethoxy-6-oxo-B-homo-estra-1,3,5(10)-trien-3-ol, cyclostreptin, isolaulimalide, laulimalide, 4-epi-7-dehydroxy-14,16-didemethyl-(+)-discodermolides, and cryptothilone 1, in addition to other microtubuline stabilizing agents known in the art.

In cases where it is desirable to render aberrantly proliferative cells quiescent in conjunction with or prior to treatment with the chemotherapeutic methods of the invention, hormones and steroids (including synthetic analogs), such as 17a-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, ZOLADEX™, can also be administered to the patient. When employing the methods or compositions of the present invention, other agents used in the modulation of tumor growth or metastasis in a clinical setting, such as antimimetics, can also be administered as desired.

Methods for the safe and effective administration of chemotherapeutic agents are known to those skilled in the art. In addition, their administration is described in the standard literature. For example, the administration of many of the chemotherapeutic agents is described in the Physicians' Desk Reference (PDR), e.g., 1996 edition (Medical Economics Company, Montvale, N.J. 07645-1742, USA); the disclosure of which is incorporated herein by reference thereto.

A PD-1 antagonist and a TIM4 antagonist may also be combined with one or more immunotherapy agent that stimulates the immune system, e.g., an agent that binds to human CTLA-4, LAG-3, GITR, OX40, IDO, CSF-1R etc.

The chemotherapeutic agent(s) and/or radiation therapy can be administered according to therapeutic protocols well known in the art. It will be apparent to those skilled in the art that the administration of the chemotherapeutic agent(s) and/or radiation therapy can be varied depending on the disease being treated and the known effects of the chemotherapeutic agent(s) and/or radiation therapy on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

VII. Treatment Protocols

Suitable treatment protocols for treating cancer in a patient include, for example, administering to the patient an effective amount of a PD-1 antagonist (e.g., antibody) and a TIM-4 antagonist (e.g., antibody).

As used herein, adjunctive or combined administration (co-administration) includes simultaneous administration of the two antagonists in the same or different dosage form, or separate administration of the two antagonist (e.g., sequential administration). Thus, the PD-1 antagonist (e.g., antibody) and TIM-4 antagonist (e.g., antibody) can be simultaneously administered in a single formulation. Alternatively, the PD-1 antagonist and TIM-4 antagonist can be formulated for separate administration and are administered concurrently or sequentially.

For example, the PD-1 antagonist can be administered first followed by (e.g., immediately followed by) the administration of the TIM-4 antagonist, or vice versa. In one embodiment, the PD-1 antagonist is administered prior to administration of the TIM-4 antagonist, e.g., the PD-1 antagonist is infused into the patient first, followed from 10 minutes to 3 hours later by an infusion of the TIM-4 antagonist. In one embodiment, the TIM-4 antagonist is administered prior to administration of the PD-1 antagonist, e.g., the TIM-4 antagonist is infused into the patient first, followed from 10 minutes to 3 hours later by an infusion of the PD-1 antagonist. Such concurrent or sequential administration preferably results in both antagonists being simultaneously present in treated patients. In another embodiment, the TIM-4 antagonist and the PD-1 antagonist are administered simultaneously.

In one embodiment, a subject is administered a single dose of a TIM-4 antagonist and a single dose of the PD-1 antagonist, e.g., an anti-PD-1 or anti-PD-L1 antibody. In certain embodiments, multiple (e.g., 2, 3, 4, 5, 6, 7, 8, 9, 10 or more) doses of a TIM-4 antagonist and multiple (e.g., 2, 3, 4, 5, 6, 7, 8, 9, 10 or more) doses of a PD-1 antagonist are administered to a subject in need of treatment. Administration of the TIM-4 antagonist and the PD-1 antagonist may be on the same day, or alternatively, the TIM-4 antagonist may be administered 1 or more days before or after the PD-1 antagonist.

In one embodiment, administrations of a TIM-4 antagonist and a PD-1 antagonist may be done weekly or monthly, in which regimen, they may be administered on the same day (e.g., simultaneously), or one after the other (e.g., one or more minutes, hours or days before or after one another). In one embodiment, the TIM-4 antagonist and PD-1 antagonist are administered every three days.

In one embodiment, the dose of the PD-1 antagonist and/or TIM-4 antagonist is varied over time. For example, the PD-1 antagonist and/or TIM-4 antagonist may be initially administered at a high dose and may be lowered over time. In another embodiment, the PD-1 antagonist and/or TIM-4 antagonist is initially administered at a low dose and increased over time.

In another embodiment, the amount of the PD-1 antagonist and/or TIM-4 antagonist administered is constant for each dose. In another embodiment, the amount of the PD-1 antagonist and/or TIM-4 antagonist varies with each dose. For example, the maintenance (or follow-on) dose of the antagonist can be higher or the same as the loading dose which is first administered. In another embodiment, the maintenance dose of the antagonist a can be lower or the same as the loading dose. A clinician may utilize preferred dosages as warranted by the condition of the patient being treated. The dose may depend upon a number of factors, including stage of disease, etc. The specific dose that should be administered based upon the presence of one or more of such factors is within the skill of the artisan. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. Intermittent therapy (e.g., one week out of three weeks or three out of four weeks) may also be used.

In one embodiment, the TIM-4 antagonist (e.g., antibody) is administered at a dose of 0.1, 0.3, 1, 2, 3, 4, 5, 6, 7, 8, 9, or 10 mg/kg body weight. In another embodiment, the PD-1 antagonist (e.g., antibody) is administered at a dose of 0.5, 1, 2, 3, 4, 5, 6, 7, 8, 9, or 10 mg/kg body weight. Generally, 200 µg/mouse is approximately 10 mg/kg and 100 µg/mouse is approximately 5 mg/kg. Therefore, based on the experiments described herein, one or more doses of 1-20 mg/kg body weight, 1-10 mg/kg body weight, 5-20 mg/kg body weight or 5-10 mg/kg body weight of a TIM-4 antagonist and PD-1 antagonist may be administered to a subject. In certain embodiments, a dose of 0.3 mg/kg to 10 mg/kg body weight of a TIM-4 antagonist is used and a dose of at least 1 mg/kg, e.g., 1-10 mg/kg body weight of a PD-1 antagonist is used.

VIII. Outcomes

Patients, e.g., humans, treated according to the methods disclosed herein preferably experience improvement in at least one sign of cancer. In one embodiment, improvement is measured by a reduction in the quantity and/or size of measurable tumor lesions. In another embodiment, lesions can be measured on chest x-rays or CT or MRI films. In another embodiment, cytology or histology can be used to evaluate responsiveness to a therapy.

In one embodiment, the patient treated exhibits a reduction in size of a tumor, reduction in number of metastasic lesions over time, complete response, partial response, and stable disease. In another embodiment, the patient treated experiences tumor shrinkage and/or decrease in growth rate, i.e., suppression of tumor growth. In another embodiment, unwanted cell proliferation is reduced or inhibited. In yet another embodiment, one or more of the following can occur: the number of cancer cells can be reduced; tumor size can be reduced; cancer cell infiltration into peripheral organs can be inhibited, retarded, slowed, or stopped; tumor metastasis can be slowed or inhibited; tumor growth can be inhibited; recurrence of tumor can be prevented or delayed; one or more of the symptoms associated with cancer can be relieved to some extent.

In another embodiment, the methods of treatment produce a comparable clinical benefit rate (CBR=CR (complete response), PR (partial response) or SD (stable disease) ≥6 months) better than that achieved by a PD-1 (e.g., antibody) or TIM-4 antagonist (e.g., antibody) alone. In other embodiments, the improvement of clinical benefit rate is about 10%, 20%, 30%, 40%, 50%, 60%, 70%, 80% or more, e.g., compared to treatment with a PD-1 antagonist or TIM-4 antagonist alone or relative to tumor growth on the first day of treatment or immediately before initiation of treatment.

In another embodiment, administration of a PD-1 antagonist and a TIM-4 antagonist results in at least a three-fold reduction (e.g., a 3.5-fold reduction) in tumor volume, e.g., relative to treatment with the PD-1 antagonist or the TIM-4 antagonist alone or relative to tumor growth on the first day of treatment or immediately before initiation of treatment.

In a further embodiment, administration of a PD-1 antagonist and a TIM-4 antagonist results in tumor growth inhibition of at least 80%, e.g., relative to treatment with the PD-1 antagonist or TIM-4 antagonist alone or relative to tumor growth on the first day of treatment or immediately before initiation of treatment.

In certain embodiments, administration of a PD-1 antagonist and a TIM-4 antagonist reduces tumor mass by at least 10%, 20%, 30%, 40%, 50%, 60%, 70%, 80%, 90%, 95%, 99% relative to the tumor mass prior to initiation of the treatment or on the first day of treatment.

In some embodiment, the tumor mass is no longer detectable following treatment as described herein. In some embodiments, a subject is in partial or full remission. In certain embodiments, a subject has an increased overall survival, median survival rate, and/or progression free survival.

IX. Kits and Unit Dosage Forms

Also provided herein are kits which include a pharmaceutical composition containing (a) a PD-1 antagonist and (b) a TIM-4 antagonist and a pharmaceutically-acceptable carrier, in a therapeutically effective amount adapted for use in the preceding methods. In one embodiment, the PD-1 antagonist is an antibody (e.g., 5C4 or 12A4, respectively). In another embodiment, the TIM-4 antagonist is an antibody. The kits optionally also can include instructions, e.g., comprising administration schedules, to allow a practitioner (e.g., a physician, nurse, or patient) to administer the composition contained therein to a patient having cancer. The kit also can include a syringe.

Optionally, the kits include multiple packages of the single-dose pharmaceutical compositions each containing an effective amount of the PD-1 antagonist and the TIM-4 antagonist for a single administration in accordance with the methods provided above. Instruments or devices necessary for administering the pharmaceutical composition(s) also may be included in the kits. For instance, a kit may provide one or more pre-filled syringes containing an amount of the PD-1 antagonist and the TIM-4 antagonist.

In one embodiment, the present invention provides a kit for treating cancer in a patient, the kit comprising:
(a) a dose of a PD-1 antagonist;
(b) a dose of a TIM-4 antagonist; and
(c) instructions for using the PD-1 antagonist and TIM-4 antagonist in the methods described herein.

In one embodiment, the present invention provides a kit for treating cancer in a patient, the kit comprising:
(a) one or more doses of a PD-1 antagonist;
(b) one or more doses of a TIM-4 antagonist; and
(c) instructions for using the PD-1 antagonist and TIM-4 antagonist in the methods described herein.

In certain embodiments, the TIM-4 antagonist is an antibody. In certain embodiments, the PD-1 antagonist is an antibody. In particular embodiments, the PD-1 antagonist is an anti-PD-1 antibody comprising the CDR1, CDR2 and CDR3 domains in a heavy chain variable region having the sequence set forth in SEQ ID NO: 13, and the CDR1, CDR2 and CDR3 domains in a light chain variable region having the sequence set forth in SEQ ID NO: 15. In another particular embodiment, the PD-1 antagonist is an anti-PD-L1 antibody comprising antibody comprises the CDR1, CDR2 and CDR3 domains in a heavy chain variable region having the sequence set forth in SEQ ID NO: 1, and the CDR1, CDR2 and CDR3 domains in a light chain variable region having the sequence set forth in SEQ ID NO: 3.

The following examples are merely illustrative and should not be construed as limiting the scope of this disclosure in any way as many variations and equivalents will become apparent to those skilled in the art upon reading the present disclosure.

The contents of all references, Genbank entries, patents and published patent applications cited throughout this application are expressly incorporated herein by reference.

EXAMPLES

Materials and Methods

Animals Ten to eleven-week-old female C57/BL6 mice (Harlan) were used in the studies. Mice received food and water ad libitum and were maintained in a controlled environment according to Association for Assessment and Accreditation of Laboratory Animal Care (AAALAC) International regulations. All animal studies have been approved by the appropriate ethics committee and have therefore been performed in accordance with the ethical standards laid down in the 1964 Declaration of Helsinki and its later amendments.

Antibodies

Anti-mouse PD-1 mAb (anti-mPD-1 mAb) clone 4H2, mouse IgG1 isotype was produced and purified by Bristol-Myers Squibb (Biologics Discovery, CA). The anti-TIM-4 mAb, RMT4-53 has been previously described (Yeung et al., *J. Immunol.* 2009; 191:4447-4455). Briefly, Sprague Dawley rats were immunized with a TIM-4-Ig fusion protein containing the extracellular domain of murine TIM-4 (aa 1-288) to the Fc portion of mouse IgG2a, and fusing LN cells with P3U1 myeloma cells. RMT4-53 reacts with TIM-4/NRK cells but not with parental NRK or other transfected TIM family (TIM-1 B6/NRK, TIM-1 BALB/NRK, TIM-2/NRK, TIM-3 B6/NRK, TIM-3 BALB/NRK) cells. Antibodies were certified to have <0.5 EU/mg endotoxin levels, >95% purity and <5% high molecular weight species. Stock solutions of anti-mPD-1 mAb (clone 4H2; mouse IgG1) and anti-mTIM-4 antibody (clone RM 4-53; rat IgG2a), were kept at 4° C. prior to use. Dosing solutions of anti-mPD-1 mAb and anti-mTIM-4 mAb were prepared in sterile phosphate buffered saline (pH 7.0) and maintained at 4° C.

Cell Lines

CT-26 is an undifferentiated colon carcinoma cell line with a fibroblast morphology (ATCC). Mice inoculated subcutaneously develop lethal tumors at 80% frequency with $10^3$ cells and at 100% with $10^4$ cells. Pulmonary metastases develop when mice are inoculated, intravenously, with $10^4$ cells (Wang et al. *J. Immunol.* 1995; 154:4685-4692). The MC38 cell line was derived from C57BL6 murine colon adenocarcinoma cells (CD44+ ALDH1+) with an epithelial morphology.

Expression of TIM-4

Expression of TIM-4 on mouse peritoneal macrophages and TAMs was confirmed by flow cytometry.

Immunohistochemistry

Immunohistochemical analysis using Rabbit anti-TIM4 (Atlas Antibodies, HPA015625) demonstrated expression of TIM-4 on tissue resident macrophages present in human tonsil, lung and liver. Expression was demonstrated on fixed tissue was sectioned and applied to Superfrost Plus glass slides at a thickness of 5 microns. Sections were allowed to dry overnight at room temperature. Tissues were then deparaffinized in xylene followed by hydration to distilled water in graded series of ethanol. Antigen Retrieval was performed using HIER with Biocare Medical EDTA, pH 8.2 (1×) at approximately 115° C. for 1 minute and then cooled for 20 minutes at RT. Sections were rinsed in TNT Buffer (TBS+ 0.5% Tween) and isolated using a PAP pen. Blocking was performed with Biocare Medical Background Sniper for 30 minutes at RT, followed by 1×TNT Buffer rinse, incubation in Dako Peroxidase Block for 10 minutes at RT and 2×TNT Buffer rinses. Primary Antibody staining was performed using a 1/1000 dilution in Biocare Medical Renaissance antibody diluent and background reducer for 60 minutes at RT and 3×TNT Buffer rinses. Detection antibody was applied using appropriate number of drops to cover section with Biocare Medical MACH3 Rabbit polymer-HRP and incubating for 30 minutes at RT followed by and 3×TNT Buffer rinses. Samples were incubated with Biocare Medical Betazoid DAB and reaction stopped by placing slides in water). Sections were counterstained in Hematoxylin, Leica for 30 seconds, washed in tap water, incubated in Bluing Solution for 45 seconds to 1 minute, washed 2× in water, dehydrated in graded series of alcohol, and Xylene and then mounted.

Example 1: Inhibition of Efferocytosis by Anti-TIM-4 Antibody

Thymocytes were isolated from BALB/c mice and cultured with or without dexamethasone for 4 hours to induce apoptosis. Cells were then incubated with pHrodo dye for 5-10 minutes according to manufacturer's instructions (Thermofisher Scientific). Briefly, $2 \times 10^7$ cells were washed in media without serum 1× and resuspended in 1 mL of Diluent C (Catalog Number G8278). Cells were then stained by adding 1 mL of 2× dye solution (by adding 4 mL of the PKH26 ethanolic dye solution (Catalog Number P9691) to 1 mL of Diluent C) and mixing sample by pipetting. Incubation was for 5 minutes with periodic mixing. Staining reaction was stopped by adding an equal volume of serum and incubating 1 minute. Cells were then washed 1× in media without serum and 2× in PBS. $3 \times 10^6$ pHrodo-labeled cells were injected i.p. into BALB/c mice and peritoneal macrophages were collected by lavage by injecting 3-5 mL of ice cold PBS+2 mM EDTA into the peritoneal cavity of euthanized mice, palpating the abdomen and then collecting the solution via needle aspiration. Experimental animals were injected with RMT4-53 anti-TIM4 antibody 1 hour prior to injection of the pHrodo-labeled thymocytes T.

The uptake of apoptotic cells by peritoneal macrophages was measured using flow cytometry. Briefly, peritoneal macrophages were washed 2× in PBS, resuspended in 100 µL viability dye (eBioscience) and incubated on ice 15 minutes. Cells were washed 1× in PBS and incubated in FcBlock (BioLegend) for 15 minutes on ice. Cells were then stained with antibodies to CD45 (BD), Tim-4 (BioLegend), CD 11b (BioLegend), CD 206 (BioLegend), and F4/80+ (BioLegend), for 30 minutes on ice. Cells were then washed 1× and resuspended in Perm/Fix. Samples were then collected on a LSR Fortessa X20 (BD). To identify cells that engaged in efferocytosis, CD45+/CD11b+ myeloid cells from the live cell population were gated on. Out of these cells, macrophages that engaged in efferocytosis were defined as F4/80+, OPKH26+. The results are set forth in Table 2.

TABLE 2

| | % Apoptotic Cells |
|---|---|
| Control | 25-40 |
| Control + Dex | 50-70 |
| Experimental + anti-TIM4 | 10-15 |
| Experimental + Dex and TIM-4 | 22-42 |

The results demonstrate an increase in efferocytosis of apoptotic cells (50-70%) relative to non-apoptotic cells (25-40%). The addition of anti-TIM-4 blocking anybody greatly reduced uptake of both viable and apoptotic cells. This demonstrates that TIM-4 is an important mediator of cellular uptake.

Example 2: Inhibition of Tumor Growth In Vivo in the CT26 Model by Combination Treatment with Anti-TIM-4 Antibody and Anti-PD-1 Antibody An experiment was conducted in a murine tumor model to test the hypothesis that the combination of anti-TIM-4 and anti-PD-1 would potentiate anti-tumor efficacy. SC CT-26 mice, a colon adenocarcinoma tumor model (TGM-1438), were evaluated for tumor growth after treatment with the anti-TIM4 antibody, RTM-453, alone or in combination with an anti-PD1 antibody, IgG1 D265A.

Female BALB/c mice (Harlan; approximately 8-9 wk old) were subcutaneously implanted with $10^6$ CT-26 cells on day 0. Sixty mice were evaluated by body weight and tumor measurements after 2×/wk dosing according to the following schedule:

TABLE 3

| Dosing Schedule: | | | |
|---|---|---|---|
| Group | N | Treatment | Dosing Regimen |
| 1 | 15 | mIgG1 isotype control mAb | 0.45 mg, IP, d. 7, 10, 13 |
| 2 | 15 | mPD-1 IgG1 D265A mAb + Control mAb | 0.2 + 0.25* mg, IP, d. 7, 10, 13 |
| 4 | 15 | mTIM-4 rat IgG2a mAb + Control mAb | 0.25 + 0.2* mg, IP, d. 7, 10, 13 |
| 6 | 15 | mTIM-4 + mPD-1 mAbs | 0.25 mg + 0.2 mg, IP, d. 7, 10, 13 |

On the days of dosing, the two antibodies were combined and a total of 100 µL of combined antibody was injected into the mice. Spleens and tumors from five mice per group were collected and processed for flow cytometry analysis of tumor infiltrating lymphocytes (TILs), and spleen immune cells on day 16 according to the following protocol: Briefly, cells were resuspended in PBS and aliquoted into plates (spleens $2 \times 10^6$/well, all tumor cells/well) and then were washed 2× in PBS, backspace. Cells were then resuspended in 100 µL viability dye (eBioscience) and incubated on ice 15 minutes. Cells were washed 1× in PBS and incubated in 50 µL FcBlock (BioLegend) for 15 minutes on ice and then stained with 50 µL of antibody stain mix as described below for 30 minutes. Cells were then washed 1× with FACS buffer and resuspended in Perm/Fix. Samples were then collected on a LSR Fortessa X20 (BD).

T Cell Panel

| Fluor | Specificity | Clone | Antibody | Cat# | Company | Ab diln |
|---|---|---|---|---|---|---|
| AlexaFluor 488 (FITC) | CD107a | 1D4B | Alexa Fluor ® 488 anti-mouse CD107a (LAMP-1) Antibody | 121608 | BioLegend | 1:100 |
| PE | CD115 | AFS98 | PE anti-mouse CD115 (CSF-1R) Antibody | 135506 | BioLegend | 1:100 |

| Fluor | Specificity | Clone | Antibody | Cat# | Company | Ab diln |
|---|---|---|---|---|---|---|
| PerCP-Cy5.5 | CD49b | DX5 | PerCp/Cy5.5 anti-mouse CD49b (pan-NK cells) antibody | 108916 | BioLegend | 1:100 |
| BUV 395 | CD45 | 30-F11 | BUV395 rat anti-mouse CD45 antibody | 564279 | eBioscience | 1:100 |
| BV 421 | CD8 | 53-6.7 | Brilliant Violet 421 ™ anti-mouse CD8a antibody | 100738 | BioLegend | 1:200 |
| BV 510 | CD4 | RM4-5 | Brilliant Violet 510 ™ anti-mouse CD4 antibody | 100553 | BioLegend | 1:200 |
| BV 605 | Thy1.2 | 53-2.1 | Brilliant Violet 605 ™ anti-mouse CD90.2 (Thy-1.2) antibody | 140317 | BioLegend | 1:200 |
| BV 711 | CD62L | MEL-14 | Brilliant Violet 711 ™ anti-mouse CD62L antibody | 104445 | BioLegend | 1:200 |
| BV 785 | CD44 | IM7 | Brilliant Violet 785 ™ anti-mouse CD44 antibody | 103041 | BioLegend | 1:200 |
| APC | FoxP3 | FJK-16S | Anti-Mouse/Rat Foxp3 APC | 17-5773-80B | eBioscience | 1:100 |
| PE-Cy7 | Ki-67 | SoIA15 | Anti-Mouse/Rat Ki-67 PE-Cyanine7 | 25-5698-82 | eBioscience | 1:100 |
| APC eFluor 780 (APC-Cy7) | Fixable Viability Dye | n/a | eFluor ® 780 Fixable Viability Dye | 65-0865-14 | eBioscience | 1:1000 |
| FC Block | block | 93 | TruStain FcX anti-mouse CD16/32 | 101320 | BioLegend | |

Ki-67+ to assess proliferating cells;
CD44/CD62L analysis to determine subset T cells into naïve, activated, and memory T cell subsets;
FoxP3 to assess population of Tregs (FoxP3+CD4+ T cells);
CD8+CD107a+ to assess degranulating CD8+ T cells (Antigen/Tumor-specific CTL)

Myeloid Panel

| Fluor | Specificity | Clone | Antibody | Cat# | Company | |
|---|---|---|---|---|---|---|
| AlexaFluor 488 (FITC) | CD11c | N418 | FITC anti-mouse CD11c Antibody | 117306 | BioLegend | 1:100 |
| PE | CD115 | AFS98 | PE anti-mouse CD115 (CSF-1R) Antibody | 135506 | BioLegend | 1:100 |
| PerCP-Cy5.5 | CD49b | DX5 | PerCp/Cy5.5 anti-mouse CD49b (pan-NK cells) antibody | 108916 | BioLegend | 1:100 |
| BUV 395 | CD45 | 30-F11 | BUV395 rat anti-mouse CD45 antibody | 564279 | eBioscience | 1:100 |
| BV 421 | Ly6C | HK1.4 | Brilliant Violet 421 ™ anti-mouse Ly6C antibody | 128032 | BioLegend | 1:200 |
| BV 605 | Thy 1.2 (CD90.2) | 53-2.1 | Brilliant Violet 605 ™ anti-mouse Thy-1.2 antibody | 140317 | BioLegend | 1:200 |
| BV 711 | Gr-1 | RB6-8C5 | Brilliant Violet 711 ™ anti-mouse GR-1 antibody | 104731 | BioLegend | 1:200 |
| BV 785 | F4-80 | BM8 | Brilliant Violet 785 ™ anti-mouse F4/80 antibody | 123141 | BioLegend | 1:200 |
| APC | Ly6G | 1A8 | APC anti-mouse Ly6G antibody | 127614 | BioLegend | 1:200 |
| AF-700 | CD11b | M1/70 | Alexa Fluor 700 anti-mouse/human CD11b antibody | 101222 | BioLegend | 1:100 |
| PE-Cy7 | MHCII | M5/114.15.2 | PE-Cy7 anti-mouse I-A/I-E antibody | 107630 | eBioscience | 1:100 |
| APC eFluor 780 (APC-Cy7) | Fixable Viability Dye | n/a | eFluor ® 780 Fixable Viability Dye | 65-0865-14 | eBioscience | 1:1000 |
| FC Block | block | 93 | TruStain FcX anti-mouse CD16/32 | 101320 | BioLegend | |

Myeloid Cell subsetting for TAMs, MDSCs, NK cells, B cells
CD80, CD86 staining for activated APCs The myeloid populations in spleen and tumors are shown in FIG. 3. The CD8+ T cell populations in spleen and tumor infiltrating lymphocytes are shown in FIG. 4. The CD4+ cell populations in spleen and tumor infiltrating lymphocytes are shown in FIG. 5. The data demonstrate a shift in myeloid cell populations, and an increase in activated T cells in tumor infiltrating lymphocytes.

The remaining ten mice per group were monitored for tumor growth. Tumor size and body weights were measured twice weekly. Tumor size (measured as $mm^3$) was calculated by multiplying the tumor length by the square of the tumor width divided by 2. Treatments were initiated when subcutaneous tumors reached a median size of 200 $mm^3$ (established model).

Figure 7B:
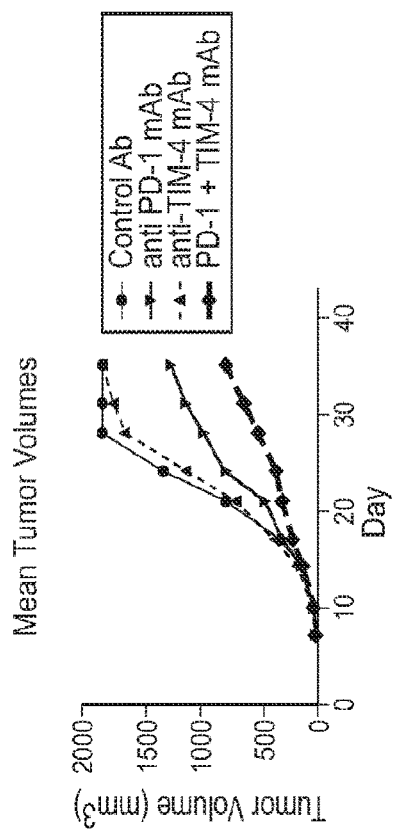
FIG. 7A-B are graphs depicting the mean and median tumor volume ($mm^3$) in mice after administration of a control, an TIM-4 antagonist antibody, an anti-PD-1 antibody, or a combination of an anti-PD-1 antibody and an anti-TIM-4 antibody.
Figure 7A:
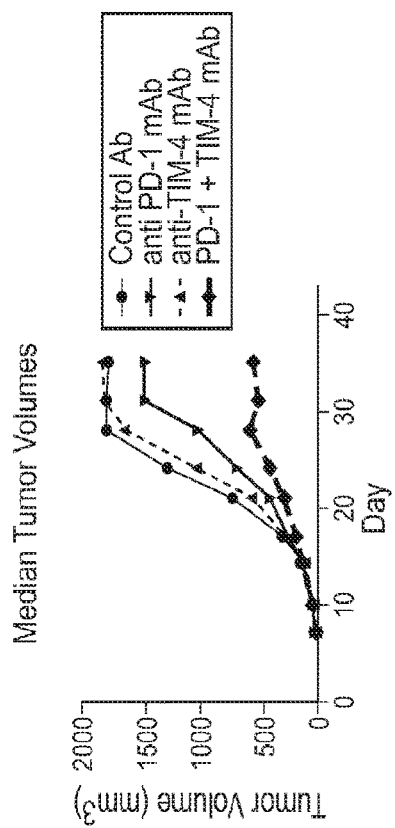
Figure 8:
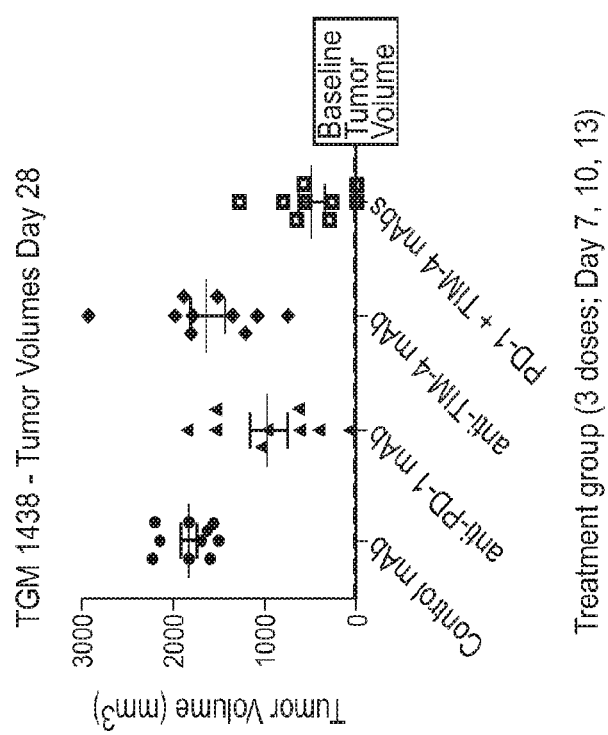
FIG. 8 is a graph depicting the tumor volumes at day 28 in mice ($mm^3$) in mice after administration of a control, an TIM-4 antagonist antibody, an anti-PD-1 antibody, or a combination of an anti-PD-1 antibody and an anti-TIM-4 antibody.
Figures 9A, 9B:
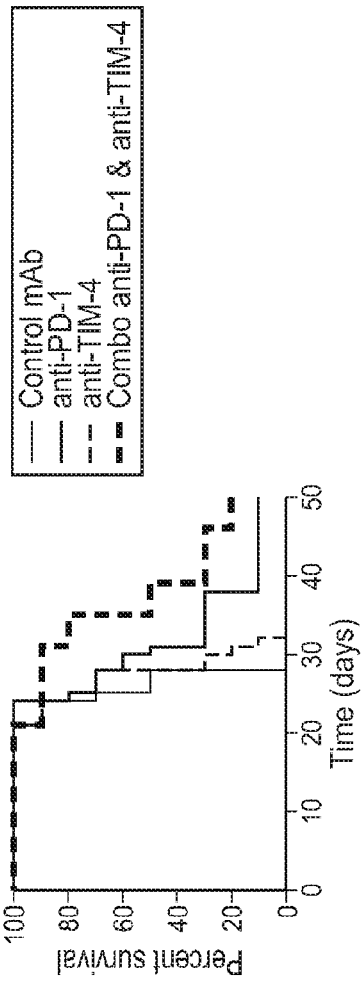
FIG. 9A is a graph depicting the survival rates of mice after administration of a control, an TIM-4 antagonist antibody, an anti-PD-1 antibody, or a combination of an anti-PD-1 antibody and an anti-TIM-4 antibody in the CT26 animal model.
FIG. 9B is a table indicating the median survival rate of each treatment group.

Anti-TIM-4 antibody administered in combination with anti-PD-1 antibody provided enhanced anti-tumor activity above the activity of either agent alone. The combination demonstrated decreased tumor growth rates (FIGS. 6-8), and an increased overall survival rate (FIG. 9). In sum, the combination of the TIM-4 mAb and the PD-1 mAb resulted in synergistic activity compared to the activity elicited by single agents alone. Therefore, results from this study demonstrate that a combination regimen of anti-mTIM-4 mAb and PD-1 mAb is well-tolerated and result in marked antitumor activity.

Example 3: Inhibition of Tumor Growth In Vivo in the MC38 Model by Combination Treatment with Anti-TIM-4 Antibody and Anti-PD-1 Antibody MC38 mice, a colon adenocarcinoma tumor model, were evaluated for tumor growth after treatment with the anti- TIM4 antibody, RTM-453, alone or in combination with an anti-PD1 antibody, IgG1 D265A.

Female C57/BL6 mice (Harlan; approximately 8-9 wk old) were subcutaneously implanted with $10^6$ MC38 cells on day 0. Mice were dosed beginning on Day 6. Three doses at 200 µg/injection were administered IP every 4th day. When the two antibodies were administered to a mouse, the antibodies were first combined, and administered together into the mouse. Tumors were measured using calipers and tumor volumes calculated using the formula (L2×W)/2. Progression Free Survival defined as # of days for tumor to reach 4× initial tumor volume.

Figure 10:
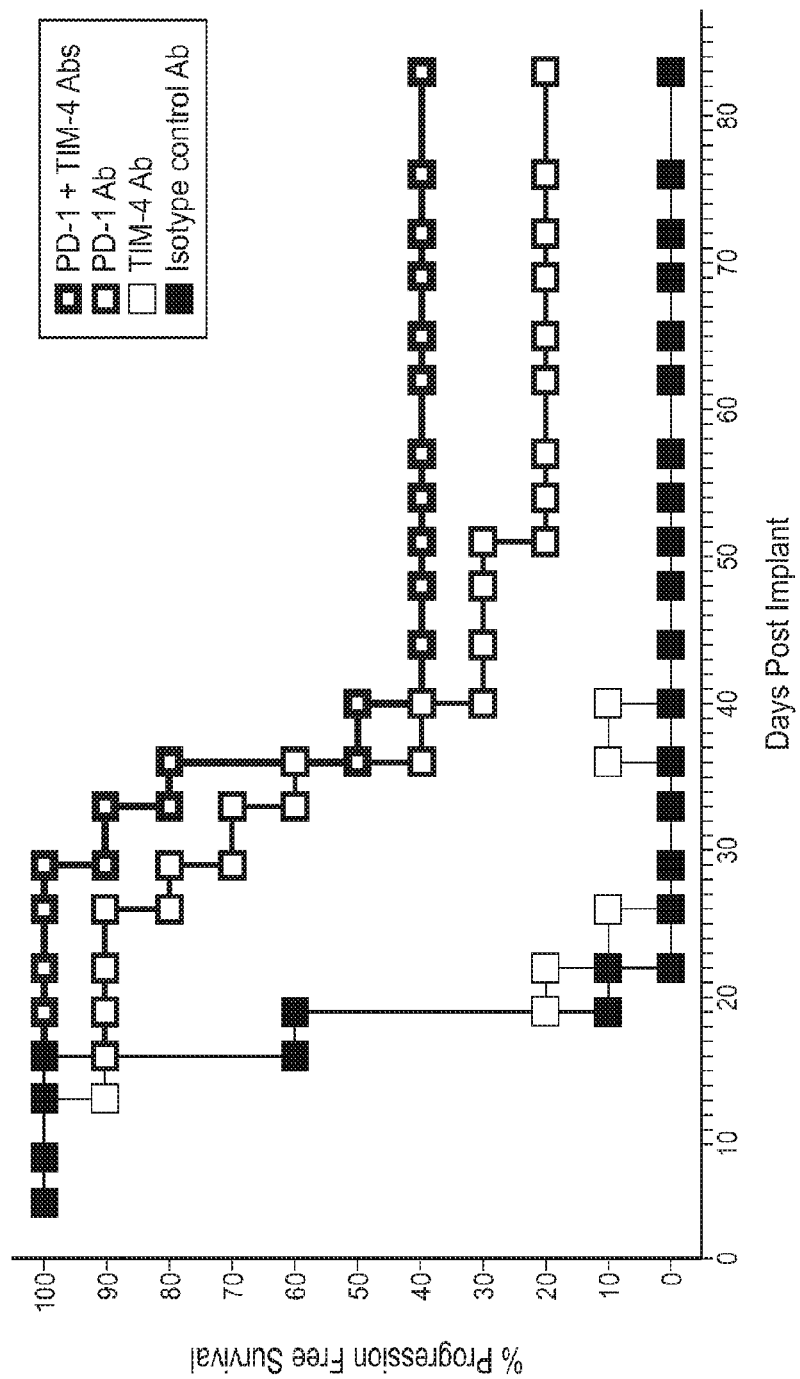
FIG. 10 is a graph depicting the percentage progression free survival rates of mice after administration of a control, an TIM-4 antagonist antibody, an anti-PD-1 antibody, or a combination of an anti-PD-1 antibody and an anti-TIM-4 antibody in the MC38 animal model.
Figure 11:
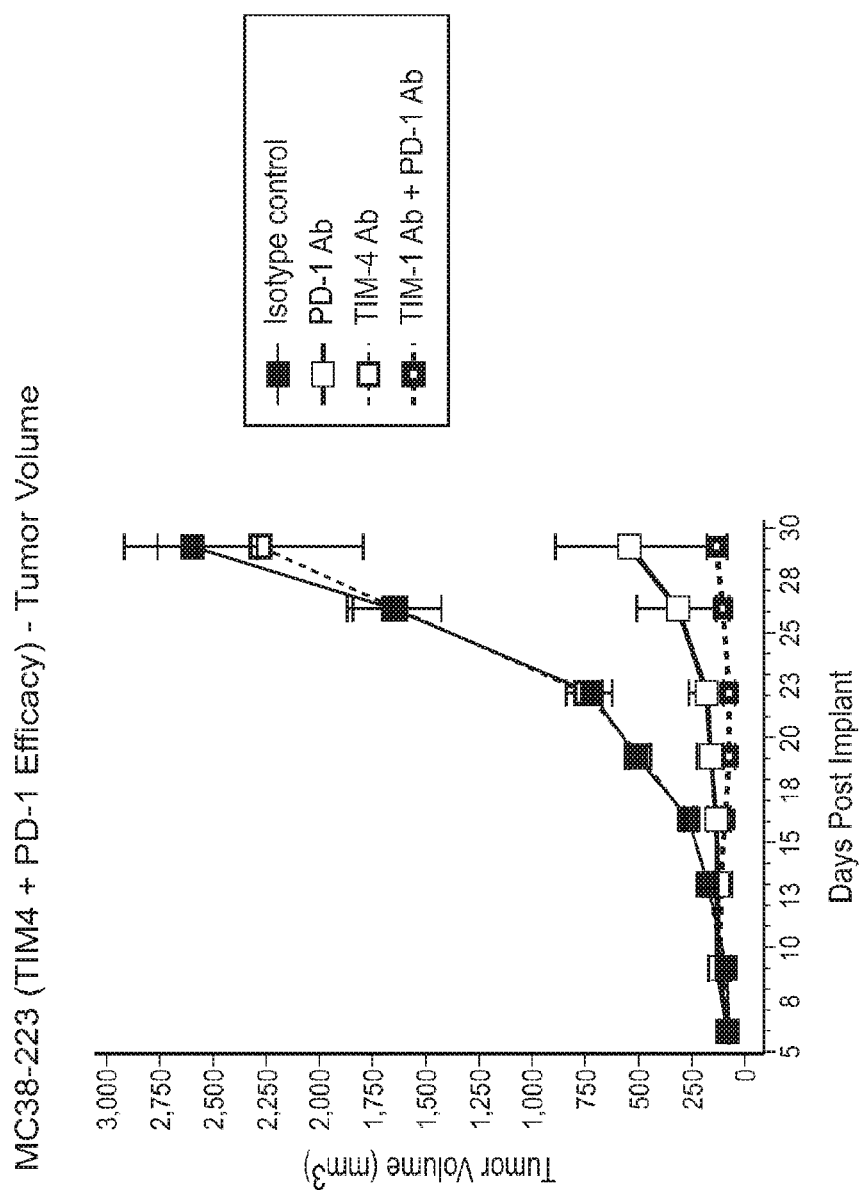
FIG. 11 shows the mean tumor volume relative to the days post implant in the mice that were in the experiment shown in FIG. 10.
Figure 12A:
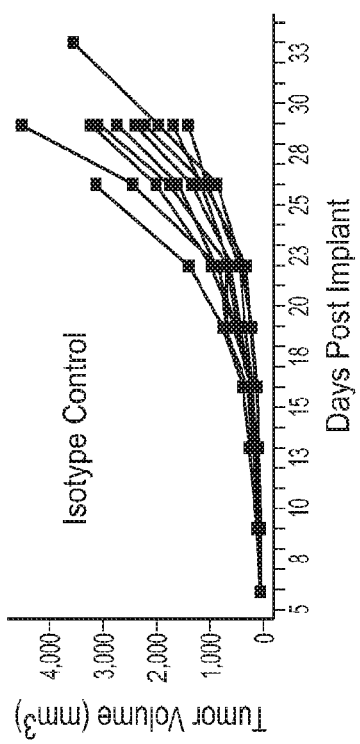
FIG. 12A-C shows the individual tumor volumes relative to the days post implant in the mice that were in the experiment shown in FIGS. 10 and 11.
Figure 12C:
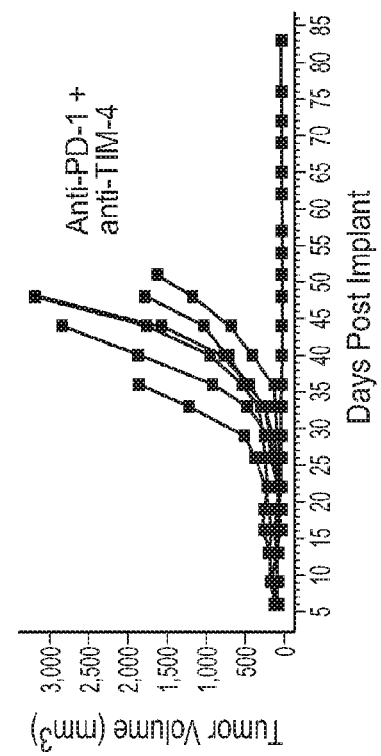
Figure 12B:
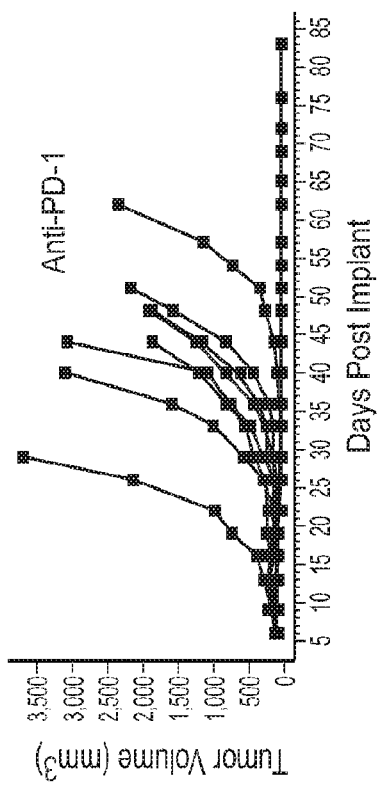

The results are provided in FIGS. 10, 11 and 12, and Table X. FIG. 10, which provides the percentage of progression free survival relative to the days post implant, show that administration of the combination of the anti-PD-1 and anti-TIM4 antibodies results in a higher percentage of progression free survival relative to each antibody separately and relative to the isotype control. Table X shows that the combination treatment provided more complete regressions relative to each antibody separately and relative to the isotype control. FIG. 11, which shows the MC38 mean tumor volume relative to the days post implant, indicates that the combination treatment reduced the mean tumor volume more relative to each antibody separately and relative to the isotype control. FIG. 12A-C shows the MC38 individual tumor volumes, and confirms the results shown in the FIGS. 10, 11 and Table X.

TABLE 5

Number of mice with complete regressions of tumors

| Treatment | Complete Regressions |
| --- | --- |
| Isotype Control | 0/10 |
| Anti-PD1 Alone | 2/10 |
| anti-TIM4 (RMT4-53 mIgG1 D265A) Alone | 0/10 |
| Anti-PD1 + anti-TIM4 (RMT4-53 mIgG1 D265A) | 4/10 |

Thus, administration of a combination of an anti-TIM4 antibody with an anti-PD-1 antibody in the CT26 and MC39 animal models resulted in a stronger anti-tumor effect relative to each antibody alone.

SUMMARY OF THE SEQUENCE LISTING

| SEQ ID NO: | SEQUENCE |
| --- | --- |
| 1 | Heavy Chain Variable Region (VH) Amino Acid Sequence Anti-PD-L1 mAb (12A4; 12A4 in WO 2007/005874 and U.S. Pat. No. 7,943,743) QVQLVQSGAEVKKPGSSVKVSCKTSGDTFSTYAISWVRQAPGQGLEWMGGII PIFGKAHYAQKFQGRVTITADESTSTAYMELSSLRSEDTAVYFCARKFHFVS GSPFGMDVWGQGTTVTVSS |
| 2 | Heavy Chain Variable Region (VH) Nucleotide Sequence Anti-PD-L1 mAb (12A4; 12A4 in WO 2007/005874 and U.S. Pat. No. 7,943,743) cag gtc cag ctg gtg cag tct ggg gct gag gtg aag aag cct ggg tcc tcg gtg aag gtc tcc tgc aag act tct gga gac acc ttc agc acc tat gct atc agc tgg gtg cga cag gcc cct gga caa ggg ctt gag tgg atg gga ggg atc atc cct ata ttt ggt aaa gca cac tac gca cag aag ttc cag ggc aga gtc acg att acc gcg gac gaa tcc acg agc aca gcc tac atg gag ctg agc agc ctg aga tct gag gac acg gcc gtg tat ttt tgt gcg aga aag ttt cac ttt gtt tcg ggg agc ccc ttc ggt atg gac gtc tgg ggc caa ggg acc acg gtc acc gtc tcc |
| 3 | Light Chain Variable Region (VL) Amino Acid Sequence Anti-PD-L1 mAb (12A4; 12A4 in WO 2007/005874 and U.S. Pat. No. 7,943,743) EIVLTQSPATLSLSPGERATLSCRASQSVSSYLAWYQQKPGQAPRLLIY DASNRATGIPARFSGSGSGTDFTLTISSLEPEDFAVYYCQQRSNWPTFG QGTKVEIK |
| 4 | Light Chain Variable Region (VL) Nucleotide Sequence Anti-PD-L1 mAb (12A4; 12A4 in WO 2007/005874 and U.S. Pat. No. 7,943,743) gaa att gtg ttg aca cag tct cca gcc acc ctg tct ttg tct cca ggg gaa aga gcc acc ctc tcc tgc agg gcc agt cag agt gtt agc agc tac tta gcc tgg tac caa cag aaa cct ggc cag gct ccc agg ctc ctc atc tat gat gca tcc aac agg gcc act ggc atc cca gcc agg ttc agt ggc agt ggg tct ggg aca gac ttc act ctc acc atc agc agc cta gag cct gaa gat ttt gca gtt tat tac tgt cag cag cgt agc aac tgg ccg acg ttc ggc caa ggg acc aag gtg gaa atc aaa |
| 5 | Heavy Chain CDR1 Amino Acid Sequence Anti-PD-L1 mAb (12A4; 12A4 in WO 2007/005874 and U.S. Pat. No. 7,943,743) TYAIS |
| 6 | Heavy Chain CDR2 Amino Acid Sequence Anti-PD-L1 mAb (12A4; 12A4 in WO 2007/005874 and U.S. Pat. No. 7,943,743) GIIPIFGKAHYAQKFQ |

SUMMARY OF THE SEQUENCE LISTING

| SEQ ID NO: | SEQUENCE |
|---|---|
| 7 | Heavy Chain CDR3 Amino Acid Sequence<br>Anti-PD-L1 mAb (12A4; 12A4 in WO 2007/005874 and U.S. Pat. No. 7,943,743)<br>KFHFVSGSPFGMDV |
| 8 | Light Chain CDR1 Amino Acid Sequence<br>Anti-PD-L1 mAb (12A4; 12A4 in WO 2007/005874 and U.S. Pat. No. 7,943,743)<br>RASQSVSSYLA |
| 9 | Light Chain CDR2 Amino Acid Sequence<br>Anti-PD-L1 mAb (12A4; 12A4 in WO 2007/005874 and U.S. Pat. No. 7,943,743)<br>DASNRAT |
| 10 | Light Chain CDR3 Amino Acid Sequence<br>Anti-PD-L1 mAb (12A4; 12A4 in WO 2007/005874 and U.S. Pat. No. 7,943,743)<br>QQRSNWPT |
| 11 | Heavy Chain Amino Acid Sequence<br>Anti-PD-1 mAb (5C4 in WO 2006/121168)<br>(variable region underlined; constant region bold)<br>QVQLVESGGGVVQPGRSLRLDCKASGITFSNSGMHWVRQAPGKGL EWVAVIWYDGSKRYYADSVKGRFTISRDNSKNTLFLQMNSLRAEDT AVYYCATNDDYWQGTLVTVSSASTKGPSVFPLAPCSRSTSESTAA LGCLVKDYFPEPVTVSWNSGALTSGVHTFPAVLQSSGLYSLSSVVT VPSSSLGTKTYTCNVDHKPSNTKVDKRVESKYGPPCPPCPAPEFLG GPSVFLFPPKPKDTLMISRTPEVTCVVVDVSQEDPEVQFNWYVDGV EVHNAKTKPREEQFNSTYRVVSVLTVLHQDWLNGKEYKCKVSNKG LPSSIEKTISKAKGQPREPQVYTLPPSQEEMTKNQVSLTCLVKGFYPS DIAVEWESNGQPENNYKTTPPVLDSDGSFFLYSRLTVDKSRWQEGNV FSCSVMHEALHNHYTQKSLSLSLGK |
| 12 | Light Chain Amino Acid Sequence<br>Anti-PD-1 mAb (5C4 in WO 2006/121168)<br>(variable region underlined; constant region bold)<br>EIVLTQSPATLSLSPGERATLSCRASQSVSSYLAWYQQKPGQAPRLLI YDASNRATGIPARFSGSGSGTDFTLTISSLEPEDFAVYYCQQSSNWPR TFGQGTKVEIKRTVAAPSVFIFPPSDEQLKSGTASVVCLLNNFYPREA KVQWKVDNALQSGNSQESVTEQDSKDSTYSLSSTLTLSKADYEKHK VYACEVTHQGLSSPVTKSFNRGEC |
| 13 | Heavy Chain Variable Region (VH) Amino Acid Sequence<br>Anti-PD-1 mAb (5C4 in WO 2006/121168)<br>(SEQ ID NO: 4 from WO 2006/121168)<br>QVQLVESGGGVVQPGRSLRLDCKASGITESNSGMHWVRQAPGKGLEWVAV IWYDGSKRYYADSVKGRFTISRDNSKNTLFLQMNSLRAEDTAVYYCATND DYWGQGTLVTVSS |
| 14 | Heavy Chain Variable Region (VH) Nucleotide Sequence<br>Anti-PD-1 mAb (5C4 in WO 2006/121168)<br>(SEQ ID NO: 60 from WO 2006/121168)<br>cag gtg cag ctg gtg gag tct ggg gga ggc gtg gtc cag cct ggg agg tcc<br>ctg aga ctc gac tgt aaa gcg tct gga atc acc ttc agt aac tct ggc atg<br>cac tgg gtc cgc cag gct cca ggc aag ggg ctg gag tgg gtg gca gtt att<br>tgg tat gat gga agt aaa aga tac tat gca gac tcc gtg aag ggc cga ttc<br>acc atc tcc aga gac aat tcc aag aac acg ctg ttt ctg caa atg aac<br>agc ctg aga gcc gag gac acg gct gtg tat tac tgt gcg aca<br>aac gac gac tac tgg ggc cag gga acc ctg gtc acc gtc tcc<br>tca |
| 15 | Light Chain Variable Region (VL) Amino Acid Sequence<br>Anti-PD-1 mAb (5C4 in WO 2006/121168)<br>(SEQ ID NO:11 from WO 2006/121168)<br>EIVLTQSPATLSLSPGERATLSCRASQSVSSYLAWYQQKPGQAPRLLIYD ASNRATGIPARFSGSGSGTDFTLTISSLEPEDFAVYYCQQSSNWPRTFGQ GTKVEIK |
| 16 | Light Chain Variable Region (VL) Nucleotide Sequence<br>Anti-PD-1 mAb (5C4 in WO 2006/121168)<br>(SEQ ID NO:67 from WO 2006/121168)<br>gaa att gtg ttg aca cag tct cca gcc acc ctg tct ttg tct cca ggg gaa<br>aga gcc acc ctc tcc tgc agg gcc agt cag agt gtt agt agt tac tta gcc |

SUMMARY OF THE SEQUENCE LISTING

| SEQ ID NO: | SEQUENCE |
|---|---|
|  | tgg tac caa cag aaa cct ggc cag gct ccc agg ctc ctc atc tat gat gca<br>tcc aac agg gcc act ggc atc cca gcc agg ttc agt ggc agt ggg tct ggg<br>aca gac ttc act ctc acc atc agc agc cta gag cct gaa gat ttt gca gtt<br>tat tac tgt cag cag agt agc aac tgg cct cgg acg ttc<br>ggc caa ggg acc aag gtg gaa atc aaa |
| 17 | Heavy Chain CDR1 Amino Acid Sequence<br>Anti-PD-1 mAb (5C4 in WO 2006/121168)<br>(SEQ ID NO: 18 from WO 2006/121168)<br>NSGMH |
| 18 | Heavy Chain CDR2 Amino Acid Sequence<br>Anti-PD-1 mAb (5C4 in WO 2006/121168)<br>(SEQ ID NO: 25 from WO 2006/121168)<br>VIWYDGSKRYYADSVKG |
| 19 | Heavy Chain CDR3 Amino Acid Sequence<br>Anti-PD-1 mAb (5C4 in WO 2006/121168)<br>(SEQ ID NO: 32 from WO 2006/121168)<br>NDDY |
| 20 | Light Chain CDR1 Amino Acid Sequence<br>Anti-PD-1 mAb (5C4 in WO 2006/121168)<br>(SEQ ID NO: 39 from WO 2006/121168)<br>RASQSVSSYLA |
| 21 | Light Chain CDR2 Amino Acid Sequence<br>Anti-PD-1 mAb (5C4 in WO 2006/121168)<br>(SEQ ID NO: 46 from WO 2006/121168)<br>DASNRAT |
| 22 | Light Chain CDR3 Amino Acid Sequence<br>Anti-PD-1 mAb (5C4 in WO 2006/121168)<br>(SEQ ID NO: 53 from WO 2006/121168)<br>QQSSNWPRT |
| 23 | Complete PD-1 sequence (GenBank Accession No.: U64863)<br>agtttccctt ccgctcacct ccgcctgagc agtggagaag gcggcactct ggtggggctg<br>ctccaggcat gcagatccca caggcgcccc ggccagtcgt ctgggcggtg ctacaactgg<br>gctggcggcc aggatggttc ttagactccc cagacaggcc ctggaacccc cccaccttct<br>tcccagccct gctcgtggtg accgaagggg acaacgccac cttcacctgc agcttctcca<br>acacatcgga gagcttcgtg ctaaactggt accgcatgag ccccagcaac cagacggaca<br>agctggccgc cttccccgag gaccgcagcc agcccggcca ggactgccgc ttccgtgtca<br>cacaactgcc caacgggcgt gacttccaca tgagcgtggt cagggcccgg cgcaatgaca<br>gcggcaccta cctctgtggg gccatctccc tggcccccaa ggcgcagatc aaagagagcc<br>tgcgggcaga gctcagggtg acagagagaa gggcagaagt gcccacagcc caccccagcc<br>cctcacccag gccagccggc cagttccaaa ccctggtggt tggtgtcgtg ggcggcctgc<br>tgggcagcct ggtgctgcta gtctgggtcc tggccgtcat ctgctcccgg gccgcacgag<br>ggacaatagg agccaggcgc accggccagc ccctgaagga ggaccccctca gccgtgcctg<br>tgttctctgt ggactatggg gagctggatt tccagtggcg agagaagacc ccggagcccc<br>ccgtgccctg tgtccctgag cagacggagt atgccaccat tgtctttcct agccggaatg<br>gcacctcatc ccccgcccgc aggggctcag ccgacggccc tcggagtgcc agccactga<br>ggcctgagga tggacactgc tcttggcccc tctgaccggc ttccttggcc accagtgttc<br>tgcagaccct ccaccatgag cccggggtcag cgcatttcct caggagaagc aggcagggtg<br>caggccattg caggccgtcc aggggcgtgag ctgcctgggg gcgaccgggg ctccagcctg<br>cacctgcacc aggcacagcc ccaccacagg actcatgtct caatgcccac agtgagccca<br>ggcagcaggt gtcaccgtcc cctacaggga gggcagatg cagtcactgc ttcaggtcct<br>gccagcacag agctgcctgc gtccagctcc ctgaatctct gctgctgctg ctgctgctgc<br>tgctgctgcc tgcggcccgg ggctgaaggc gccgtggcgtc tgcctgacgc cccggagcct<br>cctgcctgaa cttgggggct ggttggagat ggccttggag cagccaaggt gccctggca<br>gtggcatccc gaaacgccct ggacgcaggg cccaagactg ggcacaggag tgggaggtac<br>atgggctggg ggactcccca ggagttatct gctccctgca ggcctagaga gtttcaggg<br>aaggtcagaa gagctcctgg ctgtggtggg cagggcagga aacccctccc acctttacac<br>atgccaggc agcacctcag gccctttgtg gggcagggaa gctgaggcag taagcgggca<br>ggcagagctg gaggcctttc aggccagcca gcactctggc ctcctgccgc cgcattccac<br>cccagcccct cacaccactc gggagaggga catcctacgg tcccaaggtc aggagggcag<br>ggctggggtt gactcaggcc cctcccagct gtggccacct gggtgttggg agggcagaag<br>tgcaggcacc tagggccccc catgtgccca cctgggagc tctccttgga acccattcct<br>gaaattattt aaaggggttg gccgggctcc caccagggcc tgggtgggaa ggtacaggcg<br>ttccccgggg gcctagtacc cccgcgtggc ctatccactc ctcacatcca cacactgcac<br>ccccactcct ggggcagggc caccagcatc caggcgccca gcaggcacct gagtggctgg<br>gacaagggat ccccccttccc tgtggttcta ttatattata attataatta aatatgagag<br>catgct |

-continued

| SEQ ID NO: | SEQUENCE |
|---|---|
| 24 | Human PD-L1 amino acid sequence-isoform a precursor (GenBank Accession No. NP_054862.1)<br>MRIFAVFIFM TYWHLLNAFT VTVPKDLYVV EYGSNMTIEC KFPVEKQLDL AALIVYWEME<br>DKNIIQFVHG EEDLKVQHSS YRQRARLLKD QLSLGNAALQ ITDVKLQDAG VYRCMISYGG<br>ADYKRITVKV NAPYNKINQR ILVVDPVTSE HELTCQAEGY PKAEVIWTSS DHQVLSGKTT<br>TTNSKREEKL FNVTSTLRIN TTTNEIFYCT FRRLDPEENH TAELVIPELP LAHPPNERTH<br>LVILGAILLC LGVALTFIFR LRKGRMMDVK KCGIQDTNSK KQSDTHLEET |
| 25 | Human PD-L1 amino acid sequence-isoform b precursor (GenBank Accession No. NP_001254635.1)<br>MRIFAVFIFM TYWHLLNAPY NKINQRILVV DPVTSEHELT CQAEGYPKAE VIWTSSDHQV<br>LSGKTTTTNS KREEKLFNVT STLRINTTTN EIFYCTFRRL DPEENHTAEL VIPELPLAHP<br>PNERTHLVIL GAILLCLGVA LTFIFRLRKG RMMDVKKCGI QDTNSKKQSD THLEET |
| 26 | Human TIM-4 amino acid sequence-isoform 1<br>(GenBank Accession No. NP_612388.2)<br>MSKEPLILWLMIEFWWLYLTPVTSETVVTEVLGHRVTLPCLYSSWSHNSNSMCWGKDQCPYSOCKEALIR<br>TDGMRVTSRKSAKYRLQGTIPRGDVSLTILNPSESDSGVYCCRIEVPGWFNDVKINVRLNLQRASTTTHR<br>TATTTTRRTTTTSPTTTRQMTTTPAALPTTVVTTPDLTTGTPLQMTTIAVFTTANTCLSLTPSTLPEEAT<br>GLLTPEPSKEGPILTAESETVLPSDSWSSVESTSADTVLLTSKESKVWDLPSTSHVSMWKTSDSVSSPQM<br>GASDTAVPEQNKTTKTGQMDGIPMSMKNEMPISQLLMIIAPSLGFVLFALFVAFLLRGKLMETYCSQKHT<br>RLDYIGDSKNVLNDVQHGREDEDGLFTL |
| 27 | *Homo sapiens* T-cell (TIMD4), transcript variant 1, mRNA<br>(GenBank Accession No. NM_138379.2)<br>ATAAGAGGTTGGGCTTTGGATAGATAGACAGACTCCTGGGTCCGGTCAACCGTCAAAATGTCCAAAGAAC<br>CTCTCATTCTCTGGCTGATGATTGAGTTTTGGTGGCTTTACCTGACACCAGTCACTTCAGAGACTGTTGT<br>GACGGAGGTTTTGGGTCACCGGGTGACTTTGCCCTGTCTGTACTCATCCTGGTCTCACAACAGCAACAGC<br>ATGTGCTGGGGAAAGACCAGTGCCCCTACTCCGGTTGCAAGGAGGCGCTCATCCGCACTGATGGAATGA<br>GGGTGACCTCAAGAAAGTCAGCAAAATATAGACTTCAGGGGACTATCCCGAGAGGTGATGTCTCCTTGAC<br>CATCTTAAACCCCAGTGAAAGTGACAGCGGTGTGTACTGCTGCCGCATAGAAGTGCCTGGCTGGTTCAAC<br>GATGTAAAGATAAACGTGCGCCTGAATCTACAGAGAGCCTCAACAACCACGCACAGAACAGCAACCACCA<br>CCCACACGCAGAACAACAACAACAAGCCCCACCACCACCCGACAACAACCCCAGCTGCACTTCC<br>AACAACAGTCGTGACCACACCCGATCTCACAACCGGAACACCACTCCAGATGACAACCATTGCCGTCTTC<br>ACAACAGCAAACACGTGCCTTTCACTAACCCCAAGCACCCTTCCGGAGGAAGCCACAGGTCTTCTGACTC<br>CCGAGCCTTCTAAGGAAGGGCCCATCCTCACTGCAGAATCAGAAACTGTCCTCCCCAGTGATTCCTGGAG<br>TAGTGTTGAGTCTACTTCTGCTGACACTGTCCTGCTGACATCCAAAGAGTCCAAAGTTTGGGATCTCCCA<br>TCAACATCCCACGTGTCAATGTGGAAAACGAGTGATTCTGTGTCTTCTCCTCAGCCTGGAGCATCTGATA<br>CAGCAGTTCCTGAGCAGAACAAAACAACAAAAACAGGACAGATGGATGGAATACCCATGTCAATGAAGAA<br>TGAAATGCCCATCTCCCAACTACTGATGATCATCGCCCCCTCCTTGGGATTTGTGCTCTTCGCATTGTTT<br>GTGGCGTTTCTCCTGAGAGGGAAACTCATGGAAACCTATTGTTCGCAGAAACACACAAGGCTAGACTACA<br>TTGGAGATAGTAAAAATGTCCTCAATGACGTGCAGCATGGAAGGGAAGACGAAGACGGCCTTTTTACCCT<br>CTAACAACGCAGTAGCATGTTAGATTGAGGATGGGGGCATGACACTCCAGTGTCAAAATAAGTCTTAGTA<br>GATTTCCTTGTTTCATAAAAAAGACTCACTTATTCCATGGATGTCATTGATCCAGGCTTGCTTTAGTTTC<br>ATGAATGAAGGGTACTTTAGAGACCACAACTTCTCTGTCAAAAA |
| 28 | Human TIM-4 amino acid sequence isoform 2<br>(GenBank Accession No. NP_001140198.1)<br>MSKEPLILWLMIEFWWLYLTPVTSETVVTEVLGHRVTLPCLYSSWSHNSNSMCWGKDQCPYSOCKEALIR<br>TDGMRVTSRKSAKYRLQGTIPRGDVSLTILNPSESDSGVYCCRIEVPGWFNDVKINVRLNLQRASTTTHR<br>TATTTTRRTTTTSPTTTRQMTTTPAALPTTVVTTPDLTTGTPLQMTTIAVFTTANTCLSLTPSTLPEEAT<br>GLLTPEPSKEGPILTAESETVLPSDSWSSVESTSADTVLLTSKASDTAVPEQNKTTKTGQMDGIPMSMKN<br>EMPISQLLMIIAPSLGFVLFALFVAFLLRGKLMETYCSQKHTRLDYIGDSKNVLNDVQHGREDEDGLFTL |
| 29 | *Homo sapiens* T-cell (TIMD4), transcript variant 2, mRNA<br>(GenBank Accession No. NM_001146726.1)<br>ATAAGAGGTTGGGCTTTGGATAGATAGACAGACTCCTGGGTCCGGTCAACCGTCAAAATGTCCAAAGAAC<br>CTCTCATTCTCTGGCTGATGATTGAGTTTTGGTGGCTTTACCTGACACCAGTCACTTCAGAGACTGTTGT<br>GACGGAGGTTTTGGGTCACCGGGTGACTTTGCCCTGTCTGTACTCATCCTGGTCTCACAACAGCAACAGC<br>ATGTGCTGGGGAAAGACCAGTGCCCCTACTCCGGTTGCAAGGAGGCGCTCATCCGCACTGATGGAATGA<br>GGGTGACCTCAAGAAAGTCAGCAAAATATAGACTTCAGGGGACTATCCCGAGAGGTGATGTCTCCTTGAC<br>CATCTTAAACCCCAGTGAAAGTGACAGCGGTGTGTACTGCTGCCGCATAGAAGTGCCTGGCTGGTTCAAC<br>GATGTAAAGATAAACGTGCGCCTGAATCTACAGAGAGCCTCAACAACCACGCACAGAACAGCAACCACCA<br>CCCACACGCAGAACAACAACAACAAGCCCCACCACCACCCGACAAATGACAACAACCCCAGCTGCACTTCC<br>AACAACAGTCGTGACCACACCCGATCTCACAACCGGAACACCACTCCAGATGACAACCATTGCCGTCTTC<br>ACAACAGCAAACACGTGCCTTTCACTAACCCCAAGCACCCTTCCGGAGGAAGCCACAGGTCTTCTGACTC<br>CCGAGCCTTCTAAGGAAGGGCCCATCCTCACTGCAGAATCAGAAACTGTCCTCCCCAGTGATTCCTGGAG<br>TAGTGTTGAGTCTACTTCTGCTGACACTGTCCTGCTGACATCCAAAGCATCTGATACAGCAGTTCCTGAG |

SUMMARY OF THE SEQUENCE LISTING

| SEQ ID NO: | SEQUENCE |
|---|---|
| | CAGAACAAAACAACAAAAACAGGACAGATGGATGGAATACCCATGTCAATGAAGAATGAAATGCCCATCT<br>CCCAACTACTGATGATCATCGCCCCCTCCTTGGGATTTGTGCTCTTCGCATTGTTTGTGGCGTTTCTCCT<br>GAGAGGGAAACTCATGGAAACCTATTGTTCGCAGAAACACACAAGGCTAGACTACATTGGAGATAGTAAA<br>AATGTCCTCAATGACGTGCAGCATGGAAGGGAAGACGAAGACGGCCTTTTTACCCTCTAACAACGCAGTA<br>GCATGTTAGATTGAGGATGGGGGCATGACACTCCAGTGTCAAAATAAGTCTTAGTAGATTTCCTTGTTTC<br>ATAAAAAAGACTCACTTATTCCATGGATGTCATTGATCCAGGCTTGCTTTAGTTTCATGAATGAAGGGTA<br>CTTTAGAGACCACAACTTCTCTGTCAAAAA |

What is claimed is:

1. A method of treating cancer in a subject, the method comprising administering to the subject an effective amount of:
   (a) an anti-PD-L1 antibody comprising a means for binding PD-L1 and inhibiting binding of PD-L 1 to the PD-1 receptor; and
   (b) an anti-TIM-4 antibody comprising a means for binding TIM-4 and inhibiting efferocytosis of tumor cells.

2. The method of claim 1, wherein the anti-TIM-4 antibody binds to the IgV domain of TIM-4.

3. The method of claim 1, wherein the anti-TIM-4 antibody binds to the FG-CC" cleft of the IgV domain.

4. The method of claim 1, wherein the anti-PD-L1 antibody comprises the CDR1, CDR2 and CDR3 domains in a heavy chain variable region having the sequence set forth in SEQ ID NO: 1, and the CDR1, CDR2 and CDR3 domains in a light chain variable region having the sequence set forth in SEQ ID NO: 3.

5. The method of claim 1, wherein the anti-PD-L1 antibody comprises:
   (a) a heavy chain variable region CDR1 having the sequence set forth in SEQ ID NO: 5
   (b) a heavy chain variable region CDR2 having the sequence set forth in SEQ ID NO: 6;
   (c) a heavy chain variable region CDR3 having the sequence set forth in SEQ ID NO: 7;
   (d) a light chain variable region CDR1 having the sequence set forth in SEQ ID NO: 8;
   (e) a light chain variable region CDR2 having the sequence set forth in SEQ ID NO: 9; and
   (f) a light chain variable region CDR3 having the sequence set forth in SEQ ID NO: 10.

6. The method of claim 1, wherein the anti-PD-L1 antibody comprises heavy and light chain variable regions having the sequences set forth in SEQ ID NOs: 1 and 3, respectively.

7. The method of claim 1, wherein the anti-PD-L1 antibody and the anti-TIM-4 antibody are formulated for intravenous administration.

8. The method of claim 1, wherein the anti-PD-L1 antibody is administered prior to administration of the anti-TIM-4 antibody.

9. The method of claim 1, wherein the anti-TIM-4 antibody is administered prior to administration of the anti-PD-L1 antibody.

10. The method of claim 1, wherein the anti-TIM-4 antibody and the anti-PD-L1 antibody are administered simultaneously.

11. The method of claim 1, wherein the cancer is a cancer selected from the group consisting of leukemia, lymphoma, blastoma, carcinoma, sarcoma, small-cell lung cancer, non-small cell lung cancer, gastrointestinal cancer, colorectal cancer, glioblastoma and colon carcinoma.

12. The method of claim 1, which comprises administration of an additional therapeutic agent.

13. The method of claim 12, wherein the additional therapeutic agent is a cytotoxin or chemotherapeutic agent.

14. The method of claim 1 wherein the subject is a human.

15. A method for inhibiting PD-1 signaling as a means of treating a subject diagnosed with cancer, said method comprising administering to the subject an effective amount of:
- (a) an anti-PD-L1 antibody comprising a means for binding PD-L1, wherein the anti-PD-L1 antibody inhibits the binding of PD-L1 to the PD-1 receptor; and
- (b) an anti-TIM-4 antibody comprising a means for binding TIM-4, wherein the anti-TIM-4 antibody inhibits efferocytosis of tumor cells.

* * * * *